United States Patent [19]

Lednicer

[11] 3,979,444

[45] Sept. 7, 1976

[54] 4-ARYLCYCLOHEXYLAMINES

[75] Inventor: Daniel Lednicer, Portage, Mich.

[73] Assignee: The Upjohn Company, Kalamazoo, Mich.

[22] Filed: May 28, 1974

[21] Appl. No.: 474,037

[52] U.S. Cl. ............................ 260/490; 260/239 B; 260/247; 260/247.2 B; 260/247.2 A; 260/268 R; 260/293.62; 260/293.72; 260/293.81; 260/293.84; 260/326.43; 260/326.5 R; 260/326.8; 260/570.5 CA; 424/244; 424/248; 424/250; 424/267; 424/274; 424/311; 424/325

[51] Int. Cl.² ...................................... C07C 93/18

[58] Field of Search ...... 260/490, 570.5 CA, 293.67

[56] References Cited
UNITED STATES PATENTS

| | | | |
|---|---|---|---|
| 3,365,451 | 1/1968 | Brannock et al. ............... | 260/247.7 |
| 3,652,589 | 3/1972 | Flick et al. .................... | 260/326.5 M |
| 3,850,935 | 11/1974 | Nakao et al. ................... | 260/293.52 |

*Primary Examiner*—G. Thomas Todd
*Attorney, Agent, or Firm*—William G. Jameson; Roman Saliwanchik

[57] ABSTRACT

The invention relates to novel 4-hydroxymethyl-(acyloxymethyl and methyl)-4-arylcyclohexylamines embraced by the formula

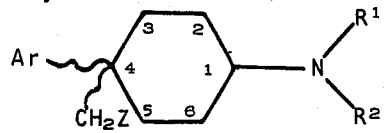

wherein Ar is an aromatic ring selected from the group consisting of phenyl and naphthyl, each of which has from zero through three substituents independently selected from the group consisting of fluorine, chlorine, bromine, lower alkyl of one through three carbon atoms, lower alkoxy of one through three carbon atoms, and lower alkylthio of one through three carbon atoms; Z is selected from the group consisting of hydrogen, hydroxy and lower acyloxy of one through four carbon atoms; ~ is a generic expression denoting cis and trans stereoconfiguration and mixtures thereof, with the proviso that when the stereoconfiguration of the linkage connecting the cyclohexane ring and CH₂Z is cis to the amino group, the linkage connecting the cyclohexane and Ar rings is trans, and vice versa; R¹ is selected from the group consisting of hydrogen and lower alkyl of one through three carbon atoms; R² is selected from the group consisting of hydrogen, lower alkyl of one through three carbon atoms,

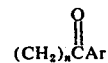

wherein n is 2 through 5 and Ar has the same meaning as above; R¹ and R² taken together with —N< is a saturated heterocyclic amino radical selected from the group consisting of unsubstituted and substituted pyrrolidino, piperidino, hexamethylenimino, morpholino and piperazino; and pharmacologically acceptable acid addition salts thereof. It also relates to intermediates and processes for the preparation of the aforesaid novel compounds (I) and novel derivatives thereof. The administration to humans and animals of the novel compounds (I) depresses their central nervous systems and lowers their blood pressures.

25 Claims, No Drawings

4-ARYLCYCLOHEXYLAMINES

BRIEF SUMMARY OF THE INVENTION

This invention relates to new organic compounds and is particularly concerned with those embraced by the formula

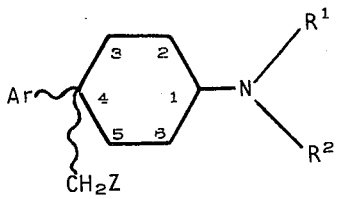

wherein Ar is an aromatic ring selected from the group consisting of phenyl and naphthyl, each of which has from zero through three substituents independently selected from the group consisting of fluorine, chlorine, bromine, lower alkyl of one through three carbon atoms, lower alkoxy of one through three carbon atoms, and lower alkylthio of one through three carbon atoms; Z is selected from the group consisting of hydrogen, hydroxy and lower acyloxy of one through four carbon atoms; ~ is a generic expression denoting cis and trans stereoconfiguration and mixtures thereof, with the proviso that when the stereoconfiguration of the linkage connecting the cyclohexane ring and $CH_aZ$ is cis to the amino group, the linkage connecting the cyclohexane and Ar rings is trans, and vice versa; $R^1$ is selected from the group consisting of hydrogen and lower alkyl of one through three carbon atoms; $R^2$ is selected from the group consisting of hydrogen, lower alkyl of one through three carbon atoms

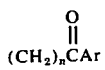

wherein n is 2 through 5 and Ar has the same meaning as above; $R^1$ and $R^2$ taken together with —N< is a saturated heterocyclic amino radical selected from the group consisting of unsubstituted and substituted pyrrolidino, piperidino, hexamethylenimino, morpholino and piperazino; and pharmacologically acceptable acid addition salts thereof.

Examples of Ar are phenyl, m-chlorophenyl, p-fluorophenyl, m-ethylphenyl, o-methylphenyl, 3,4-dimethoxyphenyl, 2,4-dimethylphenyl, 2-bromo-5-ethylphenyl, 2-chloro-3,5-dipropylphenyl, 2,4,6-trichlorophenyl, naphthyl, 1-methylnaphthyl, 2-fluoronaphthyl, 2-chloro-7-methylnaphthyl and 2-bromo-4-fluoro-7-methylnaphthyl. Examples of lower alkyl of one through three carbon atoms are methyl, ethyl, propyl and isopropyl. Examples of lower alkoxy of one through three carbon atoms are methoxy, ethoxy, propoxy, and isopropoxy. Examples of lower alkylthio of one through three carbon atoms are methylthio, ethylthio, propylthio and isopropylthio. Examples of lower acyloxy of one through four carbon atoms are formyloxy, acetoxy, propionyloxy and butyroxy. Examples of unsubstituted and substituted pyrrolidino, piperidino, hexamethylenimino, morpholino and piperazino are pyrrolidino, 2-methylpyrrolidino, piperidino, 2-ethylpiperidino, hexamethylenimino, 3-methoxyhexamethylenimino, 2-ethyl-4-methylhexamethylenimino, morpholino, 2,3-dimethylmorpholino, 2-ethoxymorpholino, piperazino, 2-methylpiperazino, 2-ethyl-4-methylpiperazino and 3-isopropylpiperazino. Examples of

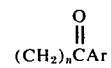

wherein n is 2 through 5 and Ar is an aromatic ring selected from the group consisting of phenyl and naphthyl, each of which has from zero through three substituents independently selected from the group consisting of fluorine, chlorine, bromine, lower alkyl of one through three carbon atoms, lower alkoxy of one through three carbon atoms, and lower alkylthio of one through three carbon atoms are: 4-oxo-4-(p-fluorophenyl)butyl, 4-oxo-4-(2-chloro-1-methylphenyl)butyl, 4-oxo-4-phenylbutyl, 4-oxo-4-(p-tolyl)butyl, 4-oxo-4-(p-methoxyphenyl)butyl, 4-oxo-4-(p-chlorophenyl)butyl, 4-oxo-(2-bromo-4-chlorophenyl)butyl, 4-oxo-(o-propoxy-α-naphthyl)butyl, 2-oxo-(m-ethyl-α-naphthyl)ethyl, 3-oxo-3-(p-bromophenyl)propyl. 5-oxo-4-(o-ethoxyphenyl)pentyl, and the isomeric forms. thereof.

The novel 4-hydroxymethyl(acyloxymethyl and methyl)-4-arylcyclohexylamines of Formula I exist either in the non-protonated (free base) form or in the protonated (acid addition salt) form, depending on the pH of the environment. They form stable protonates, i.e., acid addition salts, on neutralization of the free base form with suitable acids, for example, hydrochloric, hydrobromic, sulfuric, phosphoric, nitric, acetic, propionic, palmitic, benzoic, salicylic, hexynoic, phenylbutyric, naphthoic, glycolic, succinic, nicotinic, tartaric, maleic, mallic, pamoic, methanesulfonic, citric and lactic acids, and the like. Conversely, the free base of the novel compounds of Formula I can be obtained from a salt (e.g., from the hydrochloride or sulfate salts) by neutralization with a base such as sodium hydroxide, extracting with an immiscible solvent, for example chloroform, drying the extract, for example, with anhydrous sodium sulfate, and removing the solvent by evaporation.

The novel compounds (I) of this invention, intermediates therefor and processes for their production are illustratively represented by the following sequence of formulae

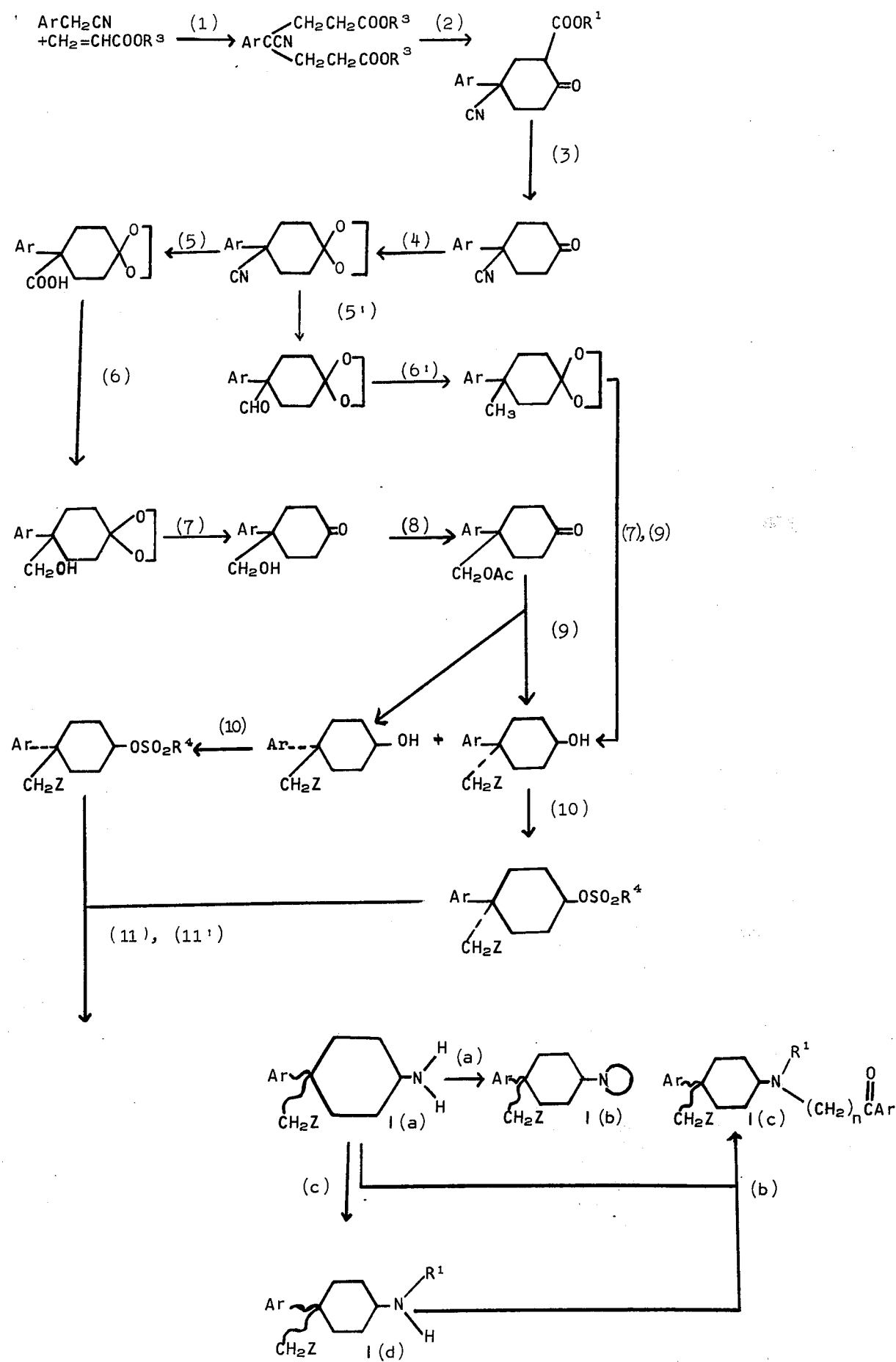

wherein Ar, Z, ~, R¹ and n have the same meaning as above, R³ is lower alkyl of one through three carbon atoms, R⁴ is selected from the group consisting of alkyl of one through three carbon atoms and aryl of six through ten carbon atoms and the symbol -N represents a saturated heterocyclic amino radical selected from the group consisting of unsubstituted and substituted pyrrolidino, piperidino, hexamethylenimino, morpholino and piperazino.

The compounds embraced by Formula I of the flow-sheet, above, are prepared by the procedures indicated therein, employing the methods and reactions described below.

1. The first step of the process for preparing the compounds designated I(a) in the above flow-sheet involves a Michael-type condensation, namely, of an arylacetonitrile with an alkylacrylate in a solvent (such as t-butyl alcohol) from room to reflux temperature in the presence of any basic catalyst (e.g., methanolic tetramethyl ammonium hydroxide), to yield a corresponding dialkyl-4cyano-4-arylpimelate.

2. The next step of the process comprises cyclization, e.g., with sodium hydride or potassium t-butoxide in a toluene solvent at elevated (reflux) temperature of a dialkyl-4-cyano-4-arylpimelate produced in step (1), to yield a corresponding alkyl 5-cyano-5-aryl-2-oxocyclohexanecarboxylate. 3. An alkyl 5-cyano-5-aryl-2-oxocyclohexanecarboxylate obtained in step (2) is hydrolyzed and decarboxylated, e.g., by heating in acetic acid solvent (at reflux) with a dilute acid (such as sulfuric), to five a corresponding 4-cyano-4-arylcyclohexanone. 4. A 4-cyano-4-arylcyclohexanone produced in step (3) is ketalized, e.g., by heating (at reflux) in benzene with an alkylene glycol (in the presence of a catalyst such as p-toluenesulfonic acid), to yield a corresponding 4-cyano-4-arylcyclohexanone, alkylene ketal. 5. A 4-cyano-4-arylcyclohexanone alkylene ketal produced in step (4) is converted, e.g., by heating (at reflux) with an alkali metal hydroxide (preferably potassium hydroxide) in a relatively high boiling solvent (such as ethylene glycol), to a corresponding 4-carboxy-4-arylcyclohexanone, alkylene ketal. 5'. This step is a modification of step (5). A 4-cyano-4-arylcyclohexanone alkylene ketal in a solvent such as tetrahydrofuran, on treatment (at moderate to low temperature) with lithium aluminum hydride in a solvent such as tetrahydrofuran, yields a corresponding 4-formyl-4-arylcyclohexanone, alkylene ketal. 6. The 4-carboxy group of a 4-carboxy-4-arylcyclohexanone alkylene ketal prepared in step (5) is reduced, e.g., with lithium aluminum hydride (in a solvent such as tetrahydrofuran) at elevated (reflux) temperature, to yield a corresponding 4-hydroxymethyl-4-arylcyclohexanone, alkylene ketal. 6'. The 4-formyl group of a 4-formyl-4-arylcyclohexanone, alkylene ketal produced in step (5') is reduced, e.g., with hydrazine in a high boiling solvent (such as ethylene glycol) at elevated (reflux) temperature, to give a corresponding 4-methyl-4-arylcyclohexanone, alkylene ketal. 7. In this step, the alkylene ketal protective group of a 4-hydroxymethyl-4-arylcyclohexanone alkylene ketal resulting from step (6) is removed by employing conventional reagents, e.g., by stirring an aforesaid compound with dilute aqueous acid in acetone at moderate (room) temperature for a protracted (5 to 30 hour) period, to give a corresponding 4-hydroxymethyl-4-arylcyclohexanone. 8. A 4-hydroxymethyl-4-arylcyclohexanone prepared in step (7) is converted by known methods, e.g., by mixing (at moderate or low temperature) with an anhydride of a hydrocarbon carboxylic acid (e.g., acetic anhydride) in the presence of an esterification catalyst such as pyridine, to a corresponding 4-acyloxymethyl-4-arylcyclohexanone. 9. In this step of the process, a 4-acyloxy-4-arylcyclohexanone produced in step (8) is reduced, e.g., with sodium borohydride (with isopropanol being the preferred solvent), to give a mixture of a corresponding 4-cis-acyloxymethyl-4-trans-arylcyclohexanol and a corresponding 4-trans-acyloxymethyl-4-cis-arylcyclohexanol; the thus produced isomers being separated and purified by conventional procedures, such as chromatography or fractional crystallization. Mixing (preferably at low temperature for from about 3 to about 24 hours) a 4-cis (or trans)-acyloxymethyl-4-trans (or cis)-arylcyclohexanol obtained in step (9) in an amine base (such as pyridine) with an alkyl (or aryl) sulfonyl halide (such as methanesulfonyl chloride or p-toluenesulfonyl chloride), yields a corresponding 4-cis (or trans)-acyloxymethyl-4-trans (or cis) -arylcyclohexanol alkyl (or aryl) sulfonate. 11. In this step, a 4cis (or trans)-acryloxymethyl-4-trans (or cis)-arylcyclohexanol alkyl (or aryl) sulfonate resulting from step (10) and sodium azide in a solvent such as dimethylformamide, on heating (at from about 65 to about 100° C. for from about 4 to about 20 hours), yields (with inversion of stereoconfiguration corresponding 4-trans (or cis)-acyloxymethyl-4-cis (or trans)-arylcyclohexan-1-yl-azides, which compounds on reduction of their azido and acyloxy functions, e.g., with lithium aluminum hydride in a solvent such as tetrahydrofuran, gives corresponding 4-trans (or cis)-cis-hydroxymethyl-4-cis (or trans)-arylcyclohexylamines [I(a), z=OH] in their free base form. On treating a solvent extract of the thus produced compounds with an etheral solution of a suitable acid, their acid addition salt forms are obtained. 11'. This step is a modification of the second part of step (11), namely, catalytically reducing (instead of employing lithium aluminum hydride), a 4-trans (or cis)-acyloxymethyl-4-cis (or trans)-arylcyclohexan-1-ylazide by mixing it in a solvent such as ethyl acetate with a catalyst such as palladium on carbon in an atmosphere of hydrogen, thereby leaving the acyloxy function intact, to give a corresponding 4-trans (or cis)-acyloxymethyl-4-cis (or trans)-4-arylcyclohexylamine [I (a), z=OAc].

The free base or acid addition salt forms of the 4-trans (and cis)-hydroxymethyl (acyloxymethyl or methyl)-4-cis (and trans)-arylcyclohexylamines [I (a)] obtained as in steps (11) and (11'), above, are employed as starting materials for producing a variety of derivatives thereof, for example, in accordance with the methods described in (a) through (c) that follow.

a. Heating (e.g., under reflux for from about 8 to about 24 hours) a 4-trans (or cis)-hydroxymethyl (acyloxymethyl or methyl)-4-cis (or trans)-arylcyclohexylamine [I-(a)] with a dihaloalkane gives a corresponding 1-cis (or trans)-aryl-4-trans (or cis)-(1-single ring nitrogen containing heterocyclo)-1-cyclohexanemethanol (cyclohexanemethanol acylate or cyclohexylmethane) [I (b)], which on dissolving in ether and treating with an ethereal solution of an appropriate acid, yields the corresponding acid addition salt. For example, heating a 4-trans (or cis)-hydroxymethyl-4-cis (or trans)-arylcyclohexylamine [I (a)] with 1,5-diiodopentane, 1,4-dibromobutane or 1,6-diiodohexane, yields, respectively, a corresponding 1-cis (or trans)-aryl-4-trans (or cis)-(1-piperidino)-1-cyclohexanemethanol [I (b)], 1-cis (or trans)-aryl-4-trans (or cis)-(1- pyrrolidino)-1-cyclohexanemethanol [I (b)] or 1-cis (or trans)-aryl-4-trans (or cis)-(1-hexamethyleneimino)-1-cyclohexanemethanol [I (b)], which can be converted to their acid addition salt counterparts in the manner described in the immediately preceding sentence. b. The production of a compound selected from the group consisting of the free bases and acid addition salts of a compound of the formula

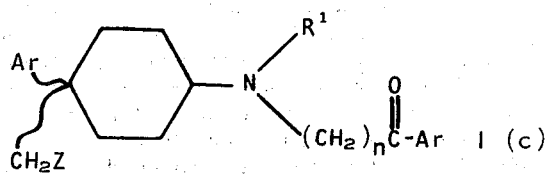

wherein Ar, Z, ~, R¹ and n have the same meaning as above, comprises reacting (in the presence of an alkali metal iodide and an alkali metal carbonate a compound selected from the group consisting of the free bases and acid addition salts of a corresponding 4-trans (or cis)-hydroxymethyl (acyloxmethyl or methyl)-4-cis )and trans)-arylcyclohexylamine of the formula

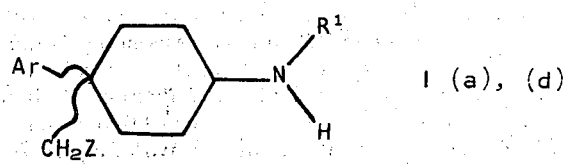

wherein Ar, Z, ~ and R¹ have the same meaning as above, with a corresponding compound of the formula

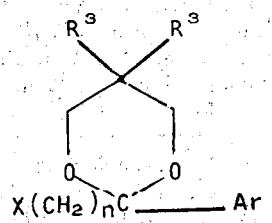

wherein Ar, n and R³ have the same meaning as above and X is selected from the group consisting of chlorine and bromine, followed by hydrolyzing (i.e., deketalizing) a thus produced compound e.g., with aqueous acid in an alkanol.

c. Heating a mixture of the free base form of a 4-trans-(or cis)-hydroxymethyl (acyloxymethyl or methyl)-4-cis (or trans)-arylcyclohexylamine [I (a)] and an alkyl ester such as ethyl formate, ethyl acetate or methyl propionate (e.g., under reflux), yields a corresponding N-[4-trans (or cis)-hydroxymethyl(acyloxymethyl or methyl)-4-cis (or trans)-arylcyclohexyl]formamide (acetamide or propionamide) (I). Reducing a thus produced amide (I), for example, by heating it in a solvent such as tetrahydrofuran (e.g., under reflux) with lithium aluminum hydride, yields a corresponding N-alkyl-[4-trans (or cis)-hydroxymethyl or methyl)-4-cis (or trans)-arylcyclohexyl]amine (I (c)]. Dissolving a thus produced compound in ether and treating it with an etheral solution of an appropriate acid gives a corresponding acid addition salt thereof.

All of the compounds included within Formula I of the flow-sheet, above, can be isolated from their respective reaction mixtures by conventional means, for example, when a water-miscible solvent is used, by pouring the reaction mixture into water and separating the resulting precipitate by filtration or by extraction with water-immiscible solvents. Additional purification of the products can be accomplished by conventional means, for example, by elution chromatography from an adsorbent column with a suitable solvent such as acetone, ethyl acetate, ether, methylene chloride and Skellysolve B (hexanes), mixtures and combinations of these solvents; also by gradient elution chromatography from an adsorbent column with a suitable mixture of solvents, such as, methylene chloride-Skellysolve B, acetone-Skellysolve B, and the like.

The free bases and pharmacologically acceptable acid addition salts of the compounds of Formula 1 are useful as central nervous system (CNS) depressants when administered to humans and animals. They possess tranquilizing activity and are consequently useful in humans for controlling anxiety and schizophrenia; in animals the aforesaid compounds are useful for their calming effects and can be given to reduce anxiety and aggressive behavior. These compounds have been shown to possess CNS depressing activity via the loss of righting reflex, traction, chimney, dish and pedestal tests carried out in the art-accepted manner described by Bossier et al., in Medicina Experimentalis 4, 145 (1961).

Tranquilizing effects of the compounds of this invention were shown by the following tests in mice:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves a standard pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1) running convulsions followed by (2) tonic extensor fits; followed by death (3). For example, 4'-fluoro-4-[[4-trans-(p-fluorophenyl)-4-cis-(hydroxymethyl)-r-1-cyclohexyl]amino]butyrophenone hydrochloride (I), (by intraperitoneal injection in mice) gave the following results, (expressed as $ED_{50}$ in mg./kg.) in the following tests:

| Chimney | Dish | Pedestal | Nicotine antagonism (2), | (3) |
|---|---|---|---|---|
| 9 | 0.9 | 3.6 | 2 | 3.2 |

As tranquilizers, the compounds of Formula I and their pharmacologically acceptable acid addition salts can be prepared and administered to humans, mammals, birds and animals in a wide variety of oral or parenteral dosage forms, singly or in admixture with other coacting compounds, in doses of from about 10 mg. to about 100 mg./kg., depending on the severity of the condition being treated and the recipient's response to the medication.

The free bases and pharmacologically acceptable acid addition salts of the compounds of Formula I are also useful in lowering blood pressure when administered to humans and animals. This activity makes them useful in the treatment of essential hypertension. These compounds have been shown to possess hypotensive activity when tested in the art-accepted manner described by Weeks and Jones in Proc. Soc. Exp. Biol. and Med. 104, 646 (1960). For example, 4'-fluoro-4-[[4-trans-(p-fluorophenyl)-4-cis-(hydroxymethyl)-r-1-cyclohexyl]amino]butyrophenone hydrochloride I (by oral administration in rats) gave an $MED_{100}$ (minimal effective dose) of 10 mg./kg.

As hypotensives, the compounds of Formula I and their pharmacologically acceptable acid addition salts can be prepared and administered to humans, mammals, birds and animals in a wide variety of oral or parenteral dosage forms, singly or in admixture with other coacting compounds in doses of from about 1 mg. to about 10 mg./kg., depending on the severity of the condition being treated and the recipient's response to the medication.

The compounds of Formula I (used as tranquilizers and/or hypotensives) can be administered with a pharmaceutical carrier which can be solid material or a liquid in which the compound is dissolved, dispersed or suspended. The solid compositions can take the form of tablets, powders, capsules, pills or the like, preferable in unit dosage forms for simple administration or precise dosages. The liquid compositions can take the form of solutions, emulsions, suspensions, syrups, or elixirs.

The preferred compounds of this invention (as free bases or phamacologically acceptable acid addition salts) include those embraced by the formula

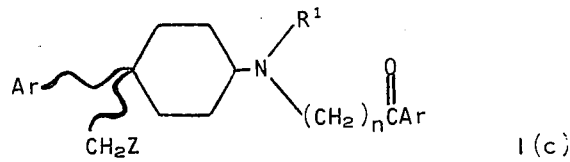

I(c)

wherein Ar, Z,~, $R^1$ and n have the same meaning as above.

More preferred compounds of Formula I(c) are those covered by the formula

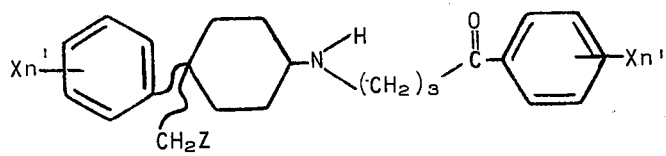

wherein Z and ~ have the same as above and X is fluorine, chlorine, bromine, lower alkyl of one through three carbon atoms, lower alkoxy of one through three carbon atoms and lower alkylthio of one through three carbon atoms and n' is zero through three.

Further preferred compounds of Formula I(c) are those included within the formula

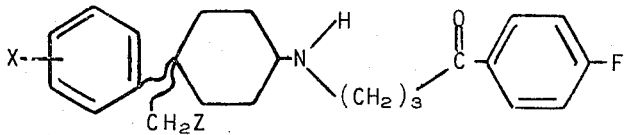

wherein X, Z and ~ have the same meaning as above.

DETAILED DESCRIPTION

The following examples are illustrative of the manner of making and using the invention and set forth the best mode contemplated by the inventor of carrying out his invention, but are not to be construed as limiting the scope thereof, as obvious modifications and equivalents will be apparent to those skilled in the art, and the invention is therefore to be limited only by the scope of the appended claims.

Example 1 Dimethyl-4-cyano-4-phenylpimelate

A mixture of 29.26 g. (0.25 mole) of the known compound phenylacetonitrile and 116 ml. of the known compound methyl acrylate in 120 ml. of t-butyl alcohol is heated to reflux. The heat is removed and 38 ml. of 40% methanolic Triton B (tetramethyl ammonium hydroxide) in 56 ml. of t-butyl alcohol is quickly added. After about 4 hours of heating at reflux the mixture is allowed to cool and taken up in water and benzene. The organic layer is washed successively with 2.5 N hydrochloric acid, water and brine and then evaporated to dryness. The residue is distilled under vacuum, first at 40 mm. of mercury to remove excess methyl acrylate and then at 0.45 mm. to give 55.15 g. (76.3% yield) of dimethyl-4-cyano-4-phenyl pimelate, having a boiling point of 183° to 186°C.

Example 2
Dimethyl-4-cyano-4-(4-chlorophenyl)pimelate

A mixture of 25 g. (0.165 mole) of the known compound (p-chlorophenyl)acetonitrile and 77 ml. of methyl acrylate in 80 ml. of t-butyl alcohol is heated to reflux. The heat is removed and 25 ml. of 40% methanolic Triton B in 37 ml. of t-butyl alcohol quickly added. After about 4 hours of heating at reflux the mixture is allowed to cool and taken up in water and benzene. The organic layer is washed successively with 2.5 N hydrochloric acid, water and brine and then evaporated to dryness. The residue is distilled under vacuum, first at 40 mm. of mercury to remove excess methyl acrylate and then at 0.35 mm. to give 38.06 g. (71.4% yield) of dimethyl-4-cyano-4-(4-chlorophenyl)pimelate, having a boiling point of 186° to 191°C. The nuclear magnetic resonance (NMR) spectrum of the compound confirms its expected structure.

Example 3
Dimethyl-4-cyano-4-(4-fluorophenyl)pimelate

A mixture of 25 g. (0.185 mole) of the known compound p-fluorophenylacetonitrile and 86 ml. of methyl acrylate in 90 ml. of t-butyl alcohol is heated to reflux. The heat is removed and 28.1 ml. of 40% methanolic Triton B in 42 ml. of t-butyl alcohol quickly added. After about 4 hours of heating at reflux the mixture is allowed to cool and taken up in water and benzene. The organic layer is washed successively with 2.5 N hydrochloric acid, water and brine and then evaporated to dryness. The residue is distilled under vacuum, first at 40 mm. of mercury to remove methyl acrylate and then at 0.25 to 0.30 mm. to give 41 g. (72.2% yield) of dimethyl-4-cyano-4-(4-fluorophenyl)pimelate having a boiling point of 179° to 181°C. The NMR spectrum of the compound confirms its expected structure.

Example 4
Dimethyl-4-cyano-4-(4l-methoxyphenyl)pimelate

A mixture of 36.75 g. (0.25 mole) of the known compound (p-methoxyphenyl)acetonitrile and 116 ml. of methyl methacrylate in 120 ml. of t-butyl alcohol is heated to reflux. The heat is removed and 38 ml. of 40% methanolic Triton B in 56 ml. of t-butyl alcohol quickly added. After about 4 hours of heating at reflux the mixture is allowed to cool and taken up in water and benzene. The organic layer is washed successively with 2.5 N hydrochloric acid, water and brine and then evaporated to dryness. The residue is distilled under vacuum, first at 40 mm. of mercury to remove excess methyl acrylate and then at 0.6 to 0.75 mm. to give 55.9 g. (70.2% yield) of dimethyl-4-cyano-4-(4-methoxyphenyl)pimelate, having a boiling point of 205° to 210°C. The NMR spectrum of the compound confirms its expected structure.

Example 5
Dimethyl-4-cyano-4-(3,4-dimethoxyphenyl)pimelate

A mixture of 25 g. (0.141 mole) of the known compound (3,4-dimethoxyphenyl)acetonitrile and 66 ml. of methyl acrylate in 70 ml. of t-butyl alcohol is heated to reflux. The heat is removed and 21.5 ml. of 40% methanolic Triton B in 32 ml. of t-butyl alcohol quickly added. After about 4 hours of heating at reflux the mixture is allowed to cool and taken up in water and benzene. The organic layer is washed successively with 2.5 N hydrochloric acid, water and brine and then evaporated to dryness. The residue is distilled under vacuum, first at 40 mm. of mercury to remove excess methyl acrylate and then at 0.20 mm. to give 32.22 g. (65.4% yield) of dimethyl-4-cyano-4-(3,4-dimethoxyphenyl)pimelate, having a boiling point of 210° to 214°C. The NMR spectrum of the compound confirms its expected structure.

Example 6 Dimethyl-4-cyano-4-(1-naphthyl)pimelate

A mixture of 20.9 g. (0.125 mole) of the known compound (1-naphthyl)acetonitrile and 58 ml. of methyl acrylate in 60 ml. of t-butyl alcohol is heated to reflux. The heat is removed and 19 ml. of 40% methanolic Triton B in 28 ml. of t-butyl alcohol quickly added. After about 4 hours of heating at refux the mixture is allowed to cool and taken up in water and benzene. The organic layer is washed successively with 2.5 N hydrochloric acid, water and brine and then evaporated to dryness. The residue is distilled under vacuum, first at 40 mm. of mercury to remove excess methyl acrylate and then at 0.5 mm. to give 24.96 g. (59% yield) of dimethyl-4-cyano-4-(1-naphthyl)pimelate, having a boiling point of 209° to 219°C. The NMR spectrum of the compound confirms its expected structure.

Following the procedure of Examples 1 through 6 but substituting other known acetonitriles and alkyl acrylates, such as 1. (2-bromo-4,5-dimethoxyphenyl)acetonitrile and methyl acrylate,
2. (3-bromo-4-ethoxyphenyl)acetonitrile and ethyl acrylate,
3. (5-bromo-2-methoxyphenyl)acetonitrile and propyl acrylate,
4. (o-bromophenyl)acetonitrile and isopropyl acrylate,
5. α-(m-bromophenyl)cyclohexaneacetonitrile and methyl acrylate,
6. (5-bromo-3-propoxyphenyl)acetonitrile and ethyl acrylate,
7. (3-chloro-4-fluorophenyl)acetonitrile and propyl acrylate,
8. (2-chloro-5-methoxyphenyl)acetonitrile and isopropyl acrylate,
9. (3-chloro-6-methoxy-2-methylphenyl)acetonitrile and methyl acrylate,
10. (5-chloro-2-methylphenyl)acetonitrile and ethyl acrylate,
11. (2,4-dichlorophenyl)acetonitrile and isopropyl acrylate,
12. (2,3-dichlorophenyl)acetonitrile and methyl acrylate,
13. (2,6-dichlorophenyl)acetonitrile and ethyl acrylate,
14. (2,4-difluorophenyl)acetonitrile and propyl acrylate,
15. (3,4-difluorophenyl)acetonitrile and isopropyl acrylate,
16. (2,4-dimethoxyphenyl)acetonitrile and methyl acrylate,
17. (2,6-diisopropylphenyl)acetonitrile and ethyl acrylate,
18. (2,5-dimethoxyphenyl)acetonitrile and propyl acrylate,
19. (3,5-dimethoxyphenyl)acetonitrile and isopropyl acrylate,
20. (2-ethoxy-4-methoxyphenyl)acetonitrile and methyl acrylate,
21. (4-ethoxy-3-methylphenyl)acetonitrile and ethyl acrylate,
22. (5-ethyl-2-methoxyphenyl)acetonitrile and propyl acrylate,
23. (o-ethylphenyl)acetonitrile and isopropyl acrylate,
24. (3-fluoro-4-methoxyphenyl)acetonitrile and ethyl acrylate,
25. (2-fluoro-3,4-dimethoxyphenyl)acetonitrile and propyl acrylate,
26. (m-fluorophenyl)acetonitrile and isopropyl acrylate,
27. (4-isopropoxy-2-methylphenyl)acetonitrile and methyl acrylate,
28. (o-methylphenyl)acetonitrile and ethyl acrylate,
29. (3-methoxy-2,6-dimethylphenyl)acetonitrile and propyl acrylate,
30. [o-(ethylthio)phenyl]acetonitrile and isopropyl acrylate,
31. [p-(methylthio)phenyl]acetonitrile and methyl acrylate,
32. (o-1-naphthylphenyl)acetonitrile and ethyl acrylate, and the like,
yields, respectively, 1. dimethyl-4-cyano-4-(2-bromo-4,5-dimethoxyphenyl)pimelate,
2. diethyl-4-cyano-4-(3-bromo-4-ethoxyphenyl)pimelate,
3. dipropyl-4-cyano-4-(5-bromo-2-methoxyphenyl)pimelate,
4. diisopropyl-4-cyano-4-(o-bromophenyl)pimelate,
5. dimethyl-4-cyano-4-[α-(m-bromophenyl)cyclohexyl]pimelate,
6. diethyl-4-cyano-4-(5-bromo-3-propoxyphenyl)pimelate,
7. dipropyl-4-cyano-4-(3-chloro-4-fluorophenyl)pimelate,
8. diisopropyl-4-cyano-4-(2-chloro-5-methoxyphenyl)pimelate,
9. dimethyl-4-cyano-4-(3-chloro-6-methoxy-2-methylphenyl)pimelate,
10. diethyl-4-cyano-4-(5-chloro-2-methylphenyl)pimelate,
11. diisopropyl-4-cyano-4-(2,4-dichlorophenyl)pimelate,
12. dimethyl-4-cyano-4-(2,3-dichlorophenyl)pimelate,
13. diethyl-4-cyano-4-(2,6-dichlorophenyl)pimelate,
14. dipropyl-4-cyano-4-(2,4-difluorophenyl)pimelate,
15. diisopropyl-4cyano-4-(3,4-difluorophenyl)pimelate,
16. dimethyl-4-cyano-4-(2,4-dimethoxyphenyl)pimelate,
17. diethyl-4-cyano-4-(2,6-diisopropylphenyl)pimelate,
18. dipropyl-4-cyano-4-(2,5-dimethoxyphenyl)pimelate,
19. diisopropyl-4-cyano-4-(3,5-dimethoxyphenyl)pimelate,
20. dimethyl-4-cyano-4-(2-ethoxy-4-methoxyphenyl)pimelate,
21. diethyl-4-cyano-4-(4-ethoxy-m-methylphenyl)pimelate,
22. dipropyl-4-cyano-4-(5-ethyl-2-methoxyphenyl)pimelate,
23. diisopropyl-4-cyano-4-(o-ethylphenyl)pimelate,
24. diethyl-4-cyano-4-(3-fluoro-4-methoxyphenyl)pimelate,
25. dipropyl-4-cyano-4-(2-fluoro-3,4-dimethoxyphenyl)pimelate,
26. diisopropyl-4-cyano-4-(m-fluorophenyl)pimelate,
27. dimethyl-4-cyano-4-(4-isopropoxy-2-methylphenyl)pimelate,
28. diethyl-4-cyano-4-(o-methylphenyl)pimelate,
29. dipropyl-4-cyano-4-(3-methoxy-2,6-dimethylphenyl)pimelate,
30. diisopropyl-4-cyano-4-[o-(ethylthio)phenyl]pimelate,
31. dimethyl-[p-(methylthio)phenyl]pimelate,
32. diethyl-4-cyano-4-(o-1-naphthylphenyl)pimelate
and the like.

Example 7 Methyl 5-cyano-5-(4-chlorophenyl)-2-oxocyclohexanecarboxylate

A dispersion of 57% sodium hydride in mineral oil [15.7 g. (0.037 mole)] is washed twice with toluene and drained by decantation. To this there is added 38.06 g. of dimethyl-4-cyano-4-(4-chlorophenyl)pimelate (prepared in Example 2) in 750 ml. of toluene. After about 5 hours of heating at reflux the mixture is cooled in ice. To this there is slowly added 2.5 N acetic acid until a clear twophase solution results. The organic layer is separated, washed successively with water, sodium bicarbonate solution and brine, and then evaporated to dryness to give 29.8 g. (87% yield) of crystalline methyl 5-cyano-5-(4-chlorophenyl)-2-oxocyclohexanecarboxylate, having a melting point of 141 to 144.5°C.

Example 8 Methyl 5-cyano-5-(4-fluorophenyl)-2-oxocyclohexanecarboxylate

A dispersion of 56% sodium hydride in mineral oil [16.2 g. (0.38 mole)] is washed twice with toluene and drained by decantation. To this there is added 41.08 g. of dimethyl-4-cyano-4-(4-fluorophenyl)pimelate (prepared in Example 3) in 700 ml. of toluene. After about 5 hours of heating at reflux the mixture is cooled in ice. To this there is slowly added 2.5 N acetic acid until a clear twophase solution results. The organic layer is separated, washed successively with water, sodium bicarbonate solution and brine, and then evaporated to dryness to give 33.92 g. (92.7% yield) of waxy solid methyl 5-cyano-5-(4-fluorophenyl)-2-oxocyclohexanecarboxylate.

Example 9 Methyl 5-cyano-5-(4-methoxyphenyl)-2-oxocyclohexanecarboxylate

A dispersion of 56% sodium hydride in mineral oil [23.8 g. (0.56 mole)] is washed twice with toluene and drained by decantation. To this there is added 55.9 g. of dimethyl-4-cyano-4-(4-methoxyphenyl)pimelate (prepared in Example 4) in 100 ml. of toluene. After about 5 hours of heating at reflux the mixture is cooled in ice. To this there is slowly added 2.5 N acetic acid until a clear two-phase solution results. The organic layer is separated, washed successively with water, sodium bicarbonate solution and brine, and then evaporated to dryness to give 48.3 g. (96.3% yield) of gummy methyl 5-cyano-(4-methoxyphenyl)-2-oxocyclohexanecarboxylate.

Example 10 Methyl 5-cyano-5-(3,4-dimethoxyphenyl)-2-oxocyclohexanecarboxylate A dispersion of 57% sodium hydride in mineral oil [1.23 g. (0.029 mole)] is washed twice with toluene and drained by decantation. To this there is added 32.22 g. of dimethyl-4-cyano-4-(3,4-dimethoxyphenyl)pimelate (prepared in Example 5) in 600 ml. of toluene. After about 5-hours of heating at reflux the mixture is cooled in ice. To this there is slowly added 2.5 N acetic acid until a clear two-phase solution results. The organic layer is separated, washed successively with water, sodium bicarbonate solution and brine, and then evaporated to dryness to give 29 g. (99% yield) of crystalline methyl 5-cyano-5-(3,4-dimethoxyphenyl)-2-oxocyclohexanecarboxylate, having a melting point of 102° to 108°C.

Example 11 Methyl 5-cyano-5-(1-naphthyl)-2-oxocyclohexanecarboxylate

A dispersion of 56% sodium hydride in mineral oil [9 g. (0.22 mole)] is washed twice with toluene and drained by decantation. To this there is added 24.96 g. of dimethyl-4-cyano-4-(1-naphthyl)pimelate (prepared in Example 6) in 500 ml. of toluene. After about 5 hours of heating at reflux the mixture is cooled in ice. To this there is slowly added 2.5 N acetic acid until a clear two-phase solution results. The organic layer is separated, washed successively with water, sodium bicarbonate solution and brine, and then evaporated to dryness. The residue is recrystallized from a mixture of acetone and Skellysolve B to give 16.73 g. (79% yield) of methyl 5-cyano-5-(1-naphthyl)-2-oxocyclohexanecarboxylate, having a melting point of 166.5° to 168°C.

Anal. Calcd. for $C_{19}H_{17}NO_3$ : C, 74.25; H, 5.58; N, 4.56. Found: C, 74.22; H, 5.66; N, 4.59.

Following the procedure of Example 7 through 11 but substituting other dialkyl-4-cyano-4-aryl pimelates as starting materials, such as 1. dimethyl 4-cyano-4-phenyl pimelate,
2. diethyl 4-cyano-(3-bromo-4-ethoxyphenyl)pimelate,
3. dipropyl 4-cyano-4-(3,5-dichlorophenyl)pimelate,
4. diisopropyl 4-cyano-4-(3,4-difluorophenyl)pimelate,
5. dimethyl 4-cyano-4-(2,4-dimethoxyphenyl)pimelate
6. diethyl 4-cyano-4-(5-chloro-2-methylphenyl)-pimelate,
7. diisopropyl 4-cyano-4-(3,5-dimethoxyphenyl)-pimelate,
8. dimethyl 4-cyano-4-(2-fluoro-4-methylphenyl)-pimelate,
9. diethyl 4-cyano-4-(o-1-naphthylphenyl)pimelate, and the like, yields, respectively, 1. methyl 5-cyano-5-phenyl-2-oxocyclohexanecarboxylate,
2. ethyl 5-cyano-5-(3-bromo-4-ethoxyphenyl)-2-oxocyclohexanecarboxylate,
3. propyl 5-cyano-5-(3,5-dichlorophenyl)-2-oxocyclohexanecarboxylate,
4. isopropyl 5-cyano-5-(3,4-difluorophenyl)-2-cyclohexanecarboxylate,
5. methyl 5-cyano-5-(2,4-dimethoxyphenyl)-2-cyclohexanecarboxylate,
6. ethyl 5-cyano-5-(5-chloro-2-methylphenyl)-2-cyclohexanecarboxylate,
7. propyl 5-cyano-(3,5-dimethoxyphenyl)-2-cyclohexanecarboxylate,
8. methyl 5-cyano-5-(2-fluoro-4-methylphenyl)-2-cyclohexanecarboxylate,
9. ethyl 5-cyano-4-(o-1-naphthylphenyl)-2-cyclohexanecarboxylate, and the like.

EXAMPLE 12 4-Cyano-4-phenylcyclohexanone

A mixture of 44.7 g. (0.174 mole) of methyl 5-cyano-5-phenyl-2-oxocyclohexanecarboxylate in 1200 ml. of acetic acid and 600 ml. of 10% sulfuric acid is stirred mechanically on a steam bath for about 7 hours. The mixture is then allowed to cool and diluted with water. This mixture is extracted thoroughly with benzene. The organic layer is washed successively with water, sodium bicarbonate solution and brine and evaporated to dryness. The solid residue is recrystallized from a mixture of ethyl acetate and cyclohexane to give 25.75 g. (74.2% yield) of 4-cyano-4-phenylcyclohexanone, having a melting point of 112° to 115°C.

Example 13
4-Cyano-4-(4-chlorophenyl)cyclohexanone

A mixture of 29.8 g. (0.102 mole) of methyl 5-cyano-5-(4-chlorophenyl)-2-oxocyclohexanecarboxylate (prepared in Example 7) in 660 ml. of acetic acid and 330 ml. of 10% sulfuric acid is stirred mechanically on a steam bath for about 24 hours. The mixture is then allowed to cool and diluted with water. This mixture is extracted thoroughly with benzene. The organic layer is washed successively with water, sodium bicarbonate solution and brine and evaporated to dryness. The solid residue is recrystallized from ether to give 19.49 g. (82% yield) of 4-cyano-4-(4-chlorophenyl)cyclohexanone, having a melting point of 94.5° to 97°C.

Anal. Calcd. for $C_{13}H_{12}ClNO$: C, 66.81; H, 5.18; N, 5.99. Found: C, 67.03; H, 5.16; N, 5.95.

Example 14
4-Cyano-4-(4-fluorophenyl)cyclohexanone

A mixture of 33.9 g. (0.123 mole) of methyl 5-cyano-5-(4-fluorophenyl)-2-oxocyclohexanecarboxylate (prepared in Example 8) in 900 ml. of acetic acid and 450 ml. of 10% sulfuric acid is stirred mechanically on a steam bath for about 24 hours. The mixture is then allowed to cool and diluted with water. This mixture is extracted thoroughly with benzene. The organic layer is washed successively with water, sodium bicarbonate solution and brine and evaporated to dryness. The solid residue is recrystallized from ether to give 16.32 g. (75% yield) of 4-cyano-4-(4-fluorophenyl)cyclohexanone, having a melting point of 84° to 88°C.

Anal. Calcd. for $C_{13}H_{12}FNO$: C, 71.87; H, 5.57; N, 6.45. Found: C, 71.64; H, 5.65; N, 6.30.

Example 15
4-Cyano-4-(4-methoxyphenyl)cyclohexanone

A mixture of 48.3 g. (0.168 mole) of methyl 5-cyano-5-(4-methoxyphenyl)-2-oxocyclohexanecarboxylate (prepared in Example 9) in 1100 ml. of acetic acid and 550 ml. of 10% sulfuric acid is stirred mechanically for about 27 hours. The mixture is then allowed to cool and diluted with water. This mixture is extracted thoroughly with benzene. The organic layer is washed successively with water, sodium bicarbonate solution and brine and evaporated to dryness. The solid residue is recrystallized from ether to give 27.61 g. (71.7% yield) of 4-cyano-4-(4-methoxyphenyl)cyclohexanone, having a melting point of 77.5° to 79.5°C.

Anal. Calcd. for $C_{14}H_{15}NO_2$: C, 73.34; H, 6.59; N, 6.11. Found: C, 73.21; H, 6.65; N, 6.00.

EXAMPLE 16
4-Cyano-4-(3,4-dimethoxyphenyl)cyclohexanone

A mixture of 29 g. (0.0915 mole) of methyl 5-cyano-5-(3,4-dimethoxyphenyl)-2-oxocyclohexanecarboxylate (prepared in Example 10) in 600 ml. of acetic acid and 300 ml. of 10% sulfuric acid is stirred mechanically on a steam bath for about 24 hours. The mixture is then allowed to cool and diluted with water. This mixture is extracted thoroughly with benzene. The organic layer is successively washed with water, sodium bicarbonate solution and brine and evaporated to dryness. The solid residue is recrystallized from a mixture of ethyl acetate and cyclohexanone to give 15.96 g. (67.3% yield) of 4-cyano-4-(3,4-dimethoxyphenyl)cyclohexanone, having a melting point of 112.5° to 114.5°C.

Anal. Calcd. for $C_{15}H_{17}NO_3$: C, 69.48; H, 6.61; N, 5.40. Found: C, 69.73; H, 6.64; N, 5.16.

EXAMPLE 17 4-Cyano-4-(1-naphthyl)cyclohexanone

A mixture of 16.73 g. (0.055 mole) of methyl 5-cyano-5-(1-naphthyl)-2-oxocyclohexanecarboxylate (prepared in Example 11) in 400 ml. of acetic acid and 200 ml. of 10% sulfuric acid is stirred mechanically for about 44 hours. The mixture is then allowed to cool and diluted with water. This mixture is extracted thoroughly with benzene. The organic layer is successively washed with water, sodium bicarbonate solution and brine and evaporated to dryness. The solid residue is recrystallized from acetone to give 10.3 g. (76% yield) of 4-cyano-4-(1-naphthyl)cyclohexanone, having a melting point of 213° to 215°C.

Anal. Calcd. for $C_{17}H_{15}NO$: C, 81.90; H, 6.06; N, 5.62. Found: C, 82.32; H, 6.13; N, 5.29.

Following the procedure of Examples 12 through 17 but substituting other alkyl 5-cyano-5-aryl-2-oxocyclohexanecarboxylates as starting materials, such as 1. methyl 5-cyano-5-(o-bromophenyl)-2-oxocyclohexanecarboxylate,
2. ethyl 5-cyano-5-(2-chloro-5-methoxyphenyl)-2-oxocyclohexanecarboxylate,
3. propyl 5-cyano-5-(3-fluoro-6-methylphenyl)-2-oxocyclohexanecarboxylate,
4. isopropyl 5-cyano-5-(3,5-diethoxyphenyl)-2-oxocyclohexanecarboxylate,
5. methyl 5-cyano-5-(2,5-dipropylphenyl)-2-oxocyclohexanecarboxylate,
6. ethyl 5-cyano-5-(2-ethoxy-4-fluoro-6-methylphenyl)2-oxocyclohexanecarboxylate,
7. isopropyl 5-cyano-5-(3-fluoro-5-propylphenyl)-2-oxocyclohexanecarboxylate,
8. methyl 5-cyano-5-[2-methyl-4-propoxy(3-naphthyl)] 2-oxocyclohexanecarboxylate,
9. ethyl 5-cyano-5-(o-1-naphthylphenyl)-2-oxocyclohexanecarboxylate, and the like, yields, respectively, 1. 4-cyano-4-(o-bromophenyl)cyclohexanone,
2. 4-cyano-4-(2-chloro-5-methoxyphenyl)cyclohexanone,
3. 4-cyano-4-(3-fluoro-6-methylphenyl)cyclohexanone,
4. 4-cyano-4-(3,5-diethoxyphenyl)cyclohexanone,
5. 4-cyano-4-(2,5-dipropylphenyl)cyclohexanone,
6. 4-cyano-4-(2-ethoxy-4-fluoro-6-methylphenyl)cyclohexanone,
7. 4-cyano-4-(3-fluoro-5-propylphenyl)cyclohexanone,
8. 4-cyano-4-[2-methyl-4-propoxy-(3-naphthyl)]cyclohexanone,
9. 4-cyano-4-[(o-1-naphthylphenyl)]cyclohexanone, and the like.

EXAMPLE 18 4-Cyano-4-phenylcyclohexanone, ethylene ketal

A mixture of 10 g. (0.05 mole) of 4-cyano-4-phenylcyclohexanone (prepared in Example 12), 2.85 ml. [3.16 g. (0.051 mole)] of ethylene glycol and 0.12 g. of p-toluenesulfonic acid in 90 ml. of benzene is heated at reflux under a Dean-Stark trap for about 6 hours. The solution is then allowed to cool and washed successively with sodium bicarbonate solution, water and brine. The organic layer is evaporated to dryness and the residue recrystallized from cyclohexane to give 11.27 g. (92.7% yield) of 4-cyano-4phenylcyclohexanone, ethylene ketal, having a melting point of 120° to 122.5°C.

Anal. Calcd. for $C_{15}H_{17}N_{02}$: C, 74.05; H, 7.04; N, 5.76. Found: C, 74.10; H, 6.98; N, 5.77.

Example 19
4-Cyano-4-(4-chlorophenyl)cyclohexanone, ethylene ketal

A mixture of 19.49 g. (0.084 mole) of 4-cyano-4-(4-chlorophenyl)cyclohexanone (prepared in Example 13), 4.8 ml. [5.3 g. (0.086 mole)] of ethylene glycol and 0.21 g. of p-toluenesulfonic acid in 150 ml. of benzene is heated at reflux under a Dean-Stark trap for about 6 hours. The solution is then allowed to cool and washed successively with sodium bicarbonate solution, water and brine. The organic layer is evaporated to dryness and the residue recrystallized from cyclohexane to give 21.87 g. (79.1% yield) of 4-cyano-4-(4-chlorophenyl)cyclohexanone, ethylene ketal, having a melting point of 124° to 126.5°C.

Anal. Calcd. for $C_{15}H_{16}ClNO_2$: C, 64.86; H, 5.81; N, 5.04. Found: C, 64.77; H, 5.81; N, 4.92.

Example 20
4-Cyano-4-(4-fluorophenyl)cyclohexanone, ethylene ketal

A mixture of 16.23 g. (0.075 mole of 4-cyano-4-(4-fluorophenyl)cyclohexanone (prepared in Example 14), 6 ml. [6.65 g. (0.11 mole)] of ethylene glycol and 0.6 g. of p-toluenesulfonic acid in 250 ml. of benzene is heated at reflux under a Dean-Stark trap for about 6 hours. The solution is then allowed to cool and washed successively with sodium bicarbonate solution, water and brine. The organic layer is evaporated to dryness and the residue recrystallized from Skellysolve B to give 18.87 g. (93% yield) of 4-cyano-4-(4-fluorophenyl)cyclohexanone, ethylene ketal, having a melting point of 91° to 93°C.

Anal. Calcd. for $C_{15}H_{16}FNO_2$: C, 68.95; H, 6.17; N, 5.36. Found: C, 68.20; H, 6.02; N, 5.41.

Example 21
4-Cyano-4-(4-methoxyphenyl)cyclohexanone, ethylene ketal

A mixture of 22.43 g. (0.098 mole) of 4-cyano-4-methoxyphenyl)cyclohexanone (prepared in Example 15), 5.6 ml. [6.2 g. (0.1 mole)] of ethylene glycol and 0.24 g. of p-toluenesulfonic acid in 175 ml. of benzene is heated at reflux under a Dean-Stark trap for about 6 hours. The solution is then allowed to cool and washed successively with sodium bicarbonate solution, water and brine. The organic layer is evaporated to dryness and the residue recrystallized from a mixture of methylene chloride and Skellysolve B to give 24.66 g. (92.3% yield) of 4-cyano-4-(4-methoxyphenyl)cyclohexanone, ethylene ketal, having a melting point of 101° to 103°C.

Anal. Calcd. for $C_{16}H_{19}NO$: C, 70.31; H, 7.01; N, 5.13. Found: C, 70.20; H, 7.01; N, 5.02.

Example 22
4-Cyano-4-(3,4-dimethoxyphenyl)cyclohexanone, ethylene ketal

A mixture of 15.96 g. (0.062 mole) of 4-cyano-4-(3,4-dimethylphenyl)cyclohexanone (prepared in Example 16), 3.6 ml. (4 g. (0.064 mole)] of ethylene glycol and 0.16 g. of p-toluenesulfonic acid in 110 ml. of benzene is heated at reflux under a Dean-Stark trap for about 6 hours. The solution is then allowed to cool and washed successively with sodium bicarbonate solution, water and brine. The organic layer is evaporated to dryness and the residue recrystallized from ether to give 16.85 g. (90.3% yield) of 4-cyano-4-(3,4-dimethoxyphenyl)cyclohexanone, ethylene ketal, having a melting point of 93.5° to 96.5°C.

Anal. Calcd. for $C_{17}H_{21}NO_4$: C, 67.31; H, 6.98; N, 4.62. Found: C, 67.29; H, 7.01; N, 4.44.

Example 23 4-Cyano-4-(1-naphthyl)cyclohexanone, ethylene ketal

A mixture of 10.3 g. (0.041 mole) of 4-cyano-4-(1-naphthyl)cyclohexanone, 2.6 ml. [2.88 g. (0.047 mole)] of ethylene glycol and 0.25 g. of p-toluenesulfonic acid in 500 ml. of benzene is heated at reflux under a Dean-Stark trap for about 6 hours. The solution is then allowed to cool and washed successively with sodium bicarbonate solution, water and brine. The organic layer is evaporated to dryness and the residue recrystallized from a mixture of ethyl acetate and cyclohexane to give 11.21 g. (92% yield) of 4-cyano-4-(1-naphthyl)cyclohexanone, ethylene ketal having a melting point of 166° to 167°C.

Anal. Calcd. for $C_{19}H_{19}NO_2$: C, 77.79; H, 6.53; N, 4.77. Found: C, 77.33; H, 6.48; N, 4.74.

Following the procedure of Example 18 through 23 but substituting other 4-cyano-4-arylcyclohexanones (e.g., those prepared in the paragraph following Example 17) yields the corresponding ethylene ketals thereof.

Example 24 4-Carboxy-4-phenylcyclohexanone, ethylene ketal

A mixture of 11.27 g. (0.046 mole) of 4-cyano-4-phenylcyclohexanone, ethylene ketal (prepared in Example 18) and 11.3 g. of potassium hydroxide in 90 ml. of ethylene glycol is heated at reflux for about 16 hours. The resulting solution is allowed to cool, diluted with water and washed with ether. The aqueous layer was covered with ether and then cautiously acidified. The aqueous layer is extracted with two additional portions of ether and the extracts combined. The extracts are evaporated to dryness and the solid remaining is recrystallized from a mixture of ethylene chloride and Skellysolve B to give 10.51 g. (86.3% yield) of 4-carboxy-4-phenylcyclohexanone, ethylene ketal, having a melting point of 136° to 140°C.

Anal. Calcd. for $C_{15}H_{18}O_4$: C, 68.68; H, 6.92. Found: C, 68.27; H, 6.90.

Example 25
4-Carboxy-4-(4-chlorophenyl)cyclohexanone, ethylene ketal

A mixture of 21.87 g. (0.079 mole) of 4-cyano-4-(4-chlorophenyl)cyclohexanone, ethylene ketal (prepared in Example 19) and 22 g. of potassium hydroxide in 220 ml. of ethylene glycol is heated at reflux for about 16 hours. The resulting solution is allowed to cool, diluted with water and washed with ether. The aqueous layer is covered with ether and then cautiously acidified. The aqueous layer is extracted with two additional portions of ether and the extracts combined. The extracts are evaporated to dryness and the solid remaining is recrystallized from a mixture of ethylene chloride and Skellysolve B to give 19.26 g. (82.2% yield) of 4-carboxy-4-(4-chlorophenyl)cyclohexanone, ethylene ketal, having a melting point of 162.5° to 164.5°C.

Anal. Calcd. for $C_{15}H_{17}ClO_4$: C, 60.71; H, 5.78; Cl, 11.95. Found: C, 61.01; H, 5.77; Cl, 12.12.

Example 26
4-Carboxy-4-(4-fluorophenyl)cyclohexanone, ethylene ketal

A mixture of 18.17 g. (0.07 mole) of 4-cyano-4-(4-fluorophenyl)cyclohexanone, ethylene ketal (prepared in Example 20 and 15 g. of potassium hydroxide in 150 ml. of ethylene glycol is heated at reflux for about 16 hours. The resulting solution is allowed to cool, diluted with water and washed with ether. The aqueous layer is covered with ether and then cautiously acidified. The aqueous layer is extracted with two additional portions of ether and the extracts combined. The extracts are evaporated to dryness to give 18.2 g. (93% yield) of 4-carboxy-4-(4-fluorophenyl)cyclohexanone, ethylene ketal, having a melting point of 117° to 122°C.

Example 27
4-Carboxy-4-(4-methoxyphenyl)cyclohexanone, ethylene ketal

A mixture of 27.98 g. (0.103 mole) of 4-cyano-4-(4-methoxyphenyl)cyclohexanone ethylene ketal (prepared in Example 21) and 28 g. of potassium hydroxide in 280 ml. of ethylene glycol is heated at reflux for about 16 hours. The resulting solution is allowed to cool, diluted with water and washed with ether. The aqueous layer is covered with ether and then cautiously acidified. The aqueous layer is extracted with two additional portions of ether and the extracts combined. The extracts are evaporated to dryness and the solid remaining is recrystallized from a mixture of methylene chloride and Skellysolve B to give 22.35 g. (83.1% yield) of 4-carboxy-4-(4-methoxyphenyl)cyclohexanone, ethylene ketal, having a melting point of 154° to 155.5°C.

Anal. Calcd. for $C_{16}H_{20}O_5$: C, 65.74; H, 6.90. Found: C, 65.42; H, 6.93.

Example 28
4-Carboxy-4-(3,4-dimethoxyphenyl)cyclohexanone, ethylene ketal

A mixture of 17.54 g. (0.058 mole) of 4-cyano-4-(3,4-dimethoxy)cyclohexanone, ethylene ketal (prepared as in Example 22) and 17.5 g. of potassium hydroxide in 175 ml. of ethylene glycol is heated at reflux for about 16 hours. The resulting solution is allowed to cool, diluted with water and washed with ether. The aqueous layer is covered with ether and then cautiously acidified. The aqueous layer is extracted with two additional portions of ether and the extracts combined. The extracts are evaporated to dryness to give 19 g. (99% yield) of 4-carboxy-4-(3,4-dimethoxyphenyl)cyclohexanone, ethylene ketal, as an amorphous gum.

Example 29 4-Carboxy-4-(1-naphthyl)cyclohexanone, ethylene ketal

A mixture of 11.21 g. (0.039 mole) of 4-cyano-4-(1-naphthyl)cyclohexanone, ethylene ketal (prepared in Example 23) and 12 g. of potassium hydroxide in 60 ml. of ethylene glycol is heated at reflux for about 16 hours. The resulting solution is allowed to cool, diluted with water and washed with ether. The aqueous layer is covered with ether and then cautiously acidified. The aqueous layer is extracted with two additional portions of ether and the extracts combined. The extracts are evaporated to dryness and the solid remaining is recrystallized from a mixture of ethyl acetate and cyclohexane to give 3.84 g. (31.5% yield) of 4-carboxy-4-(1-naphthyl)cyclohexanone, ethylene ketal, having a melting point of 174° to 177°C.

Anal. Calcd. for $C_{19}H_{20}O_4$: C, 73.06; H, 6.45. Found: C, 72.58; H, 6.49.

Following the procedure of Examples 24 through 29 but substituting other 4-cyano-4-arylcyclohexanone, ethylene ketals as starting materials, such as 1. 4-cyano-4-(3-bromophenyl)cyclohexanone, ethylene ketal,
2. 4-cyano-4-(2-bromo-4-ethylphenyl)cyclohexanone, ethylene ketal,
3. 4-cyano-4-(3-fluoro-5-ethylthiophenyl)cyclohexanone, ethylene ketal,
4. 4-cyano-4-(2,5-dimethoxyphenyl)cyclohexanone, ethylene ketal,
5. 4-cyano-4-(3,6-dipropylphenyl)cyclohexanone, ethylene ketal,
6. 4-cyano-4-(2-ethyl-3-fluoro-5-methylphenyl)cyclohexanone, ethylene ketal,
7. 4-cyano-4-(2-chloro-6-ethylphenyl)cyclohexanone, ethylene ketal,
8. 4-cyano-4-[3-methoxy-5-propyl-(2-naphthyl)]cyclohexanone, ethylene ketal,
9. 4-cyano-4-[(o-1-naphthylphenyl)]cyclohexanone, ethylene ketal, and the like, yields, respectively, 1. 4-carboxy-4-(3-bromophenyl)cyclohexanone, ethylene ketal,
2. 4-carboxy-4-(2-bromo-4-ethylphenyl)cyclohexanone, ethylene ketal,
3. 4-carboxy-4-(3-fluoro-5-ethylthiophenyl)cyclohexanone, ethylene ketal,
4. 4-carboxy-4-(2,5-dimethoxyphenyl)cyclohexanone, ethylene ketal,
5. 4-carboxy-4-(3,6-dipropylphenyl)cyclohexanone, ethylene ketal,
6. 4-carboxy-4-(2-ethyl-3-fluoro-5-methylphenyl)cyclohexanone, ethylene ketal,
7. 4-carboxy-4-(2-chloro-6-ethylphenyl)cyclohexanone, ethylene ketal,
8. 4-carboxy-4-[3-methoxy-5-propyl(2-naphthyl)-]cyclohexanone, ethylene ketal,
9. 4-carboxy-4-[(o-1-naphthylphenyl)]cyclohexanone, ethylene ketal, and the like.

Example 30 4-Formyl-4-phenylcyclohexanone, ethylene ketal

To a well stirred suspension of 2.74 g. (0.072 mole) of lithium aluminum hydride in 170 ml. of tetrahydrofuran, a solution of 34.8 g. (0.143 mole) of 4-cyano-4-phenylcyclohexanone, ethylene ketal in 1700 ml. of tetrahydrofuran is added in a period of about 20 minutes. The mixture is stirred at room temperature for about 1.75 hours, then cooled in an icebath and treated successively with 2.8 ml. of water, 2.8 ml. of 15% sodium hydroxide solution and 8.2 ml. of water. The resulting inorganic gel is collected on a filter and rinsed with ether. The combined filtrates are then evaporated to dryness. A solution of the residue in 525 ml. of tetrahydrofuran and 52.5 ml. of 2.5 N hydrochloric acid is stirred at room temperature for about 15 minutes, treated with 17 g. of sodium bicarbonate solution and then evaporated to dryness. Ether is added to the residue and the organic layer evaporated to dryness to yield 34.07 g. (96.7% yield) of crude 4-formyl-4-phenylcyclohexanone, ethylene ketal, having a melting point of 51° to 66°C. Its infrared (IR) and NMR confirm its expected structure.

Following the procedure of Example 30 but substituting other 4-cyano-4-arylcyclohexanone, ethylene ketals (e.g., those employed as starting materials in the paragraph following Example 29) yields the corresponding 4-formyl counterparts thereof.

Example 31 4-Methyl-4-phenylcyclohexanone, ethylene ketal

A mixture of 9.3 g. (0.038 mole) of 4-formyl-4-phenyl cyclohexanone, ethylene ketal (prepared in Example 30), 5 ml. of hydrazine hydrate and 6.4 g. of potassium hydroxide in 120 ml. of ethylene glycol is heated at reflux for about 1 hour. The solvent is then allowed to distill until the pot temperature comes to about 200°C. After about 5 hours the mixture is allowed to cool and then diluted with water and brine and evaporated to dryness. The residue is chromatographed on 750 ml. of Florisil (magnesium silicate) with elution by 1% ethyl acetate in Skellysolve B. The crystalline fractions are combined and recrystallized from a mixture of methanol and water to give 5.92 g. (67% yield) of 4-methyl-4-phenylcyclohexanone, ethylene ketal, having a melting point of 48° to 50°C.

Anal. Calcd. for $C_{15}H_{20}O_2$: C, 77.54; H, 8.68. Found: C, 77.79; H, 8.87.

Following the procedure of Example 31 but substituting other 4-formyl-4-arylcyclohexanones, ethylene ketals as starting materials, such as 1. 4-formyl-4-(2-chloro-6-methylphenyl)cyclohexanone, ethylene ketal,
2. 4-formyl-4-(3-fluoro-6-methoxyphenyl)cyclohexanone, ethylene ketal,
3. 4-formyl-4-(3,5-dimethylthiophenyl)cyclohexanone, ethylene ketal,
4. 4-formyl-4-(2-bromo-4-fluoro-6-propylphenyl)cyclohexanone, ethylene ketal,
5. 4-formyl-4-[2-ethoxy-4-fluoro-(3-naphthyl)]cyclohexanone, ethylene ketal,
6. 4-formyl-4-[(m-2-naphthylphenyl)]cyclohexanone, ethylene ketal, and the like, yields, respectively, 1. 4-methyl-4-(2-chloro-6-methylphenyl)cyclohexanone, ethylene ketal,
2. 4-methyl-4-(3-fluoro- 6-methoxyphenyl)cyclohexanone, ethylene ketal,
3. 4-methyl-4-(3,-dimethylthiophenyl)cyclohexanone, ethylene ketal,
4. 4-methyl-4-(2-bromo-4-fluoro-6-propylphenyl)cyclohexanone, ethylene ketal,
5. 4-methyl-4-[2-ethoxy-4-fluoro-(3-naphthyl)]cyclohexanone, ethylene ketal,
6. 4-methyl-4-[(m-2-naphthylphenyl)]cyclohexanone, ethylene ketal, and the like.

Example 32
4-Hydroxymethyl-4-phenylcyclohexanone, ethylene ketal

A solution of 10.51 g. (0.040 mole) of 4-carboxy-4-phenylcyclohexanone, ethylene ketal (prepared in Example 24) in 200 ml. of tetrahydrofuran is added to 3.6 g. (0.095 mole) of lithium aluminum hydride in 53 ml. of tetrahydrofuran. Following about 6 hours of heating at reflux, the mixture is cooled in ice and treated successively with 3.6 ml. of water, 3.6 ml. of 15% sodium hydroxide solution and 10.8 ml. of water. The resulting inorganic gel is collected on a filter and rinsed with ether. The combined filtrates are evaporated to dryness and the residue is recrystallized from a mixture of ethyl acetate and cyclohexane to give 8.94 g. of 4-hydroxymethyl-4-phenylcyclohexanone, ethylene ketal, having a melting point of 120° to 122° C.

Anal. Calcd. for $C_{15}H_{20}O_3$: C, 72.55; H, 8.12. Found: C, 72.53; H, 8.15.

Example 33
4-Hydroxymethyl-4-(4-flurophenyl)cyclohexanone, ethylene ketal A solution of 18.2 g. (0.065 mole) of 4-carboxy-4-(4-fluorophenyl)cyclohexanone, ethylene ketal (prepared in Example 26) in 200 ml. of tetrahydrofuran is added to 5.9 g. (0.155 mole) of lithium aluminum hydride in 50 ml. of tetrahydrofuran. Following about 6 hours of heating at reflux, the mixture is cooled in ice and treated with 10 ml. of water and 200 ml. of 2.5 N hydrochloric acid. The organic layer is washed with water and brine and then evaporated to dryness to give 18.18 g. (99% yield) of 4-hydroxymethyl-4-(4-fluorophenyl)-cyclohexanone, ethylene ketal as an amorphour gum.

Example 34
4-Hydroxymethyl-4-(4-chlorophenyl)cyclohexanone, ethylene ketal A solution of 19.26 g. (0.065 mole) of 4-carboxy-4-(4-chlorophenyl)cyclohexanone, ethylene ketal (prepared in Example 25) in 320 ml. of tetrahydrofuran is added to 5.9 g. (0.155 mole) of lithium aluminum hydride in 85 ml. of tetrahydrofuran. Following about 6 hours of heating at reflux, the mixture is cooled in ice and treated successively with 6 ml. of water, 6 ml. of 15% sodium hydroxide solution and 18 ml. of water. The resulting inorganic gel is collected on a filter and rinsed with ether. The combined filtrates are evaporated to dryness to give 19.23 g. (99% yield) of 4-hydroxymethyl-4-(4-chlorophenyl)cyclohexanone, ethylene ketal as an amorphous gum.

Example 35
4-hydroxymethyl-4-(4-methoxyphenyl)cyclohexanone, ethylene ketal A solution of 11.2 g. (0.038 mole) of 4-carboxy-4-(4-methoxyphenyl)cyclohexanone, ethylene ketal (prepared as in Example 27) in 190 ml. of tetrahydrofuran is added to 3.5 g. (0.092 mole) of lithium aluminum hydride in 50 ml. of tetrahydrofuran. Following about 6 hours of heating at reflux, the mixture is cooled in ice and treated successively with 3.5 ml. of water, 3.5 ml. of 15% sodium hydroxide solution and 10.5 ml. of water. The resulting inorganic gel is collected on a filter and rinsed with ether. The combined filtrates are evaporated to dryness and the residue recrystallized from a mixture of methylene chloride and Skellysolve B to give 16.87 g. of 4-hydroxymethyl-4-(4-methoxyphenyl)cyclohexanone, ethylene ketal, having a melting point of 96° to 98°C.

Anal. Calcd. for $C_{16}H_{22}O_4$: C, 69.04; H, 7.97. Found: C, 68.86; H, 7.79.

Example 36
4-Hydroxymethyl-4-(3,4-dimethoxyphenyl)cyclohexanone, ethylene ketal A solution of 19 g. (0.059 mole) of 4-carboxy-4-(3,4-dimethoxyphenyl)cyclohexanone, ethylene ketal (prepared in Example 28) in 290 ml. of tetrahydrofuran is added to 5.35 g. (0.141 mole) lithium aluminum hydride in 80 ml. of tetrahydrofuran. Following about 6 hours of heating at reflux the mixture is cooled in ice and treated successively with 5.4 ml. of water, 5.4 ml. of 15% sodium hydroxide solution and 16.2 ml. of water. The resulting inorganic gel is collected on a filter and rinsed with ether. The combined filtrates are evaporated to dryness to give 11.4 g. (62.7% yield) of 4-hydroxymethyl-4-(3,4-dimethoxyphenyl)-cyclohexanone, ethylene ketal as an amorphous gum.

Example 37
4-Hydroxymethyl-4-(1-naphthyl)cyclohexanone, ethylene ketal

A solution of 3.84 g. (0.0123 mole) of 4-carboxy-4-(1-naphthyl)cyclohexanone, ethylene ketal (prepared in Example 29) in 80 ml. of tetrahydrofuran is added to 0.5 g. (0.013 mole) of lithium aluminum hydride in 10 ml. of tetrahydrofuran. Following about 6 hours of heating at reflux the mixture is cooled in ice and treated successively with 0.5 ml. of water, 0.5 ml. of 15% sodium hydroxide solution and 1.5 ml. of water. The resulting inorganic gel is collected on a filter and rinsed with ether. The combined filtrates are evaporated to dryness to give 3.95 g. (99% yield) of 4-hydroxymethyl-4-(1-naphthyl)cyclohexanone, ethylene ketal as an amorphous gum.

Following the procedure of Examples 33 through 37 but substituting other 4-carboxy-4-arylcyclohexanone, ethylene ketals as starting materials, such as 1. 4-carboxy-4-(3-bromo-6-ethylphenyl)cyclohexanone, ethylene ketal,
2. 4-carboxy-4-(2-chloro-3-ethyl-5-methoxyphenyl)-cyclohexanone, ethylene ketal,
3. 4-carboxy-4-[2-ethylthio-3-fluoro-(4-naphthyl)]-cyclohexanone, ethylene ketal,
4. 4-carboxy-4-[(p-3-naphthylphenyl)]cyclohexanone; ethylene ketal, and the like, yields, respectively, 1. 4-hydroxymethyl-4-(3-bromo-6-ethylphenyl)cyclohexanone, ethylene ketal,
2. 4-hydroxymethyl-4-(2-chloro-3-ethyl-5-methoxyphenyl)cyclohexanone, ethylene ketal,
3. 4-hydroxymethyl-4-[2-ethylthio-4-fluoro-(4-naphthyl)]cyclohexanone, ethylene ketal,
4. 4-hydroxymethyl-4-[(p-3-naphthylphenyl)]cyclohexanone, ethylene ketal, and the like.

Example 38 4-Acetoxymethyl-4-phenylcyclohexanone

A solution of 14.16 g. (0.057 mole) of 4-hydroxymethyl-4-phenylcyclohexanone, ethylene ketal (prepared as in Example 32) and 6.5 ml. of 2.5 N hydrochloric acid in 260 ml. of acetone is stirred at room temperature for about 20 hours. Most of the solvent is then removed under vacuum and the residue taken up in water and ether. The organic layer is washed successively with sodium bicarbonate solution, water and brine and evaporated to dryness. The residue is recrystallized from ether to yield 4.92 g. of 4-hydroxymethyl-4-phenylcyclohexanone, having a melting point of 53° to 58°C.

6.6 g. of 4-hydroxymethyl-4-phenylcyclohexanone is dissolved in 40 ml. of pyridine and 20 ml. acetic anhydride. After about 20 hours of standing at room temperature, the mixture is poured into ice and water. The gum that precipitates is extracted with ether. The organic layer is washed successively with water, 2.5 N hydrochloric acid, water, sodium bicarbonate solution, and brine, and then evaporated to dryness. The solid residue is recrystallized from Skellysolve B to give 6.74 g. (35.8% yield) of 4-acetoxymethyl-4-phenylcyclohexanone, having a melting point of 74° to 79°C.

Anal. Calcd. for $C_{15}H_{18}O_3$: C, 73.14; H, 7.37. Found: C, 72.56; H, 7.32.

Example 39
4-Acetoxymethyl-4-(4-chlorophenyl)cyclohexanone

A solution of 19.23 g. (0.068 mole) of 4-hydroxymethyl-4-(4-chlorophenyl)cyclohexanone, ethylene ketal (prepared in Example 34) and 20 ml. of 2.5 N hydrochloric acid in 200 ml. of acetone is stirred at room temperature for about 20 hours. Most of the solvent is then removed under vacuum and the residue taken up in water and ether. The organic layer is washed successively with sodium bicarbonate solution, water and brine and evaporated to dryness, to give 4-hydroxymethyl-4-(4-chlorophenyl)cyclohexanone.

The 4-hydroxymethyl-4-(4-chlorophenyl)cyclohexanone is dissolved in 60 ml. of pyridine and 30 ml. of acetic anhydride. After about 20 hours of standing at room temperature, the mixture is poured into ice and water. The gum that precipitates is extracted with ether. The organic layer is washed successively with water, 2.5 N hydrochloric acid, water, sodium bicarbonate solution and brine, and evaporated to dryness to give 12.8 g. (66% yield) of 4-acetoxymethyl-4-(4-chlorophenyl)cyclohexanone, as an amorphous gum.

Example 40
4-Acetoxymethyl-4-(4-fluorophenyl)cyclohexanone

A solution of 18.18 g. (0.068 mole) of 4-hydroxymethyl-4-(4-fluorophenyl)cyclohexanone, ethylene ketal (prepared in Example 33) and 20 ml. of 2.5 N hydrochloric acid in 200 ml. of acetone is stirred at room temperature for about 20 hours. Most of the solvent is removed under vacuum and the residue taken up in water and ether. The organic layer is washed successively with sodium bicarbonate solution, water and brine and evaporated to dryness to give 4-hydroxymethyl-4-(4-fluorophenyl)cyclohexanone.

The 4-hydroxymethyl-4-(4-fluorophenyl)cyclohexanone is dissolved in 50 ml. of pyridine and 30 ml. of acetic anhydride. After about 20 hours of standing at room temperature, the mixture is pured into ice and water. The gum that precipitates is extracted with ether. The organic layer is washed sucessively with water, 2.5 N hydrochloric acid, water, sodium bicarbonate solution and brine, and evaporated to dryness. The solid residue is recrystallized from ether to give 9.77 g. (57% yield) of 4-acetoxymethyl-4-(4-fluorophenyl)cyclohexanone, having a melting point of 80° to 84°C.

Anal. Calcd. for $C_{15}H_{17}FO_3$: C, 68.00; H, 6.69. Found: C, 68.17; H, 6.49.

Example 41
4-acetoxy-4-(4-methoxyphenyl)cyclohexanone

A solution of 5 g. (0.018 mole) of 4-hydroxymethyl-4-(4-methoxyphenyl)cyclohexanone, ethylene ketal (prepared as in Example 35) and 5 ml. of 2.5 N hydrochloric acid in 50 ml. of acetone is stirred at room temperature for about 20 hours. Most of the solvent is removed under vacuum and the residue taken up in water and ether. The organic layer is washed sucessively with sodium bicarbonate solution, water and brine and evaporated to dryness to give 4-hydroxymethyl-4-(4-methoxyphenyl)cyclohexanone.

The 4-hydroxymethyl-4-(4-methoxyphenyl)cyclohexanone is dissolved in 12 ml. of pyridine and 6 ml. of acetic anhydride. After about 20 hours of standing at room temperature, the mixture is poured into ice and water. The gum that precipitates is extracted with ether. The organic layer is washed successively with water, 2.5 N hydrochloric acid, water, sodium bicarbonate solution and brine, and evaporated to dryness. The solid residue is recrystallized from a mixture of ether and Skellysolve B to give 2.95 g. (68% yield) of 4-acetoxymethyl-4-(4-methoxyphenyl)cyclohexanone, having a melting point of 86.5° to 88°C.

Anal. Calcd. for $C_{16}H_{20}O_4$: C, 69.54; H, 7.30. Found: C, 69.22; H, 7.55.

Example 42
4-Acetoxymethyl-4-(3,4-dimethoxyphenyl)cyclohexanone

A solution of 11.4 g. (0.037 mole) of 4-hydroxymethyl-4-(3,4-dimethoxyphenyl)cyclohexanone, ethylene ketal (prepared in Example 36) and 11 ml. of 2.5 N hydrochloric acid in 110 ml. of acetone is stirred at room temperature for about 20 hours. Most of the solvent is removed under vacuum and the residue taken up in water and ether. The organic layer is washed successively with sodium bicarbonate solution, water and brine and evaporated to dryness, to give 4-hydroxymethyl-4-(3,4-dimethoxyphenyl)cyclohexanone.

The 4-hydroxymethyl-4-(3,4-dimethoxyphenyl)cyclohexanone is dissolved in 20 ml. of pyridine and 10 ml. of acetic anhydride. After about 20 hours of standing at room temperature, the mixture is poured into ice and water. The gum that precipitates is extracted with ether. The organic layer is washed successively with water, 2.5 N hydrochloric acid, water and brine, and evaporated to dryness to give 6.43 g. (57% yield) of 4-acetoxymethyl-4-(3,4-dimethoxyphenyl)cyclohexanone, as an amorphous gum.

Example 43
4-Acetoxymethyl-4-(1-naphthyl)cyclohexanone

A solution of 8.81 g. (0.03 mole) of 4-hydroxymethyl-4-(1-naphthyl)cyclohexanone, ethylene ketal (prepared as in Example 37) and 10 ml. of 2.5 N hydrochloric acid in 100 ml. of acetone is stirred at room temperature for about 20 hours. Most of the solvent is removed under vacuum and the residue taken up in water and ether. The organic layer is washed successively with sodium bicarbonate solution, water and brine and evaporated to dryness to give 4-hydroxymethyl-4-(1-naphthyl)cyclohexanone.

The 4-hydroxymethyl-4-(1-naphthyl)cyclohexanone is dissolved in 30 ml. of pyridine and 15 ml. of acetic anhydride. After about 20 hours of standing at room temperature, the mixture is poured in ice and water. The gum that precipitates is extracted with ether. The organic layer is washed successively with water, 2.5 N hydrochloric acid, water, sodium bicarbonate solution and brine, and evaporated to dryness. The solid residue is recrystallized from wet ether to give 3.66 g. (40% yield) of 4-acetoxymethyl-4-(1-naphthyl)cyclohexanine, having a melting point of 63° to 66°C.

Anal. Calcd. for $C_{19}H_{20}O_3 \cdot \frac{1}{2}H_2O$: C, 74.73; H, 6.93. Found: C, 74.94; H, 7.06.

Following the procedure of Example 38 through 43 but substituting other 4-hydroxymethyl-4-arylcyclohexanone, ethylene ketals as starting materials, such as 1. 4-hydroxymethyl-4-(3-bromo-5-methylphenyl)cyclohexanone, ethylene ketal,
2. 4-hydroxymethyl-4-(2-fluoro-6-methoxyphenyl)cyclohexanone, ethylene ketal,
3. 4-hydroxymethyl-4-(2,6-diethoxyphenyl)cyclohexanone, ethylene ketal,
4. 4-hydroxymethyl-4-(2-ethyl-5-propylphenyl)cyclohexanone, ethylene ketal,
5. 4-hydroxymethyl-4-(2-chloro-4-ethylthio-6-methoxyphenyl)cyclohexanone, ethylene ketal,
6. 4-hydroxymethyl-4-[3-ethoxy-5-fluoro(7-naphthyl)]-cyclohexanone, ethylene ketal,
7. 4-hydroxymethyl-4-[(p-1-naphthylphenyl)]cyclohexanone, ethylene ketal, and the like, yields, respectively,
1. 4-acetoxymethyl-4-(3-bromo-5-methylphenyl)cyclohexanone,
2. 4-acetoxymethyl-4-(2-fluoro-6-methoxyphenyl)cyclohexanone,
3. 4-acetoxymethyl-4-(2,6-diethoxyphenyl)cyclohexanone,
4. 4-acetoxymethyl-4-(2-ethyl-5-propylphenyl)cyclohexanone,
5. 4-acetoxymethyl-4-(2-chloro-4-ethylthio-6-methoxyphenyl)cyclohexanone,
6. 4-acetoxymethyl-4-[3-ethoxy-5-fluoro-(7-naphthyl)]-cyclohexanone,
7. 4-acetoxymethyl-4-[(p-1-naphthylphenyl)]cyclohexanone, and the like.

Following the procedure of the immediately preceeding paragraph and of Examples 38 through 43 but substituting propionic anhydride for acetic anhydride, yields the corresponding 4-propionyloxymethyl-4-arylcyclohexanones.

Example 44
4-cis-Acetoxymethyl-4-trans-phenylcyclohexanol and 4-trans-acetoxymethyl-4-cis-phenylcyclohexanol To a solution of 3.62 g. (0.0147 mole) of 4-acetoxymethyl-4-phenylcyclohexanone (prepared as in Example 38) in 50 ml. of 95% isopropanol, 0.25 g. of sodium borohydride is added. At the end of about 2 hours most of the solvent is removed under vacuum. The precipitates gum is taken up in ether and the organic layer washed successively with water and brine and then evaporated to dryness. The residue is chromatographed on a silica gel column with elution by 5% acetone in methylene chloride. The fractions that are the same by thin layer chromatography (TLC) are combined to give the first isomer, which is recrystallized from petroleum ether to give 2.12 g. (58% yield) of solid 4-cis-acetoxymethyl-4-trans-phenylcyclohexanol, having a melting point of 69° to 71.5°C.

The second isomer is obtained from pooled fractions eluted from the column and shown to be the same by TLC. The product is recrystallized from petroleum ether to give 0.49 g. (13% yield) of 4-trans-acetoxymethyl-4-cis-phenylcyclohexanol, having a melting point of 60° to 63°C.

Example 45
4-cis-Acetoxymethyl-4-trans-(4-chlorophenyl)-cyclohexanol and 4-trans-acetoxymethyl-4-cis-(4-chlorophenyl)cyclohexanol To a solution of 16.09 g. (0.057 mole) of 4-acetoxymethyl-4-(4-chlorophenyl)cyclohexanone (prepared as in Example 39) in 155 ml. of 95% isopropanol, 2.2 g. of sodium borohydride is added. After about 2 hours of stirring at room temperature most of the solvent is removed under vacuum. The residue is then taken up in ether and water. The organic layer is washed successively with water and brine and then evaporated to dryness. The residue is chromatographed on a column of 2000 ml. of silica gel with elution by 5% acetone in methylene chloride. The fractions shown by TLC to consist of the less polar product are combined and recrystallized from a mixture of ether and Skellysolve B to give 6.34 g. (39.3% yield) of 4-cis-acetoxymethyl-4-trans-(4-chlorophenyl)cyclohexanol, having a melting point of 105° to 107°C.

Anal. Calcd. for $C_{15}H_{19}ClO_3$: C, 63.71; H, 6.77; Cl, 12.54. Found: C, 63.85; H, 6.80; Cl, 12.62.

The second and more polar isomer is obtained from pooled fractions eluted from the column. The product is recrystallized from a mixture of ether and Skellysolve B to give 4-trans-acetoxymethyl-4-cis-(4-chlorophenyl)cyclohexanol.

Example 46
4-cis-Acetoxymethyl-4-trans-(4-fluorophenyl)-cyclohexanol and 4-trans-acetoxymethyl-4-cis-(4-fluorophenyl)cyclohexanol To a solution of 9.77 g. (0.037 mole) of 4-acetoxymethyl-4-(4-fluorophenyl)cyclohexanone (prepared in Example 40) in 100 ml. of 95% isopropanol, 1.42 g. of sodium borohydride is added. After about 2 hours of stirring at room temperature most of the solvent is removed under vacuum. The residue is then taken up in ether and water. The organic layer is washed successively with water and brine and then evaporated to dryness. The residue is chromatographed on a column of 1000 ml. of silica gel with elution by 10% acetone in methylene chloride. The fractions shown by TLC to consist of the less polar product are combined and recrystallized from a mixture of ether and Skellysolve B to give 4.55 g. (46% yield) of 4-cis-acetoxymethyl-4-trans-(4-fluorophenyl)cyclohexanol, having a melting point of 80° to 82.5°C.

Anal. Calcd. for $C_{15}H_{19}FO_3$: C, 67.65; H, 7.19. Found: C, 67.78; H, 7.55.

The second and more polar isomer is obtained from pooled fractions eluted from the column. The product is recrystallized from a mixture of ether and Skellysolve B to give 4-trans-acetoxymethyl-4-cis-(4-fluorophenyl)cyclohexanol.

Example 47
4-cis-Acetoxymethyl-4-trans-(4-methoxyphenyl)cyclohexanol and 4-trans-acetoxymethyl-4-cis-(4-methoxyphenyl)cyclohexanol To a solution of 6.86 g. of 4-acetoxymethyl-4-(4-methoxyphenyl)cyclohexanone (prepared as in Example 41) in 80 ml. of 95% isopropanol, 0.42 g. of sodium borohydride is added. After about 2 hours of stirring at room temperature most of the solvent is removed under vacuum. The residue is then taken up in ether and water. The organic layer is washed successively with water and brine and then evaporated to dryness. The residue is chromatographed on a column of 525 ml. of Florisil with elution of 15% acetone in Skellysolve B. The fractions shown by TLC to consist of the less polar product are combined and recrystallized from a mixture of ether and petroleum ether to give 4.4 g. (44.8% yield) of 4-cis-acetoxymethyl-4-trans-(4-methoxyphenyl) cyclohexanol, having a melting point of 90° to 92.5°C.

Anal. Calcd. for $C_{16}H_{22}O_4$: C, 69.04; H, 7.97. Found: C, 68.90; H, 7.56.

The second and more polar isomer is obtained from pooled fractions eluted from the column. The product is recrystallized from a mixture of ether and petroleum ether to give 4-trans-acetoxymethyl-4-cis-(4-methoxyphenyl)cyclohexanol.

Example 48
4-cis-Acetoxymethyl-4-trans-(3,4-dimethoxyphenyl)-cyclohexanol and
4-trans-acetoxymethyl-4-cis-(3,4-dimethoxyphenyl)cyclohexanol To a solution of 6.43 g. (0.021 mole) of 4-acetoxymethyl-4-(3,4-dimethoxyphenyl)cyclohexanone (prepared in Example 42) in 57 ml. of 95% isopropanol, 0.81 g. of sodium borohydride is added. After about 2 hours of stirring at room temperature most of the solvent is removed under vacuum. The residue is then taken up in ether and water. The organic layer is washed successively with water and brine and then evaporated to dryness. The residue is chromatographed on a column of 500 ml. of silica gel with elution by 5% acetone in methylene chloride. The fractions shown by TLC to consist of the less polar product are combined to give 1.54 g. (28.3% yield) of 4-cis-acetoxymethyl-4-trans-(3,4-dimethoxyphenyl)cyclohexanol, as an amorphous gum.

The second and more polar isomer, 4-trans-acetoxymethyl-4-cis (3,4-dimethoxyphenyl)cyclohexanol, is obtained from pooled fractions eluted from the column shown to be the same by TLC.

Example 49
4-cis-Acetoxymethyl-4-trans-(1-naphthyl)cyclohexanol and
4-trans-acetoxymethyl-4-cis-(1-naphthyl)cyclohexanol To a solution 3.66 g. (0.012 mole) of 4-acetoxymethyl-4-(1-naphthyl)cyclohexanone (prepared in Example 43) in 75 ml. of ethanol, 0.5 g. of sodium borohydride is added. After about 2 hours of stirring at room temperature most of the solvent is removed under vacuum. The residue is then taken up in ether and water. The organic layer is washed successively with water and brine and then evaporated to dryness. The residue is chromatographed on a column of 400 ml. of silica gel with elution by 10% acetone in Skellysolve B. The fractions shown by TLC to consist of the less polar product are combined to give 1.92 g. (53.6% yield) of 4-cis-acetoxymethyl-4-trans-(1-naphthyl)cyclohexanol, as an amorphous gum.

The second and more polar isomer, 4-trans-acetoxymethyl-4-cis-(1-naphthyl)cyclohexanol, is obtained from pooled fractions eluted from the column.

Following the procedures of Examples 44 through 49 but substituting 4-propionyloxymethyl-4-arylcyclohexanones as starting materials, yields the corresponding 4-cis-propionyloxymethyl-4-trans-arylcyclohexanols and 4-trans-propionyloxymethyl-4-cis-arylcyclohexanols.

Following the procedures of the immediately preceding paragraph and of Examples 44 through 49 but substituting other starting materials, such as
1. 4-acetoxymethyl-4-(3-bromophenyl)cyclohexanone,
2. 4-propionyloxymethyl-4-(3-chloro-5-methylphenyl)-cyclohexanone,
3. 4-acetoxymethyl-4-(2-chloro-4-fluoro-6-methoxyphenyl)cyclohexanone,
4. 4-propionyloxymethyl-4-(2,4-dipropoxyphenyl)-cyclohexanone,
5. 4-acetoxymethyl-4-(3-methyl-5-propylphenyl)cyclohexanone,
6. 4-acetoxymethyl-4-(2-chloro-4-ethoxy-6-methylphenyl)cyclohexanone,
7. 4-acetoxymethyl-4-[α-(2-chloro-5-ethylphenyl)-cyclopentyl]cyclohexanone,
8. 4-propionyloxymethyl-4-[2-ethylthio-4-fluoro-(5-naphthyl)]cyclohexanone,
9. 4-acetoxymethyl-4-[(p-4-naphthylphenyl)]cyclohexanone, and the like, yields, respectively,
1. 4-cis (and trans)-acetoxymethyl-4-trans (and cis)-(3-bromophenyl)cyclohexanol,
2. 4-cis (and trans)-propionyloxymethyl-4-trans (and cis)-(3-chloro-5-methylphenyl)cyclohexanol,
3. 4-cis (and trans)-acetoxymethyl-4-trans (and cis)-(2-chloro-4-fluoro-6-methoxyphenyl)cyclohexanol,
4. 4-cis (and trans)-propionyloxymethyl-4-trans (and cis)-(2,4-dipropoxyphenyl)cyclohexanol,
5. 4-cis (and trans)-acetoxymethyl-4-trans (and cis)-(3-methyl-5-propylphenyl)cyclohexanol,
6. 4-cis (and trans)-acetoxymethyl-4-trans (and cis)-(2-chloro-4-ethoxy-6-methylphenyl)cyclohexanol,
7. 4-cis (and trans)-acetoxymethyl-4-trans (and cis)-[α-(2-chloro-5-ethylphenyl)cyclopentyl]cyclohexanol,
8. 4-cis (and trans)-propionyloxymethyl-4-trans (and cis)-[2-ethylthio-4-fluoro-(5-naphthyl]cyclohexanol,
9. 4-cis (and trans)-acetoxymethyl-4-trans (and cis)-[(p-4-naphthylphenyl)]cyclohexanol, and the like.

Example 50 4-cis-Methyl-4-trans-phenylcyclohexanol and 4-trans-methyl-4-cis-phenylcyclohexanol A solution of 5.92 g. (0.0253 mole) of 4-methyl-4-phenylcyclohexanone, ethylene ketal (prepared in Example 31) and 6 ml. of 2.5 N hydrochloric acid in 60 ml. of acetone is stirred at room temperature for about 20 hours. The solvent is removed under vacuum and the residue dissolved in ether and water. The organic layer is washed successively with sodium bicarbonate solution and brine and then evaporated to dryness to give 4-methyl-4-phenylcyclohexanone as an oil.

To a solution of the oily 4-methyl-4-phenylcyclohexanone in 50 ml. of ethanol, 1.25 g. of sodium borohydride is added. At the end of about 5 hours the solvent is removed and then dissolved in ether and water. The organic layer is washed successively with sodium bicarbonate solution and brine and then evaporated to dryness. The crude product is chromatographed on a column of 500 ml. of silica gel with elution by 1% acetone in methylene chloride. There is first obtained 1.4 g. of the starting ethylene ketal having a melting point of 44° to 48°C., followed by 3.08 g. (79% yield) of 4-methyl-4-phenylcyclohexanol, having a melting point of 56° to 72°C. The NMR of the 4-methyl-4-phenylcyclohexanol shows a 3:2 ratio of equatorial to axial compounds. Separation of the mixture by additional chromatography yields 4-cis-methyl-4-trans-phenylcyclohexanol and 4-trans-methyl-4-cis-phenylcyclohexanol.

Following the procedure of Example 50 but substituting other 4-methyl-4-arylcylohexanone, ethylene ketals, such as 1. 4-methyl-4-(2-bromo-6-ethylphenyl)cyclohexanone, ethylene ketal,
2. 4-methyl-4-(3-chloro-5-ethoxyphenyl)cyclohexanone, ethylene ketal,
3. 4-methyl-4-(2-chloro-4-fluoro-6-methylthiophenyl)cyclohexanone, ethylene ketal,
4. 4-methyl-4-[2-fluoro-5-methoxy(2-naphthyl)]cyclohexanone, ethylene ketal, and the like,
yields, respectively,
1. 4-cis (and trans)-methyl-4-trans (and cis)-(2-bromo-6-ethylphenyl)cyclohexanol,
2. 4-cis (and trans)-methyl-4-trans (and cis)-(3-chloro-5-ethoxyphenyl)cyclohexanol,
3. 4-cis (and trans)-methyl-4-trans (and cis)-(2-chloro-4-fluoro-6-methylthiophenol)cyclohexanol,
4. 4-cis (and trans)-methyl-4-trans (and cis)-[2-fluoro-5-methoxy-(2-naphthyl)]cyclohexanol, and the like.

Example 51
4-cis-Acetoxymethyl-4-trans-phenylcyclohexanol, methanesulfonate

A solution of 18.88 g. of 4-cis-acetoxymethyl-4-trans-phenylcyclohexanol (prepared as in Example 44) in 190 ml. of pyridine is cooled in ice. To this solution, 1.9 ml. of methanesulfonyl chloride is cautiously added. After standing for about 18 hours in the cold, the mixture is poured onto ice and water. The gum that precipitates is extracted with ether. The organic layer is washed successively with water, 2.5 N hydrochloric acid, water and brine and then evaporated to dryness. The residue is recrystallized from a mixture of ether and petroleum ether to give 21.07 g. (81.5% yield) of 4-cis-acetoxymethyl-4-trans-phenylcyclohexanol, methanesulfonate, having a melting point of 64 to 68.5°C.

Anal. Calcd. for $C_{16}H_{22}O_5S$: C, 58.87; H, 6.80; S, 9.83. Found: C, 59.00; H, 6.86; S, 9.83.

Example 52
4-trans-Acetoxymethyl-4-cis-phenylcyclohexanol, methanesulfonate

A solution of 0.97 g. of 4-trans-acetoxymethyl-4-cis-phenylcyclohexanol (prepared as in Example 44) in 10 ml. of pyridine is cooled in ice. To this solution, 1 ml. of methane sulfonyl chloride is cautiously added. After standing for about 18 hours in the cold, the mixture is poured onto ice and water. The gum that precipitates is extracted with ether. The organic layer is washed successively with water, 2.5 N hydrochloric acid solution, water and brine and then evaporated to dryness. The residual gum amounting to 1.2 g. (94% yield) is shown by NMR to have the structure expected for 4-trans-acetoxymethyl-4-cis-phenylcyclohexanol, methanesulfonate, and is used without purification as the starting material of Example 58.

Example 53
4-cis-Acetoxymethyl-4-trans-4-(4-chlorophenyl)cyclohexanol, methanesulfonate A solution of 6.14 g. of 4-cis-acetoxymethyl-4-trans-(4-chlorophenyl)cyclohexanol (prepared as in Example 45) in 61 ml. of pyridine is cooled in ice. To this solution, 6.1 ml. methanesulfonyl chloride is cautiously added. After standing for about 18 hours in the cold, the mixture is poured onto ice and water. The gum that precipitates is extracted with ether. The organic layer is washed successively with water, 2.5 N hydrochloric acid, water and brine and then evaporated to dryness. The residue is recrystallized from a mixture of methylene chloride and Skellysolve B to give 6.45 g. (81.7% yield) of 4-cis-acetoxymethyl-4-trans-4-(4-chlorophenyl)cyclohexanol, methanesulfonate, having a melting point of 120° to 124°C.

Anal. Calcd. for $C_{16}H_{21}ClO_5$: C, 53.25; H, 5.87; Cl, 9.83. Found: C, 53.52; H, 5.97; Cl, 9.68.

Example 54
4-trans-Acetoxymethyl-4-cis-(4-chlorophenyl)cyclohexanol, methanesulfonate Following the procedure of Example 53 but substituting 4-trans-acetoxymethyl-4-cis-(4-chlorophenyl)cyclohexanol (prepared as in Example 45) as starting materials, yields 4-trans-acetoxymethyl-4-cis-(4-chlorophenyl)cyclohexanol, methanesulfonate.

Example 55
4-cis-Acetoxymethyl-4-trans-(4-fluorophenyl)cyclohexanol, methanesulfonate A solution of 4.55 g. of 4-cis-acetoxymethyl-4-trans-(4-fluorophenyl)cyclohexanol (prepared in Example 46) in 45 ml. of pyridine is cooled in ice. To this solution, 4.5 ml. of methanesulfonyl chloride is cautiously added. After standing for about 18 hours in the cold, the mixture is poured onto ice and water. The gum that precipitates is extracted with ether. The organic layer is washed successively with water, 2.5 N hydrochloric acid, water and brine and then evaporated to dryness. The residue is recrystallized from a mixture of acetone and cyclohexane to give 5.05 g. (86% yield) of 4-cis-acetoxymethyl-4-trans-(4-fluorophenyl)cyclohexanol, methanesulfonate, having a melting point of 95° to 97°C.

Anal. Calcd. for $C_{16}H_{21}FO_5S$: C, 55.80; H, 6.15. Found: C, 55.73; H, 6.43

Example 56
4-trans-Acetoxymethyl-4-cis-(4-fluorophenyl)cyclohexanol, methanesulfonate Following the procedure of Example 55 but substituting 4-trans-acetoxymethyl-4-cis-(4-fluorophenyl)cyclohexanol (prepared as in Example 46) as starting material, yields 4-trans-acetoxymethyl-4-cis-(4-fluorophenyl)cyclohexanol, methanesulfonate.

Example 57
4-cis-Acetoxymethyl-4-trans-(4-methoxyphenyl)cyclohexanol, methanesulfonate A solution of 5.03 g. of 4-cis-acetoxymethyl-4-trans-(4-methoxyphenyl)cyclohexanol (prepared as in Example 47) in 50 ml. of pyridine is cooled in ice. To this solution, 5 ml. of methanesulfonyl chloride is cautiously added. After standing for about 18 hours in the cold, the mixture is poured onto ice and water. The gum that precipitates is extracted with ether. The organic layer is washed successively with water, 2.5 N hydrochloric acid, water, and brine and then evaporated to dryness. The residue is recrystallized from a mixture of methylene chloride and Skellysolve B to give 4.88 g. (75.8% yield) of 4-cis-acetoxymethyl-4-trans-(4-methoxyphenyl)cyclohexanol, methanesulfonate, having a melting point of 101° to 102°C.

Anal. Calcd. for $C_{17}H_{24}O_6S$: C, 57.28; H, 6.79; S, 9.00. Found: C, 57.12; H, 6.98; S, 8.94.

Example 58
4-trans-Acetoxymethyl-4-cis-(4-methoxyphenyl)cyclohexanol, methanesulfonate Following the procedure of Example 57 but substituting 4-trans-acetoxymethyl-4-cis-(4-methoxyphenyl)cyclohexanol (prepared as in Example 47) as starting material, yields 4-trans-acetoxymethyl-4-cis-(4-methoxyphenyl)cyclohexanol, methanesulfonate.

Example 59
4-cis-Acetoxymethyl-4-trans-(3,4-dimethoxyphenyl)cyclohexanol, methanesulfonate A solution of 1.54 g. of 4-cis-acetoxymethyl-4-trans-(3,4-dimethoxyphenyl)cyclohexanol (prepared in Example 48) in 15 ml. of pyridine is cooled in ice. To this solution, 1.6 ml. of methanesulfonyl chloride is cautiously added. After standing for about 18 hours in the cold, the mixture is poured onto ice and water. The gum that precipitates is extracted with ether. The organic layer is washed successively with water, 2.5 N hydrochloric acid, water and brine and then evaporated to dryness. The residual gum amounting to 1.7 g (86% yield) is shown by NMR to have the structure expected for 4-cis-acetoxymethyl-4-trans-(3,4-dimethoxyphenyl)cyclohexanol, methanesulfonate, and is used without purification as the starting material of Example 73.

Example 60
4-trans-Acetoxymethyl-4-cis-(3,4-dimethoxyphenyl)cyclohexanol, methanesulfonate Following the procedure of Example 59 but substituting 4-trans-acetoxymethyl-4-cis-(3,4-dimethoxyphenyl)cyclohexanol (prepared as in Example 48) as starting material, yields 4-trans-acetoxymethyl-4-cis-(3,4-dimethoxyphenyl)cyclohexanol, methanesulfonate.

Example 61
4-cis-Acetoxymethyl-4-trans-(1-naphthyl)cyclohexanol, methanesulfonate A solution of 1.92 g. of 4-cis-acetoxymethyl-4-trans-(1-naphthyl)cyclohexanol (prepared in Example 49) in 20 ml. of pyridine is cooled in ice. To this solution, 2 ml. of methanesulfonyl chloride is cautiously added. After standing for about 18 hours in the cold, the mixture is poured onto ice and water. The gum that precipitates is extracted with ether. The organic layer is washed successively with water. 2.5 N hydrochloric acid, water and brine and then evaporated to dryness. The residual gum amounting to 2.2 g. (90% yield) is shown by NMR to have the structure expected for 4-cis-acetoxymethyl-4-trans-(1-naphthyl)cyclohexanol, methanesulfonate, and is used without purification as the starting material of Example 75.

Example 62
4-trans-Acetoxymethyl-4-cis-(1-naphthyl)cyclohexanol, methanesulfonate Following the procedure of Example 61 but substituting 4-trans-acetoxymethyl-4-cis-(1-naphthyl)cyclohexanol (prepared as in Example 49) as starting material, yields 4-trans-acetoxymethyl-4-cis-(1-naphthyl)cyclohexanol, methanesulfonate.

Example 63 4-cis-Methyl-4-trans-phenylcyclohexanol, methanesulfonate

A solution of 3.08 g. (0.0162 mole) of 4-cis-methyl-4-trans-phenylcyclohexanol (prepared as in Example 50) and 3 ml. of methanesulfonyl chloride in 30 ml. of pyridine is allowed to stand in the cold for about 16 hours. The mixture is diluted with water and then extracted with ether. The organic layer is washed successively with water, 2.5 N hydrochloric acid, water and brine and then evaporated to dryness to give 4-cis-methyl-4-trans-phenylcyclohexanol, methanesulfonate.

Example 64 4-trans-Methyl-4-cis-phenylcyclohexanol, methanesulfonate

Following the procedure of Example 63 but substituting 4-trans-methyl-4-cis-phenylcyclohexanol (prepared as in Example 50) as starting material, yields 4-trans-methyl-4-cis-phenylcyclohexanol, methanesulfonate.

Following the procedure of Examples 51 through 64 but substituting other 4-cis (and trans)-acyloxymethyl (and methyl)-4-trans (and cis)-arylcyclohexanols and other alkyl (or aryl) sulfonyl halides, such as 1. 4-cis (and trans)-acetoxymethyl-4-trans (and cis)-(2-bromophenyl)cyclohexanol and ethanesulfonyl bromide,
2. 4-cis (and trans)-acetoxymethyl-4-trans (and cis)-3,5-diethoxyphenyl)cyclohexanol and p-toluenesulfonyl chloride,
3. 4-cis (and trans)-acetoxymethyl-4-trans (and cis)-(2-ethoxy-4-fluoro-6-propylphenyl)cyclohexanol and benzenesulfonyl chloride,
4. 4-cis (and trans)-methyl-4-trans (and cis)-[(o-3-naphthylphenyl)]cyclohexanol and p-toluenesulfonyl chloride, and the like, yields, respectively, 1. 4-cis (and trans)-acetoxymethyl-4-trans (and cis)-(2-bromophenyl)cyclohexanol ethanesulfonate,
2. 4-cis (and trans)-acetoxymethyl-4-trans (and cis)-(3,5-diethoxyphenyl)cyclohexanol p-toluenesulfonate,
3. 4-cis (and trans)-acetoxymethyl-4-trans (and cis)-(2-ethoxy-4-fluoro-6-propylphenyl)cyclohexanol benzenesulfonate,
4. 4-cis (and trans)-methyl-4-trans (and cis)-[(o-3-naphthylphenyl)]cyclohexanol, -p-toluenesulfonate, and the like.

Example 65
4-cis-Hydroxymethyl-4-trans-phenylcyclohexylamino hydrochloride (I)

A mixture of 1.2 g. (0.0037 mole) of 4-trans-acetoxymethyl-4-cis-phenylcyclohexanol methanesulfonate (prepared in Example 52) and 1.2 g. of sodium azide in 21 ml. of dimethylformamide is heated with stirring for about 17 hours at about 90°C. The solvent is then removed under vacuum and the residue dissolved in benzene and water. The organic layer is washed with water and brine and then evaporated to dryness to give 4-cis-acetoxymethyl-4-trans-phenylcyclohexan-1-ylazide. A solution of this compound in 20 ml. of tetrahydrofuran is added dropwise to 0.33 g (0.0087 mole) of lithium aluminum hydride in 50 ml. of tetrahydrofuran. The mixture is stirred at room temperature for about 6 hours, then cooled in ice and treated successively with 0.33 ml. of water, 0.33 ml. of 15% aqueous sodium hydroxide solution and 1 ml. of water. The inorganic precipitate is separated in a filter and rinsed several times with ether and methylene chloride. The combined filtrates are evaporated to dryness. The residue is dissolved in methanol and the solution treated with an excess of 5N hydrochloric acid in ether. The solution is evaporated to dryness and the residue recrystallized from a mixture of methanol and ethyl acetate to give 0.53 g. (60% yield) of 4-cis-hydroxymethyl-4-trans-phenylcyclohexylamine hydrochloride (I), having a melting point of 215° to 218° C.

Anal. Calcd. for $C_{13}H_{20}ClNO$: C, 64.58; H, 8.34; N, 5.80. Found: C, 64.18; H, 8.40; N, 5.57.

Example 66
4-trans-Hydroxymethyl-4-cis-phenylcyclohexylamine hydrochloride (I)

A mixture of 10.83 g. (0.033 mole) of 4-cis-acetoxymethyl-4-trans-phenylcyclohexanol methanesulfonate (prepared as in Example 51) and 11 g. of sodium azide in 100 ml. of dimethylformamide is heated with stirring for about 17 hours at 90° C. The solvent is then removed under vacuum and the residue dissolved in benzene and water. The organic layer is washed with water and brine and then evaporated to dryness to give 4-trans-acetoxymethyl-4-cis-phenylcyclohexan-1-ylazide. A solution of this compound in 180 ml. of tetrahydrofuran is added dropwise to 3.24 g. (0.085 mole) of lithium aluminum hydride in 35 ml. of tetrahydrofuran. The mixture is stirred at room temperature for about 6 hours, then cooled in ice and treated successively with 3.2 ml. of water, 3.2 ml. of 15% aqueous sodium hydroxide solution and 10 ml. of water. The inorganic precipitate is separated on a filter and rinsed several times with ether and methylene chloride. The combined filtrates are evaporated to dryness. The residue is dissolved in methanol and the solution treated with an excess of 5N hydrochloric acid in ether. The solution is evaporated to dryness and the residue recrystallized from a mixture of methanol and ethyl acetate to give 6.36 g. (80% yield) of 4-trans-hydroxymethyl-4-cis-phenylcyclohexylamine hydrochloride (I), having a melting point of 256° to 258° C.

Anal. Calcd. for $C_{13}H_{20}ClNO$: C, 64.58; H, 8.34; N, 5.80. Found: C, 64.68; H, 8.24; N, 5.87.

Example 67
4-trans-Hydroxymethyl-4-cis-(4-chlorophenyl)cyclohexylamine hydrochloride (I)

A mixture of 3.2 g. (0.089 mole) of 4-cis-acetoxymethyl-4-trans-(4-chlorophenyl)cyclohexanol methanesulfonate (prepared as in Example 53) and 3.2 g. of sodium azide in 32 ml. of dimethylformamide is heated with stirring for about 17 hours at 90° C. The solvent is then removed under vacuum and the residue dissolved in benzene and water. The organic layer is washed with water and brine and then evaporated to dryness to give 4-trans-acetoxymethyl-4-cis-(4-chlorophenyl)cyclohexan-1-ylazide. A solution of this compound in 35 ml. of tetrahydrofuran. The mixture is stirred at room temperature for about 6 hours, then cooled in ice and treated successively with 0.65 ml. of water, 0.65 ml. of 15% aqueous sodium hydroxide solution and 1.95 ml. of water. The inorganic precipitate is separated on a filter and rinsed several times with ether and methylene chloride. The combined filtrates are evaporated to dryness. The residue is dissolved in methanol and the solution treated with an excess of 5N hydrochloric acid in ether. The solution is evaporated to dryness and the residue recrystallized from a mixture of methanol and ethyl acetate to give 1.62 g. (66.1% yield) of 4-trans-hydroxymethyl-4-cis-(4-chlorophenyl)cyclohexylamine hydrochloride (I), having a melting point of 303° to 304.5° C.

Anal. Calcd. for $C_{13}H_{19}Cl_2NO$: C, 56.53; H, 6.93; N, 5.07. Found: C, 56.84; H, 6.98, N, 4.93.

Example 68
4-cis-Hydroxymethyl-4-trans-(4-chlorophenyl)cyclohexylamine hydrochloride (I)

Following the procedure of Example 67 but substituting 4-trans-acetoxymethyl-4-cis-(4-chlorophenyl)cyclohexanol methanesulfonate (prepared as in Example 54) as starting material, yields 4-cis-hydroxymethyl-4-trans-(4-chlorophenyl)cyclohexylamine hydrochloride (I).

Example 69
4-trans-Hydroxymethyl-4-cis-(4-fluorophenyl)cyclohexylamine hydrochloride (I)

A mixture of 5 g. (0.089 mole) of 4-cis-acetoxymethyl-4-trans-(4-fluorophenyl)cyclohexanol methanesulfonate (prepared as in Example 55) and 5 g. of sodium azide in 50 ml. of dimethylformamide is heated with stirring for about 17 hours at about 90° C. The solvent then removed under vacuum and the residue dissolved in benzene and water. The organic layer is washed with water and brine and then evaporated to dryness to give 4-trans-acetoxymethyl-4-cis-(4-fluorophenyl)cyclohexan-1-ylazide. A solution of this compound in 70 ml. of tetrahydrofuran is added dropwise to 1.1 g. (0.029 mole) of lithium aluminum hydride in 20 ml. of tetrahydrofuran. The mixture is stirred at room temperature for about 6 hours, then cooled in ice and treated successively with 1.1 ml. of water, 1.1 ml. of 15% aqueous sodium hydroxide solution and 3.3 ml. of water. The inorganic precipitate is separated in a filter and rinsed several times with ether and methylene chloride. The combined filtrates are evaporated to dryness. The residue is dissolved in methanol and the solution treated with an excess of 5N hydrochloric acid in ether. The solution is evaporated to dryness and the residue recrystallized from a mixture of methanol and ethyl acetate to give 3.17 g. (84% yield) of 4-trans-hydroxymethyl-4-cis-(4-fluorophenyl)cyclohexylamine hydrochloride (I), having a melting point of 288° to 290° C.

Anal. Calcd. for $C_{13}H_{19}ClFNO$: C, 60.11; H, 7.37; N, 5.39. Found: C, 60.04; H, 7.41; N, 5.55.

Example 70
4-cis-Hydroxymethyl-4-trans-(4-fluorophenyl)cyclohexylamine hydrochloride (I)

Following the procedure of Example 69 but substituting 4-trans-acetoxymethyl-4-cis-(4-fluorophenyl)cyclohexanol methanesulfonate (prepared as in Example 56) as starting material, yields 4-cis-hydroxymethyl-4-trans-(4-fluorophenyl)cyclohexylamine hydrochloride (I).

Example 71
4-trans-Hydroxymethyl-4-cis-(4-methoxyphenyl)cyclohexylamine hydrochloride (I)

A mixture of 4.88 g. (0.014 mole) of 4-cis-acetoxymethyl-4-trans-(4-methoxyphenyl)cyclohexanol methanesulfonate (prepared in Example 57) and 4.9 g. of sodium azide in 50 ml. of dimethylformamide is heated with stirring for about 17 hours at about 90° C. The solvent is then removed under vacuum and the residue dissolved in benzene and water. The organic layer is washed with water and brine and then evaporated to dryness to give 4-trans-acetoxymethyl-4-cis-(4-methoxyphenyl)cyclohexan-1-ylazide. A solution of this compound in 50 ml. of tetrahydrofuran is added dropwise to 1 g. (0.026 mole) of lithium aluminum hydride in 10 ml. of tetrahydrofuran. The mixture is stirred at room temperature for about 5 hours, cooled in ice and treated successively with 1 ml. of water, 1 ml. of 15% aqueous sodium hydroxide solution and 3 ml. of water. The inorganic precipitate is separated on a filter and rinsed several times with ether and methylene chloride. The combined filtrates are evaporated to dryness. The residue is dissolved in methanol and the solution treated with an excess of 5N hydrochloric acid in ether. The solution is evaporated to dryness and the residue recrystallized from a mixture of methanol and ethyl acetate to give 1 g. (26.8% yield) of 4-trans-hydroxymethyl-4-cis-(4-methoxyphenyl)cyclohexylamine hydrochloride (I), having a melting point of 267° to 269° C.

Anal. Calcd. for $C_{14}H_{22}ClNO_2$: C, 61.86; H, 8.16; N, 5.15. Found: C, 61.61; H, 8.49; N, 4.91.

Example 72
4-cis-Hydroxymethyl-4-trans-(4-methoxyphenyl)cyclohexylamine hydrochloride (I)

Following the procedure of Example 71 but substituting 4-trans-acetoxymethyl-4-cis(4-methoxyphenyl)cyclohexanol methanesulfonate (prepared as in Example 58) as starting material, yields 4-cis-hydroxymethyl-4-trans-(4-methoxyphenyl)cyclohexylamine hydrochloride (I).

Example 73
4-trans-Hydroxymethyl-4-cis-(3,4-dimethoxyphenyl)-cyclohexylamine hydrochloride (I)

A mixture of 1.7 g. (0.0044 mole) of 4-cis-acetoxymethyl-4-trans-(3,4-dimethoxyphenyl)cyclohexanol methanesulfonate (prepared in Example 59) and 1.7 g. of sodium azide in 17 ml. of dimethylformamide is heated with stirring for about 17 hours at about 90° C. The solvent is then removed under vacuum and the residue dissolved in benzene and water. The organic layer is washed with water and brine and then evaporated to dryness to give 4-trans-acetoxymethyl-4-cis-(3,4-dimethoxyphenyl)cyclohexan-1-ylazide. A solution of this compound in 18 ml. of tetrahydrofuran is added dropwise to 0.33 g. (0.0087 mole) of lithium aluminum hydride in 4 ml. of tetrahydrofuran. The mixture is stirred at room temperature for about 5 hours, cooled in ice and treated successively with 0.33 ml. of 15% aqueous sodium hydroxide solution and 1 ml. of water. The inorganic precipitate is separated on a filter and rinsed several times with ether and methylene chloride. The combined filtrates are evaporated to dryness. The residue is dissolved in methanol and the solution treated with an excess of 5N hydrochloric acid in ether. The solution is evaporated to dryness and the residue recrystallized from a mixture of methanol and ethyl acetate to give 0.81 g. (60% yield) of 4-trans-hydroxymethyl-4-cis-(3,4-dimethoxyphenyl)cyclohexylamine hydrochloride (I), having a melting point of 261° to 263° C.

Anal. Calcd. for $C_{15}H_{24}ClNO_3$: C, 57.96; H, 8.11; N, 4.51. Found: C, 58,23; H, 8.55; N, 4.01.

Example 74
4-cis-Hydroxymethyl-4-trans-(3,4-dimethoxyphenyl)-cyclohexylamine hydrochloride (I)

Following the procedure of Example 73 but substituting 4-trans-acetoxymethyl-4-cis-(3,4-dimethoxyphenyl)cyclohexanol methanefulfonate (prepared as in Example 60) as starting material, yields 4-cis-hydroxymethyl-4-trans-(3,4-dimethoxyphenyl)cyclohexylamine hydrochloride (I).

Example 75
4-trans-Hydroxymethyl-4-cis-(1-naphthyl)cyclohexylamine hydrochloride (I)

A mixture of 2.42 g. (0.00665 mole) of 4-cis-acetoxymethyl-4-trans-(1-naphthyl)cyclohexanol methanesulfonate (prepared in Example 61) and 2.5 g. of sodium azide in 25 ml. of dimethylformamide is heated with stirring for about 17 hours at about 90° C. The solvent is then removed under vacuum and the residue dissolved in benzene and water. The organic layer is washed with water and brine and then evaporated to dryness to give 4-trans-acetoxymethyl-4-cis-(1-naphthyl)cyclohexan-1-ylazide. A solution of this compound in 70 ml. of tetrahydrofuran is added dropwise to 0.65 g. (0.017 mole) of lithium aluminum hydride in 10 ml. of tetrahydrofuran. The mixture is stirred at room temperature for about 5 hours, cooled in ice and treated successively with 0.65 ml. of water, 0.65 ml. of 15% aqueous sodium hydroxide solution and 1.95 ml. of water. The inorganic precipitate is separated on a filter and rinsed several times with ether and methylene chloride. The combined filtrates are evaporated to dryness. The residue is dissolved in methanol and the solution treated with an excess of 5N hydrochloric acid in ether. The solution is evaporated to dryness and the residue recrystallized from a mixture of methanol and ethyl acetate to give 0.57 g. (33% yield) of 4-trans-hydroxymethyl-4-cis-(1-naphthyl)cyclohexylamine hydrochloride (I), having a melting point of 268° to 269° C.

Anal. Calcd. for $C_{17}H_{22}ClNO$: C, 69.96; H, 7.60; N, 4.80. Found: C, 69.59; H, 7.60; N, 4.66.

EXAMPLE 76
4-cis-Hydroxymethyl-4-trans-(1-naphthyl)cyclohexylamine hydrochloride (I)

Following the procedure of Example 75 but substituting 4-trans-acetoxymethyl-4-cis-(1-naphthyl)cyclohexanol methanesulfonate (prepared as in Example 62) as starting material, yields 4-cis-hydroxymethyl-4-trans-(1-naphthyl)cyclohexylamine hydrochloride (I).

Example 77
4-trans-Methyl-4-cis-phenylcyclohexylamine hydrochloride (I)

A mixture of the 4-cis-methyl-4-trans-phenylcyclohexanol methanesulfonate (prepared in Example 63) and 3 g. of sodium azide in 30 ml. of dimethylformamide is stirred for about 17 hours at about 90° C. The solvent is then removed under vacuum and the residue dissolved in benzene and water. The organic layer is washed with water and brine and then evaporated to dryness to give 4-trans-methyl-4-cis-phenylcyclohexan-1-ylazide. A solution of this compound in 60 ml. of tetrahydrofuran is added dropwise to 0.7 g. of lithium aluminum hydride in 10 ml. of tetrahydrofuran. The mixture is stirred at room temperature for about 4 hours and then treated successively with 0.7 ml. of water, 0.7 ml. of 15% aqueous sodium hydroxide solution and 2 ml. of water. The inorganic precipitate is separated on a filter and the filtrate evaporated to dryness. The residue is dissolved in ether and the solution with an excess of 5N hydrochloric acid in ether. The resulting solid is recrystallized several times from a mixture of methanol and ethyl acetate to give 1.26 g. (35% yield) of 4-trans-methyl-4-cis-phenylcyclohexylamine hydrochloride (I), having a melting point of 313° to 315° C.

Anal. Calcd. for $C_{13}H_{20}ClN$: C, 69.16; H, 8.93; N, 6.20. Found: C, 69.16; H, 8.98; N, 5.74.

Example 78
4-cis-Methyl-4-trans-phenylcyclohexylamine hydrochloride (I)

Following the procedure of Example 77 but substituting 4-trans-methyl-4-cis-phenylcyclohexanol methanesulfonate (prepared as in Example 64) as starting material, yields 4-cis-methyl-4-trans-phenylcyclohexylamine hydrochloride (I).

Following the procedure of Example 65 through 78 but substituting for ethereal hydrochloric acid, ether solutions of other acids, such as sulfuric, hydrobromic, nitric, phosphoric, nicotinic, acetic, benzoic and citric acids and the like, yields the corresponding acid addition salts.

Following the procedure of Examples 65 through 78 but substituting other 4-cis (and trans)-acyloxymethyl (and methyl)-4-trans (and cis)-arylcyclohexanol alkyl (and aryl) sulfonates, such as, 1. 4-cis (and trans)-acetoxymethyl-4-trans (and cis)-phenylcyclohexanol methanesulfonate,
2. 4-cis (and trans)-acetoxymethyl-4-trans (and cis)-(4-chlorophenyl)cyclohexanol methanesulfonate,
3. 4-cis (and trans)-acetoxymethyl-4-trans (and cis)-(4-fluorophenyl)cyclohexanol methanesulfonate,
4. 4-cis (and trans)-acetoxymethyl-4-trans (and cis)-(4-methoxyphenyl)cyclohexanol methanesulfonate,
5. 4-cis (and trans)-methyl-4-trans (and cis)-(2-methylthiophenyl)cyclohexanol methanesulfonate,
6. 4-cis (and trans)-acetoxymethyl-4-trans (and cis)-(3-bromophenyl)cyclohexanol propanesulfonate,
7. 4-cis (and trans)-methyl-4-trans (and cis)-(2-chloro-5-methylphenyl)cyclohexanol, α-naphthalenesulfonate,
8. 4-cis (and trans)-propionyloxymethyl-4-trans (and cis)-(2-chloro-4-fluoro-6-propylphenyl)cyclohexanol, p-toluenesulfonate,
9. 4-cis (and trans)-acetoxymethyl-4-trans (and cis)-(2,5-diethoxy-3-ethylthiophenyl)cyclohexanol, benzenesulfonate,
10. 4-cis (and trans)-methyl-4-trans (and cis)-(o-fluorophenyl)cyclohexanol, ethanesulfonate,
11. 4-cis (and trans)-acetoxymethyl-4-trans (and cis)-[2-chloro-5-ethyl-(3-naphthyl)]cyclohexanol, β-naphthalenesulfonate,
12. 4-cis (and trans)-methyl-4-trans (and cis)-[(p-2-naphthylphenyl)]cyclohexanol, p-toluenesulfonate, and the like, yields, respectively, 1. 4-trans (and cis)-hydroxymethyl-4-cis (and trans)-phenylcyclohexylamine hydrochloride (I),
2. 4-trans (and cis)-hydroxymethyl-4-cis (and trans)-(4-chlorophenyl)cyclohexylamine hydrochloride (I)
3. 4-trans (and cis)-hydroxymethyl-4-cis (and trans)-(4-fluorophenyl)cyclohexylamine hydrochloride (I),
4. 4-trans (and cis)-hydroxymethyl-4-cis (and trans)-(4-methoxyphenyl)cyclohexylamine hydrochloride (I),
5. 4-trans (and cis)-methyl-4-cis (and trans)-(2-methylthiophenyl)cyclohexylamine hydrochloride (I),
6. 4-trans (and cis)-hydroxymethyl-4-cis (and trans)-(3-bromophenyl)cyclohexylamine hydrochloride (I),
7. 4-trans (and cis)-methyl-4-cis (and trans)-(2-chloro-5-methylphenyl)cyclohexylamine hydrochloride (I),
8. 4-trans (and cis)-hydroxymethyl-4-cis (and trans)-(2-chloro-4-fluoro-6-propylphenyl)cyclohexylamine hydrochloride (I),
9. 4-trans (and cis)-hydroxymethyl-4-cis (and trans)-(2,5-diethoxy-3-ethylthiophenyl)cyclohexylamine hydrochloride (I),
10. 4-trans (and cis)-methyl-4-cis (and trans)-(o-fluorophenyl)cyclohexylamine hydrochloride (I),
11. 4-trans (and cis)-hydroxymethyl-4-cis (and trans)-[2-chloro-5-ethyl-(3-naphthyl)]cyclohexylamine hydrochloride (I),
12. 4-trans (and cis)-methyl-4-cis (and trans)-[(p-2-naphthylphenyl)]cyclohexylamine hydrochloride (I), and the like.

EXAMPLE 79
N-Methyl-[4-trans-hydroxymethyl-4-cis-(4-fluorophenyl)cyclohexyl]amine hydrochloride (I)

a. N-[4-trans-Hydroxymethyl-4-cis-(4-fluorophenyl)cyclohexyl]formamide (I)

A mixture of 2.5 g. of the free base form of 4-trans-hydroxymethyl-4-cis-(4-fluorophenyl)cyclohexylamine hydrochloride (I) [obtained by stirring 3 g. of an ether solution of its hydrochloride (prepared as in Example 69) with 2.5 ml. of triethylamine] and 30 ml. of ethyl formate, is heated at reflux for about 40 hours. The resulting solution is evaporated to dryness and the residue recrystallized from benzene to give N-[4-trans-hydroxymethyl-4-cis-(4-fluorophenyl)cyclohexyl]formamide (I).

Following the procedure of (a), above, but substituting other esters for ethyl formate, such as ethyl acetate, methyl propionate and the like, yields respectively, N-[4-trans-hydroxymethyl-4-cis-(4-fluorophenyl)cyclohexyl]acetamide (I), N-[4-trans-hydroxymethyl-4-cis-(4-fluorophenyl)cyclohexyl]acetamide (I), N-[4-trans-hydroxymethyl-4-cis-(4-fluorophenyl)cyclohexyl]propionamide (I), and the like.

b.
N-Methyl-[4-trans-hydroxymethyl-4-cis-(4-fluorophenyl)cyclohexyl]amine hydrochloride (I).

A solution of 2.5 g. of N-[4-trans-hydroxymethyl-4-cis-(4-fluorophenyl)cyclohexyl]formamide (I) [obtained as in (a), above] in 75 ml. of tetrahydrofuran is added to a well stirred suspension of 0.65 g. of lithium aluminum hydride in 15 ml. of tetrahydrofuran. After heating this mixture for about 4 hours, it is cooled in ice and 0.6 ml. of water, 0.6 ml. of 15% aqueous sodium hydroxide solution and 1.7 ml. of water are added successively. The solid that precipitates is removed by filtration and the filtrate evaporated to dryness. The residue is dissolved in ether and treated with a small excess of 3.6 N ethereal hydrogen chloride. The solid that precipitates is recrystallized from a mixture of methylene chloride and ethyl acetate to give N-methyl-[4-trans-hydroxymethyl-4-cis-(4-fluorophenyl)cyclohexyl]amine hydrochloride (I).

Following the procedure of (b), above, but substituting N-[4-trans-hydroxymethyl-4-cis-(4-fluorophenyl)-cyclohexyl]acetamide (I), N-[4-trans-hydroxymethyl-4-cis-(4-fluorophenyl)cyclohexyl]propionamide (I), and the like, yields respectively, N-ethyl-[4-trans-hydroxymethyl-4-cis-(4-fluorophenyl)cyclohexyl]amine hydrochloride (I), N-propyl-[4-trans-hydroxymethyl-4-cis-(4-fluorophenyl)cyclohexyl]amine hydrochloride (I), and the like.

Example 80
N-Methyl-[4-cis-hydroxymethyl-4-trans-(4-fluorophenyl)cyclohexyl]amine hydrochloride (I)

a. N-[4-cis-Hydroxymethyl-4-trans-(4-fluorophenyl) cyclohexyl]formamide (I)

A mixture of 2.5 g. of the free base form of 4-cis-hydroxymethyl-4-trans-(4-fluorophenyl)cyclohexylamine hydrochloride (I) [obtained by stirring 3 g. of an ether solution of its hydrochloride (prepared as in Example 70) with 2.5 ml. of triethylamine] and 30 ml. of ethyl formate, is heated at reflux for about 40 hours. The resulting solution is evaporated to dryness and the residue recrystallized from benzene to give N-[4-cis-hydroxymethyl-4-trans-(4-fluorophenyl)cyclohexyl]-formamide (I).

Following the procedure of (a), above, but substituting other esters for ethyl formate, such as ethyl acetate, methyl propionate and the like, yields respectively, N-[4-cis-hydroxymethyl-4-trans-(4-fluorophenyl)cyclohexyl]acetamide (I), N-[4-cis-hydroxymethyl-4-trans-(4-fluorophenyl)cyclohexyl]propionamide (I), and the like.

b. N-Methyl-[4-cis-hydroxymethyl-4-trans-(4-fluorophenyl)cyclohexyl]amine hydrochloride (I)

A solution of 2.5 g. of N-[4-cis-hydroxymethyl-4-trans-(4-fluorophenyl)cyclohexyl]formamide (I) [obtained as in (a), above] in 75 ml. of tetrahydrofuran is added to a well-stirred suspension of lithium aluminum hydride in 15 ml. of tetrahydrofuran. After heating this mixture at reflux for about 4 hours, it is cooled in ice and 0.6 ml. of water, 0.6 ml. of 15% aqueous sodium hydroxide solution and 1.7 ml. of water are added successively. The solid that precipitates is removed by filtration and the filtrate evaporated to dryness. The residue is dissolved in ether and treated with a small excess of 3.6 N ethereal hydrogen chloride. The solid that precipitates is recrystallized from a mixture of methylene chloride and ethyl acetate to give N-methyl-[4-cis-hydroxymethyl-4-trans-(4-fluorophenyl)cyclohexyl]amine hydrochloride (I).

Following the procedure of (b), above, but substituting N-[4-cis-hydroxymethyl-4-trans-(4-fluorophenyl)-cyclohexyl]acetamide (I), N-[4-cis-hydroxymethyl-4-trans-(4-fluorophenyl)cyclohexyl]acetamide (I), N-[4-cis-hydroxymethyl-4-trans-(4-fluorophenyl)cyclohexyl]propionamide (I), and the like, yields respectively, N-ethyl-[4-cis-hydroxymethyl-4-trans-(4-fluorophenyl)cyclohexyl]amine hydrochloride (I), N-propyl-[4-cis-hydroxymethyl-4-trans-(4-fluorophenyl)cyclohexyl]amine hydrochloride (I), and the like.

Following the procedure of Examples 79 and 80 but substituting other 4-trans (and cis)-hydroxymethyl (and methyl)-4-cis (and trans)-arylcyclohexylamines (I) and other alkyl esters of carboxylic acids, such as 1. 4-trans (and cis)-hydroxymethyl-4-cis (and trans) phenylcyclohexylamine (I) and methylformate,
2. 4-trans (and cis)-hydroxymethyl-4-cis (and trans)-(4-chlorophenyl)cyclohexylamine (I) and propyl formate,
3. 4-trans (and cis)-hydroxymethyl-4-cis (and trans)-(4-methoxyphenyl) cyclohexylamine (I) and methyl acetate,
4. 4-trans (and cis)-hydroxymethyl-4-cis (and trans)-(3,4-dimethoxyphenyl)cyclohexylamine (I) and propyl acetate,
5. 4-trans (and cis)-acetoxymethyl-4-cis (and trans)-(1-naphthyl)cyclohexylamine (I) and ethyl propionate,
6. 4-trans (and cis)-methyl-4-cis (and trans)-(2-naphthyl)cyclohexylamine (I) and isopropyl acetate,
7. 4-trans (and cis)-hydroxymethyl-4-cis (and trans)-(2-bromophenyl)cyclohexylamine (I) and isopropyl formate,
8. 4-trans (and cis)-methyl-4-cis (and trans)-(3-chloro-5-ethylphenyl)cyclohexylamine (I) and propyl acetate,
9. 4-trans (and cis)-hydroxymethyl-4-cis (and trans)-(2-chloro-4-ethoxy-6-fluorophenyl)cyclohexylamine (I) and methyl propionate,
10. 4-trans (and cis)-hydroxymethyl-4-cis (and trans)-(2,4-diethyl-6-propoxyphenyl)cyclohexylamine (I) and propyl propionate,
11. 4-trans (and cis)-methyl-4-cis (and trans)-[α-(m-chlorophenyl)cycloheptyl]cyclohexylamine (I) and methyl formate,
12. 4-trans (and cis)-hydroxymethyl-4-cis (and trans)-(2-ethyl-5-methylphenyl)cyclohexylamine and methyl acetate,
13. 4-trans (and cis)-methyl-4-cis (and trans)-[α-(2-bromo-4-fluoro-6-propylthiophenyl)cyclopentyl]cyclohexylamine (I) and ethyl propionate,
14. 4-trans (and cis)-hydroxymethyl-4-cis (and trans)-[(m-3-naphthylphenyl)]cyclohexylamine (I) and isopropyl acetate, and the like, yields, respectively, 1. N-methyl-[4-trans (and cis)-hydroxymethyl-4-cis (and trans)-phenylcyclohexyl]amine hydrochloride (I),
2. N-methyl-[4-trans (and cis)-hydroxymethyl-4-cis (and trans)-(4-chlorophenyl)cyclohexyl]amine hydrochloride (I),
3. N-ethyl-[4-trans (and cis)-hydroxymethyl-4-cis (and trans)-(4-methoxyphenyl)cyclohexyl]amine hydrochloride (I),
4. N-ethyl-[4-trans (and cis)-hydroxymethyl-4-cis (and trans)-(3,4-dimethoxyphenyl)cyclohexyl]amine hydrochloride (I),
5. N-propyl-[4-trans (and cis)-acetoxymethyl-4-cis (and trans)-(1-naphthyl)cyclohexyl]amine hydrochloride (I),
6. N-ethyl-[4-trans (and cis)-methyl-4-cis (and trans)-(2-naphthyl)cyclohexyl]amine hydrochloride (I),
7. N-methyl-[4-trans (and cis)-hydroxymethyl-4-cis (and trans)-(2-bromophenyl)cyclohexyl]amine hydrochloride (I),
8. N-ethyl-[4-trans (and cis)-methyl-4-cis (and trans)-(3-chloro-5-ethylphenyl)cyclohexyl]amine hydrochloride (I),
9. N-propyl-[4-trans (and cis)-hydroxymethyl-4-cis (and trans)-(2-chloro-4-ethoxy-6-fluorophenyl)cyclohexyl]amine hydrochoride (I), 10. N-propyl-[4-trans (and cis)-hydroxymethyl-4-cis (and trans)-(2,4-diethyl-6-propoxyphenyl)cyclohexyl]amine hydrochloride (I), 11. N-methyl-[[4-trans (and cis)-methyl-4-cis (and trans)-[α-(m-chlorophenyl)cycloheptyl]cyclohexyl]-]amine hydrochloride (I), 12. N-ethyl-[[4-trans (and cis)-hydroxymethyl-4-cis (and trans)-(2-ethyl-5-methylphenyl)cyclohexyl]]amine hydrochloride (I), 13. N-propyl-[[4-trans (and cis)-methyl-4-cis (and trans)-[α-(2-bromo-4-fluoro-6-propylthiophenyl)cyclopentyl] cyclohexyl]]amine hydrochloride (I), 14. N-ethyl-[[4-trans (and cis)-hydroxymethyl-4-cis (and trans)-[(m-3-naphthylphenyl)]cyclohexyl]]amine hydrochloride (I), and the like.

Example 81
1-trans-Phenyl-4-cis-(1-pyrrolidino)-1-cyclohexanemethanol (I)

To a mixture of 1.73 g. (0.00655 mole) of 4-cis-hydroxymethyl-4-trans-phenylcyclohexylamine hydrochloride (I) (prepared as in Example 65) and 30 ml. of ethanol, 1.56 ml. of 4.2 N sodium methoxide in methanol is added. After stirring the mixture for about 45 minutes at room temperature, 0.77 ml. of 1,4-dibromobutane and 1.64 g. of potassium carbonate is added. The mixture is then heated at reflux for about 17 hours, allowed to cool and evaporated to dryness under vacuum. The residue is suspended in water, the solid collected on a filter and then recrystallized a mixture of methanol and water to give 1.13 g (66% yield) of 1-transphenyl-4-cis-(1-pyrrolidino)-1-cyclohexanemethanol (I), having a melting point of 180° to 183° C.

Anal. Calcd. for $C_{17}H_{25}NO$: C, 78.71; H, 9.72; N, 5.38. Found: C, 78.51; H, 9.80; N, 5.07.

Example 82
1-cis-Phenyl-4-trans-(1-pyrrolidino)-1-cyclohexanemethanol (I)

Following the procedure of Example 81 but substituting 4-trans-hydroxymethyl-4-cis-phenylcyclohexylamine hydrochloride (I) (prepared as in Example 66) as starting material, yields 1-cis-phenyl-4-trans-(1-pyrrolidino)-1-cyclohexanemethanol (I).

Example 83
1-trans-Phenyl-4-cis-(1-piperidino)-1-cyclohexanemethanol (I)

To a mixture of 1.15 g. (0.005 mole) of 4-cis-hydroxymethyl-4-trans-phenylcyclohexylamine hydrochloride (I) (prepared as in Example 65) and 22 ml. of ethanol, 1.4 ml. of 4.2 N sodium methoxide in methanol is added. After stirring the mixture for about 1 hour at room temperature, 0.7 ml. of 1,5-diiodopentane and 1.76 g. of potassium carbonate is added. The mixture is then heated at reflux for about 17 hours, allowed to cool and evaporated to dryness under vacuum. The residue is suspended in water, the solid collected on a filter and then recrystallized from a mixture of methanol and water to give 0.98 g. (73% yield) of 1-trans-phenyl-4-cis-(1-piperidino)-1-cyclohexanemethanol, having a melting point of 170° to 172° C.

Anal. Calcd. for $C_{18}H_{27}NO$: C, 79.07; H, 9.95; N, 5.12. Found: C, 79.35; H, 10.11; N, 4.93.

Example 84
1-cis-Phenyl-4-trans-(1-piperidino)-1-cyclohexanemethanol (I)

Following the procedure of Example 83 but substituting 4-trans-hydroxymethyl-4-cis-phenylcyclohexylamine hydrochloride (I) (prepared as in Example 66) as starting material, yields 1-cis-phenyl-4-trans-(1piperidino)-1-cyclohexanemethanol (I).

Example 85
1-trans-(1-Naphthyl)-4-cis-(1-piperidino)-1-cyclohexanemethanol (I)

To a mixture of 1.46 g. (0.005 mole) of 4-cis-hydroxymethyl-4-trans-(1-naphthyl)cyclohexylamine hydrochloride (I) (prepared as in Example 76) and 22 ml. of ethanol, 1.4 ml. of 4.2 N sodium methoxide in methanol is added. After stirring the mixture for about 1 hour at room temperature, 0.76 ml. of 1,5-diidopentane and 1.26 g. of potassium carbonate is added. The mixture is then heated at reflux for about 17 hours, allowed to cool and evaporate to dryness under vacuum. The residue is suspended in water, the solid collected on a filter and then recrystallized from a mixture of methanol and water to give 1.15 g. (71% yield) of 1-trans-(1-naphthyl)-4-cis-(1-piperidino)-1-cyclohexanemethanol (I), having a melting point of 170° to 173° C.

Anal. Calcd. for $C_{22}H_{29}NO$: C, 81.69; H, 9.04; N, 4.95. Found: C, 81.39; H, 9.27; N, 4.28.

Example 86
1-cis-(1-Naphthyl)-4-trans-(1-piperidino)-1-cyclohexanemethanol (I)

Following the procedure of Example 85 but substituting 4-trans-hydroxymethyl-4-cis-(1-naphthyl)cyclohexylamine hydrochloride (I) (prepared as in Example 75) as starting material, yields 1-cis-(1-naphthyl)-4-trans-(1-piperidino)-1-cyclohexanemethanol (I).

Example 87
1-trans-(p-Fluorophenyl)-4-cis-(1-piperidino)-1-cyclohexanemethanol (I)

To a mixture of 1.58 g. (0.0061 mole) of 4-cis-hydroxymethyl-4-trans-(4-fluorophenyl)cyclohexylamine hydrochloride (I) (prepared as in Example 70) and 30 ml. of ethanol, 1.5 ml. of 4.2 N sodium methoxide in methanol is added. After stirring the mixture for about 1 hour at room temperature, 0.92 ml. of 1,5-diiodopentane and 1.53 g. of potassium carbonate is added. The mixture is then heated at reflux for about 17 hours, allowed to cool and evaporated to dryness under vacuum. The residue is suspended in water, the solid collected on a filter and then recrystallized from a mixture of methanol and water to give 1.08 g. (61% yield) of 1-trans-(p-fluorophenyl)-4-cis-(1-piperidino)-1-cyclohexanemethanol (I), having a melting point of 161° to 163° C.

Anal. Calcd. for $C_{18}H_{26}FNO.1/2H_2O$: C, 71.96; H, 9.06; N, 4.66. Found: C, 72.18; H, 8.78; N, 5.06.

Example 88
1-cis-(p-Fluorophenyl)-4-trans-(1-piperidino)-1-cyclohexanemethanol (I)

Following the procedure of Example 87 but substituting 4-trans-hydroxymethyl-4-cis-(4-fluorophenyl)cyclohexylamine hydrochloride (I) (prepared as in Example 69) as starting material, yields 1-cis-(p-fluorophenyl)-4-trans-(1-piperidino)-1-cyclohexanemethanol (I).

Example 89
1-trans-Phenyl-4-cis-(1-hexanemethyleneimino)-1-cyclohexanemethanol (I)

Following the procedure of Example 81 but substituting 1,6-diiodohexane for 1,4-dibromobutane yields 1-trans-phenyl-4-cis-(1-hexamethyleneimino)-1-cyclohexanemethanol (I).

Example 90
1-cis-Phenyl-4-trans-(1-hexamethyleneimino)-1-cyclohexanemethanol (I)

Following the procedure of Example 82 but substituting 1,6-diiodohexane for 1,4-dibromobutane yields 1-cis-phenyl-4-trans-(1-hexamethyleneimino)-1-cyclohexanemethanol (I).

Following the procedure of Examples 81 through 90 but substituting acid addition salts of other 4-cis (and trans)-hydroxymethyl (and methyl)-4-trans (and cis)-arylcyclohexylamines (I) and similar dihaloalkanes, such as 1. 4-cis (and trans)-hydroxymethyl-4-trans (and cis)-(1-naphthyl)cyclohexylamine hydrobromide (I) and 1,6-diiodohexane,
2. 4-cis (and trans)-hydroxymethyl-4-trans (and cis)-(4-methoxyphenyl)cyclohexylamine nitrate (I) and 1,5-diiodopentane,
3. 4-cis (and trans)-hydroxymethyl-4-trans (and cis)-(2-chloro-4-ethyl-6-fluorophenyl)cyclohexylamine hydrochloride (I) and 1,5-diiodopentane,
4. 4-cis (and trans)-hydroxymethyl-4-trans (and cis)-(2-ethyl-4-fluorophenyl)cyclohexylamine hydrochloride (I) and 1,4-dibromobutane,
5. 4-cis (and trans)-methyl-4-trans (and cis)-[2-bromo-4-ethyl(3-naphthyl)]cyclohexylamine hydrochloride (I) and 1,5-dibromopentane,
6. 4-cis (and trans)-hydroxymethyl-4-trans (and cis)-[(p-2-naphthylphenyl)]cyclohexylamine hydrochloride (I) and 1,4-diiodopentane, and the like, yields, respectively, 1. 1-cis (and trans)-(1-naphthyl)-4-trans (and cis)-(1-hexamethyleneimino)-1-cyclohexanemethanol (I),
2. 1-cis (and trans)-(4-methoxyphenyl)-4-trans (and cis)-(1-piperidino)-1-cyclohexanemethanol (I),
3. 1-cis (and trans)-(2-chloro-4-ethyl-6-fluorophenyl)-4-trans (and cis)-(1-piperidino)-1-cyclohexanemethanol (I),
4. 1-cis (and trans)-(2-ethyl-4-fluorophenyl)-4-trans (and cis)-(1-pyrrolidino)-1-cyclohexanemethanol (I),
5. 1-cis (and trans)-[2-bromo-4-ethyl-(3-naphthyl)]-4-trans (and cis)-(1-piperidino)-1-cyclohexylmethane (I),
6. 1-cis (and trans)-[(p-2-naphthylphenyl)]-4-trans (and cis)-1-pyrrolidino)-1-cyclohexanemethanol (I), and the like.

Similarly, employing other dihaloalkanes with appropriate modifications of the procedures described in Examples 81 through 90, yields representative 1-cis (and trans)-(1-aryl)-4-trans (and cis)-(1-single ring heterocyclic)-1-cyclohexylmethanols and methanes), (I), such as 1-cis (and trans)-(2-fluorophenyl)-4-trans (and cis)-(1-morpholino)-1-cyclohexanemethanol (I), 1-cis (and trans)-(3,4-dimethoxyphenyl-4-trans (and cis)-(1-[4-methyl]piperazino]-1-cyclohexylmethane (I), 1-cis (and trans)-(2-bromo-5-ethylphenyl)-4-trans (and cis)-[1-(3-ethyl)piperidino]-1-cyclohexanemethanol (I), 1-cis (and trans)-[2-fluoro-4-propoxy-(3-naphthyl)]-4-trans (and cis)-[1-(2-methyl)morpholino]-1-cyclohexanemethanol (I), 1-cis (and trans)-(2,4-dichloro-6-methylphenyl)-4-trans (and cis)-[1-(3-propyl)pyrrolidino]-1-cyclohexanemethanol (I), 1-cis (and trans)-[(o-3-naphthylphenyl)]-4-trans (and cis)-[1-(3-ethoxy)hexamethyleneimino]-1-cyclohexylmethane (I) 1-cis (and trans)-(4-propylphenyl)-4-trans (and cis)-[1-(2-methyl)piperazino]-1-cyclohexanemethanol (I), 1-cis (and trans)-(3-methylthiophenyl)-4-trans (and cis)-[1-(2-ethoxy)morpholino]-1-cyclohexanemethanol (I), 1-cis (and trans)-(2,4,6-tri-ethylphenyl)-4-trans (and cis)-(1-hexamethyleneimino)-1-cyclohexanemethanol (I), and the like.

Example 91
1-trans-(4-Fluorophenyl)-4-cis-(1-piperidino)-1-cyclohexanemethanol acetate (ester) p-toluenesulfonate (I)

a.
4-cis-Acetoxymethyl-4-trans-(4-fluorophenyl)cyclohexylamine hydrochloride (I)

A mixture of 5.17 g. (0.015 mole) of 4-trans-acetoxymethyl-4-cis-(4-fluorophenyl)cyclohexanol methanesulfonate (prepared as in Example 56) and 5 g. of sodium azide in 50 ml. of dimethylformamide is heated in an oil bath at 90° C. for about 18 hours. The solvent is removed under vacuum and the residue dissolved in benzene and water. The organic layer is washed with water and brine and then evaporated to dryness. To a solution of the oily residue in 150 ml. of ethyl acetate, 0.45 g. of 10% palladium on charcoal catalyst is added and the mixture shaken for about 6 hours with hydrogen under a pressure of 50 lbs/square inch. The catalyst is collected on a filter and the filtrate evaporated to dryness. The residue is taken up in ether and an excess of 5N hydrochloric acid added to precipitate the crude product, which on recrystallization from a mixture of methylene chloride and ethyl acetate gives 3.5 g. (77.5% yield) of 4-cis-acetoxymethyl-4-trans-(4-fluorophenyl)cyclohexylamine hydrochloride (I), having a melting point of 201° to 202° C.

Anal. Calcd. for $C_{15}H_{21}ClFNO_2$: C, 59.69; H, 7.01; N, 4.64. Found: C, 59.57; H, 7.07; N, 4.32.

b.
1-trans-(4-Fluorophenyl)-4-cis-(1-piperidino)-1-cyclohexanemethanol acetate (ester) p-toluenesulfonate (I)

To a mixture of 1.75 g. (0.0058 mole) of 4-cis-acetoxymethyl-4-trans-(4-fluorophenyl)cyclohexylamine hydrochloride (I) [obtained as in (a) above] in 30 ml. of dimethylformamide, 0.25 g. of 56% sodium hydride is added. After standing for about 1 hour at room temperature, 0.88 ml. of diiodopentane and 1.46 g. of potassium carbonate is added and the mixture heated for about 17 hours at about 75° C. Most of the solvent is removed under vacuum and the residue dissolved in water and benzene. The organic layer is washed with water and brine and then evaporated to dryness. The residue is dissolved in ether and this solution treated 1.2 g. of p-toluenesulfonic acid in ether to precipitate the crude product. The precipitated solid is recrystallized from a mixture of methylene chloride and ethyl acetate to give 2.03 g. (69% yield) of 1-trans-(4-fluorophenyl)-4-cis-(1-piperidino)-1-cyclohexanemethanol acetate (ester) p-toluenesulfonate (I), having a melting point of 203° to 204° C.

Anal. Calcd. for $C_{27}H_{36}FNO_5S$: C, 64.13; H, 7.18; N, 2.77. Found: C, 63.72; H, 7.28; N, 3.15.

Example 92
1-cis-(4-Fluorophenyl)-4-trans-(1-piperidino)-1-cyclohexanemethanol acetate (ester) p-toluenesulfonate (I)

Following the procedure of Example 91 but substituting 4-cis-acetoxymethyl-4-trans-(4-fluorophenyl)cyclohexanol methansulfonate (prepared as in Example 55) as starting material, yields 1-cis-(4-fluorophenyl)-4-trans-(1-piperidino)-1-cyclohexanemethanol acetate (ester) p-toluenesulfonate (I).

Following the procedure of Examples 91 and 92 but substituting other 4-cis (and trans)acyloxymethyl-4-trans (and cis)-arylcyclohexanol alkyl (or aryl) sulfonates in Example 91 (a) and similar dihaloalkanes in Example 91 (b), such as 1. 4-trans (and cis)-acetoxymethyl-4-cis (and trans)-(1-naphthyl)cyclohexanol benzenesulfonate and 1,4-dibromobutane.
2. 4-trans (and cis)-propionyloxy-4-cis (and trans)-(4-methoxyphenyl)cyclohexanol propanesulfonate and 1,5-diiodopentane,
3. 4-trans (and cis)-propionyloxy-4-cis (and trans)-(3-fluoro-5-propoxyphenyl)cyclohexanol p-toluenesulfonate and 1,4-diiodopentane,
4. 4-trans (and cis)-acetoxymethyl-4-cis (and trans)-[(o-3-naphthylphenyl)]cyclohexanol ethanesulfonate and 1,5-dibromopentane, and the like, yields, respectively;

1. 1-trans (and cis)-(1-naphthyl)-4-cis (and trans)-(1-pyrrolidino)-1-cyclohexanemethanol acetate (ester) p-toluenesulfonate (I),
2. 1-trans (and cis)-(4-methoxyphenyl)-4-cis (and trans)-(1-piperidino)-1-cyclohexanemethanol propionate (ester) p-toluenesulfonate (I),
3. 1-trans (and cis)-(3-fluoro-5-propoxyphenyl)-4-cis (and trans)-1-pyrrolidino)-1-cyclohexanemethanol propionate (ester) p-toluenesulfonate (I),
4. 1-trans (and cis)-[(o-3-naphthylphenyl)]-4-cis (and trans)-(1-piperidino)-1-cyclohexanemethanol acetate (ester) p-toluenesulfonate (I), and the like.

Example 93 4-Chlorobutyrophenone, 2,2-dimethylpropylene ketal a. 4-Chlorobutyrophenone To an ice cooled suspension of 35.5 g. (0.27 mole) of aluminum chloride in 175 ml. of benzene, a solution of 35.5 g. (0.25 mole) of 4-chlorobutyrylchloride in 35 ml. of benzene is added. The reaction mixture is stirred for about 40 minutes at room temperature and then poured into ice and water. The organic layer and one benzene extract of the remaining aqueous fraction are combined, washed first with water, next with brine, and then evaporated to dryness. The residue is distilled at 0.5 to 0.6 mm. of mercury to give 40.56 g. of 4-chlorobutyrophenone, having a boiling point of 104° to 107° C. at the aforesaid pressure.

b. 4-Chlorobutyrophenone, 2,2-dimethylpropylene ketal

A solution of 40.56 g. (0.225 mole) of 4-chlorobutyrophenone [prepared in (a), above], 23.2 g. (0.225 mole) of 2,2-dimethyl-1,3-propanediol (prepared as in J. Am. Chem. Soc. 70, 946) and 0.54 g. of p-toluenesulfonic acid in 400 ml. of benzene is heated at reflux under a Dean-Stark trap for about 20 hours. The solution is allowed to cool, washed successively with aqueous sodium bicarbonate solution, water and brine and then evaporated to dryness. The residue is distilled at 0.35 to 0.5 mm. of mercury to give 21.14 g. (31.5% yield) of 4-chlorobutyrophenone, 2,2-dimethylpropylene ketal, having a boiling point of 117° to 118° C. at the aforesaid pressure. The expected structure of the compound is confirmed by its IR and NMR spectra.

Example 94 4-Chloro-4'-methylbutyrophenone, 2,2-dimethylpropylene ketal a. 4-Chloro-4'-methylbutyrophenone To an ice cooled suspension of 35.5 g. (0.27 mole) of aluminum chloride in 205 ml. of toluene, a solution of 35.5 g. (0.25 mole) of 4-chlorobutyrylchloride is added. The reaction mixture is stirred for about 40 minutes at room temperature and then poured into ice and water. The organic layer and one benzene extract of the remaining aqueous fraction are combined, washed first with water, next with brine and then evaporated to dryness. The residue is distilled at 0.5 to 0.85 mm. of mercury to give 42.8 g. (86.5% yield) of 4-chloro-4'-methylbutyrophenone, having a boiling of 123° to 126° C. at the aforesaid pressure.

Anal. Calcd. for $C_{11}H_{13}ClO$: C, 67.11; H, 6.66; Cl, 18.03. Found: C, 67.18; H, 6.62; Cl, 17.57.

b. 4-Chloro-4'-methylbutyrophenone, 2,2-dimethylpropylene ketal

A solution of 42.8 g. (0.218 mole) of 4-chloro-4'-methylbutyrophenone [prepared in (a), above], 28 g. (0.27 mole) of 2,2-dimethyl-1,3-propanediol and 0.53 g. of p-toluenesulfonic acid in 425 ml. of benzene is heated at reflux under a Dean-Stark trap for about 20 hours. The solution is allowed to cool, washed successively with aqueous sodium bicarbonate solution, water and brine then evaporated to dryness. The residue is recrystallized from petroleum ether mainly pentanes and hexanes to give 51.03 g. of 4-chloro-4'-methylbutyrophenone, 2,2-dimethylpropylene ketal, having a melting point of 78.5° to 82° C.

Anal. Calcd. for $C_{16}H_{23}ClO_2$: C, 67.95; H, 8.20; Cl, 12.54. Found: C, 68.18; H, 8.21; Cl, 12.37.

Example 95 4-Chloro-4'-methoxybutyrophenone, 2,2-dimethylpropylene ketal a. 4-Chloro-4'-methoxybutyrophenone To an ice cooled suspension of 35.5 g. (0.27 mole) of aluminum chloride in 240 ml. of anisole, a solution of 35.5 g. (0.25 mole) of 4-chlorobutyrylchloride in 35 ml. of anisole is added. The reaction mixture is stirred for about 40 minutes at room temperature and then poured into ice and water. The organic layer and one benzene extract of the remaining aqueous fraction are combined, washed first with water, next with brine and then evaporated to dryness. The residue is distilled at 0.8 to 0.9 mm. of mercury to give 45.96 g. (86.2%) of 4-chloro-4'-methoxybutyrophenone, having a boiling point of 152° to 154° C. at the aforesaid pressure.

b. 4-Chloro-4'-methoxybutyrophenone, 2,2-dimethylpropylene ketal

A solution of 45.96 g. (0.217 mole) of 4-chloro-4-methoxybutyrophenone [prepared in (a), above], 28 g. (0.27 mole) of 2,2-dimethyl-1,3-propanediol and 0.53 g. of p-toluenesulfonic acid in 425 ml. of benzene is heated at reflux under a Dean-Stark trap for about 20 hours. The solution is allowed to cool, washed successively with aqueous sodium bicarbonate solution, water and brine and then evaporated to dryness. The residue is distilled at 174° C. at 1.5 mm. of mercury pressure and then recrystallized from petroleum ether to give 19.97 g. (30.9% yield) of 4-chloro-4'-methoxybutyrophenone, 2,2-dimethylpropylene ketal, having a melting point of 51.5° to 53.5° C.

Anal. Calcd. for $C_{16}H_{23}ClO_3$: C, 64.31; H, 7.76; Cl, 11.87 Found: C, 63.82; H, 7.85; Cl, 11.88.

Example 96 4,4'-Dichlorobutyrophenone, 2,2-dimethylpropylene ketal a. 4,4-Dichlorobutyrophenone

To an ice cooled suspension of 35.5 g. (0.27 mole) of aluminum chloride in 250 ml. of monochlorobenzene, a solution of 35.5 g. (0.25 mole of 4-chlorobutyrylchloride in 35 ml. of monochlorobenzene is added. The reaction mixture is stirred for about 40 minutes at room temperature and then poured into ice and water. The organic layer and one benzene extract of the remaining aqueous fraction are combined, washed first with water, next with brine and then evaporated to dryness. The residue is distilled at 0.8 to 1.1 mm. of mercury to give 40.94 g. (75.6% yield) of 4,4'-dichlorobutyrophenone, having a boiling point of 135° to 140° C. at the aforesaid pressure.

Anal Calcd. for $C_{10}H_{10}Cl_2O$: C, 55.32; H, 4.64; Cl, 32.66. Found: C, 55.68; H, 4.77; Cl, 32.16.

b. 4,4'-Dichlorobutyrophenone, 2,2-dimethylpropylene ketal

A solution of 40.94 g. (0.189 mole) of 4,4'-dichlorobutyrophenone [prepared in (a), above], 24.4 g. (0.234 mole) of 2,2-dimethyl-1,3-propanediol and 0.46 g. of p-toluenesulfonic acid in 425 ml. of benzene is heated at reflux under a Dean-Stark trap for about 20 hours. The solution is allowed to cool, washed successively with aqueous sodium bicarbonate solution, water and brine and then evaporated to dryness. The residue is recrystallized from Skellysolve B to give 42.04 g. (73.5% yield) of 4,4'-dichlorobutyrophenone, 2,2-dimethylpropylene ketal, having a melting point of 87° to 92° C.

Anal. Calcd. for $C_{15}H_{20}Cl_2O_2$: C, 59.41; H, 6.65; Cl, 23.39. Found: C, 59.54; H, 6.81; Cl, 23.24.

Example 97 4-Chloro-4'-fluorobutyrophenone, 2,2-dimethylpropylene ketal a. 4-Chloro-4'-fluorobutyrophenone

To a ice cooled suspension of 35.5 g. (0.27 mole) of aluminum chloride in 250 ml. of monofluorobenzene, a solution of 35.5 g. (0.25 mole) of 4-chlorobutyrylchloride in 35 ml. of monofluorobenzene is added. The reaction mixture is stirred for about 40 minutes at room temperature and then poured into ice water. The organic layer and one benzene extract of the remaining aqueous fraction are combined, washed first with water, next with brine and then evaporated to dryness. The residue is distilled at 0.8 to 1 mm. of mercury to give 40.94 g. (82% yield) of 4-chloro-4'-fluorobutyrophenone, having a boiling point of 120° to 125° C. at the aforesaid pressure.

b. 4-Chloro-4'-fluorobutyrophenone, 2,2-dimethylpropylene ketal

A solution of 40.94 g. (0.205 mole) of 4-chloro-4'-fluorobutyrophenone [prepared as in (a), above], 24.4 g. (0.234 mole) of 2,2-dimethyl-1,3-propanediol and 0.46 g. of p-toluenesulfonic acid in 370 ml. of benzene is heated at reflux under a Dean-Stark trap for about 20 hours. The solution is allowed to cool, washed successively with aqueous sodium bicarbonate solution, water and brine and then evaporated to dryness. The residue is recrystallized from Skellysolve B to give 42 g. (71.5% yield) of 4-chloro-4'-fluorobutyrophenone, 2,2-dimethylpropylene ketal, having a melting point of 60° to 62° C.

Following the procedure of Examples 93 through 97 but substituting other aromatic compounds and other ω-haloacyl halides as starting materials, such as 1. bromobenzene and 3-bromopropionyl bromide,
2. ethylbenzene and 3-chloropropionyl chloride,
3. naphthalene and 5-chlorovaleryl fluoride,
4. 2-methylnaphthalene and 6-bromohexanoyl chloride, and the like, yields, respectively, 1. 1-bromo-4'-bromopropiophenone, 2,2-dimethylpropylene ketal,
2. 3-chloro-4'-ethylpropiophenone, 2,2-dimethylpropylene ketal,
3. 5-chloropentynaphthone, 2,2-dimethylpropylene ketal,
4. 6-chloro-(2-methyl)hexanonaphthone, 2,2-dimethylpropylene ketal, and the like.

Example 98 4'-Fluoro-4-[[4-cis-(hydroxymethyl)-4-trans-phenyl-r-1-cyclohexyl]amino]butyrophenone hydrochloride (I)

A mixture of the free base obtained from 2.33 g. (0.007 mole) of 4-cis-hydroxymethyl-4-trans-phenylcyclohexylamine hydrochloride (I) (prepared as in Example 65), 1.32 g. of potassium iodide, 2.14 g. of potassium carbonate and 1.96 g. of 4-chloro-4'-fluorobutyrophenone, 2,2-dimethylpropylene ketal (prepared as in Example 97) in 40 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 10 ml. of 2.5N hydrochloric acid in 20 ml. of methanol is stirred at room temperature for about 3 hours. Most of the methanol is removed under vacuum and the resulting residue washed twice with ether and then extracted thoroughly with methylene chloride. This last extracted solution is evaporated to dryness and the solid crude product recrystallized from a mixture of methanol and ethyl acetate to give 1 g. (31.9% yield) of 4'-fluoro-4-[[4-cis-(hydroxymethyl)-4-trans-phenyl-4-1-cyclohexyl]amino]butyrophenone hydrochloride (I), having a melting point of 178° to 180° C.

Anal. Calcd. for $C_{23}H_{29}ClFNO_2$: C, 68.05; H, 7.20; N, 3.45. Found: C, 67.89; H, 7.16; N, 2.92.

Example 99
4'-Fluoro-[[4-trans-(hydroxymethyl)-4-cis-phenyl-r-1-cyclohexyl]amino]butyrophenone hydrochloride (I)

A mixture of 0.406 g. (0.002 mole) of 4-trans-hydroxymethyl-4-cis-phenylcyclohexylamine (I) obtained from its hydrochloride (prepared as in Example 66), 0.39 g. of potassium iodide, 0.7 g. of potassium carbonate and 0.57 g. of 4-chloro-4'-fluorobutyrophenone, 2,2-dimethylpropylene ketal in 10 ml. of dimethylformamide is stirred for about 17 hours at about 90° C. The solvent is then removed under vacuum and residue dissolved in benzene and water. The organic layer is washed with water and brine and then evaporated to dryness. A mixture of the residue and 10 ml. of 2.5N hydrochloric acid in 20 ml. of methanol is stirred at room temperature for about 3 hours. Most of the methanol is removed under vacuum and the resulting residue washed twice with ether and then extracted thoroughly with methylene chloride. This last extracted solution is washed with aqueous 1N sodium hydroxide solution and evaporated to dryness. The residue is chromatographed on silica gel plates with elution by methylene chloride saturated with ammonium hydroxide. The more polar band is eluted and converted to the hydrochloric acid salt to give 0.183 g. (22.8% yield) of 4'-fluoro-[[4-trans-(hydroxymethyl)-4-cis-phenyl-r-1-cyclohexyl]amino]amino]butyrophenone hydrochloride (I) as an amorphous foam. The expected structure predicted for this compound is supported by its NMR and IR spectra.

Example 100
4-[[4-trans-(p-Chlorophenyl)-4-cis(hydroxymethyl)-r-1-cyclohexyl]amino]-4'-fluorobutyrophenone hydrochloride (I)

A mixture of the free base obtained from 1.88 g. (0.0065 mole) of 4-cis-hydroxymethyl-4-trans-(4-chlorophenyl)cyclohexylamine hydrochloride (I) (prepared as in Example 68), 1.09 g. of potassium iodide, 1.76 g. of potassium carbonate and 1.62 g. of 4-chloro-4'-fluorobutyrophenone, 2,2-dimethylpropylene ketal in 33 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 8 ml. of 2.5N hydrochloric acid in 16 ml. of methanol is stirred at room temperature for about 3 hours. Most of the methanol is removed under vacuum and the resulting residue washed twice with ether and then thoroughly extracted with methylene chloride. This last extracted solution is evaporated to dryness and the solid crude product recrystallized from a mixture of methanol and ethyl acetate to give 0.09 g. (32.3% yield) of 4-[[4-trans-(p-chlorophenyl)-4-cis-(hydroxymethyl)-r-1-cyclohexyl]amino]-4'-fluorobutyrophenone hydrochloride (I), having a melting point of 173° to 177° C.

Anal. Calcd. for $C_{23}H_{28}Cl_2FNO_2$: C, 62.73; H, 6.41; N, 3.18. Found: C, 62.98; H, 6.48, N, 3.10.

Example 101
4-[[4-cis-(p-Chloropheyl)-4-trans-(hydroxymethyl)-r-1-cyclohexyl]amino]-4'-fluorobutyrophenone hydrochloride (I)

Following the procedure of Example 100 but substituting the free base obtained from 4-trans-hydroxymethyl-4-cis-(4-chlorophenyl)cyclohexylamine hydrochloride (I) (prepared as in Example 67) as starting material, yields 4-[[4-cis-(p-chlorophenyl)-4-trans-(hydroxymethyl)-r-1-cyclohexyl]amino]-4'-fluorobutyrophenone hydrochloride (I).

Example 102
4'-Fluoro-4-[[-trans-(p-fluorophenyl)-4-cis-(hydroxymethyl)-r-1-cyclohexyl]amino]butyrophenone hydrochloride (I)

A mixture of the free base obtained from 1.58 g. (0.0061 mole) of 4-cis-hydroxymethyl-4-trans-(4-fluorophenyl) cyclohexylamine hydrochloride (I) (prepared as in Example 70), 1.05 g. of potassium iodide, 1.8 g. of potassium carbonate and 1.47 g. of 4-chloro-4'-fluorobutyrophenone, 2,2-dimethylpropylene ketal in 38 ml. of dimethylformamide is stirred for about 17 hours at about 90° C. The solvent is then removed under vacuum and the residue dissolved in benezene and water. The organic layer is washed with water and brine and then evaporated to dryness. A mixture of the residue and 10 ml. of 2.5N hydrochloric acid in 20 ml. of methanol is stirred at room temperature for about 3 hours. Most of the methanol is removed under vacuum and the resulting residue washed twice with ether and then thoroughly extracted with methylene chloride. This last extracted solution is evaporated to dryness and the solid crude product recrystallized from a mixture of methylene chloride and ethyl acetate to give 0.64 g. (24.7% yield) of 4'-fluoro-4-[[4-trans-(p-fluorophenyl)-4-cis-(hydroxymethyl)-r-1-cyclohexyl]amino]butyrophenone hydrochloride (I), having a melting point of 196° to 198° C.

Anal. Calcd. for $C_{23}H_{28}ClNF_2O_2$: C, 65.16, H, 6.66 N, 3.33. Found: C, 65.81; H, 6.76; N, 3.13.

Example 103
4'-Fluoro-4-[[4-cis-(p-fluorophenyl)-4-trans-hydroxymethyl)-r-1-cyclohexyl]amino]butyrophenone hydrochloride (I)

Following the procedure of Example 102 but substituting the free base obtained from 4-trans-hydroxymethyl-4-cis-(4-fluorophenyl)cyclohexylamine hydrochloride (I) (prepared as in Example 69) as starting material, yields 4'-fluoro-4-[[4-cis-(p-fluorophenyl)-4-trans-(hydroxymethyl)-r-1-cyclohexyl]amino]-butyrophenone hydrochloride (I).

Example 104
4'-Fluoro-4-[[4-cis-(hydroxymethyl)-4-trans-(p-methoxyphenyl)-r-1-cyclohexyl]amino]butyrophenone hydrochloride (I)

A mixture of the free base obtained from 1.14 g. (0.0043 mole) of 4-cis-hydroxymethyl-4-trans-(4-methoxyphenyl)cyclohexylamine hydrochloride (I) (prepared as in Example 72), 0.7 g. of potassium iodide, 1.13 g. of potassium carbonate and 1.04 g. of 4-chloro-4'-fluorobutyrophenone, 2,2-dimethylpropylene ketal in 21 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 5 ml. of 2.5N hydrochloric acid in 10 ml. of methanol is stirred at room temperature for about 3 hours. Most of the methanol is removed under vacuum and the resulting residue washed twice with ether and then thoroughly extracted with methylene chloride. This last extracted solution is evaporated to dryness and the solid crude product recrystallized from a mixture of methanol and ethyl acetate to give 0.54 g. (30.3% yield) of 4′-fluoro-4-[[4-cis-(hydroxymethyl)-4-trans-(p-methoxyphenyl)-r-1-cyclohexyl]amino]butyrophenone hydrochloride (I), having a melting point of 164° to 166° C.

Anal. Calcd. for $C_{24}H_{31}ClFNO_2$: C, 66.12; H, 7.17; N, 3.21. Found: C, 66.03; H, 7.17; N, 3.16.

Example 105
4′-Fluoro-4-[[4-trans-(hydroxymethyl)-4-cis-(p-methoxyphenyl)-r-1-cyclohexyl]amino]butyrophenone hydrochloride (I)

Following the procedure of Example 104 but substituting the free base obtained from 4-trans-hydroxymethyl-4-cis-(4-methoxyphenyl)cyclohexylamine hydrochloride (I) (prepared as in Example 71) as starting material, yields 4′-fluoro-4-[[4-trans-(hydroxymethyl)-4-cis-(p-methoxyphenyl)-r-1-cyclohexyl]amino]-butyrophenone hydrochloride (I).

Example 106
4′-Fluoro-4-[[-4-cis-(hydroxymethyl)-4-trans-(1-naphthyl)-r-1-cyclohexyl]amino]butyrophenone hydrochloride (I)

A mixture of the free base obtained from 1.46 g. (0.005 mole) of 4-cis-hydroxymethyl-4-trans-(1-naphthyl)cyclohexylamine hydrochloride (I) (prepared as in Example 76, 0.85 g. of potassium iodide, 1.39 g. of potassium carbonate and 1.2 g. of 4-chloro-4′-fluorobutyrophenone, 2,2-dimethylpropylene ketal in 30 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 10 ml. of 2.5N hydrochloric acid in 20 ml. of methanol is stirred at room temperature for about 3 hours. Most of the methanol is removed under vacuum and the resulting residue washed twice with ether and then thoroughly extracted with methylene chloride. This last extracted solution is evaporated to dryness and the solid crude product recrystallized from a mixture of methanol and acetone to give 0.45 g. (19.5% yield) of 4′-fluoro-4-[[4-cis(hydroxymethyl)-4-trans-(1-naphthyl)-r-1-cyclohexyl]amino]butyrophenone hydrochloride (I), having a melting point of 202 to 203° C.

Anal. Calcd. for $C_{27}H_{31}FNO_2$: C, 71.11; H, 6.85; N, 3.07. Found: C, 71.38; H, 6.97; N, 3.21.

EXAMPLE 107
4′-Fluoro-4-[[4-trans-(hydroxymethyl)-4-cis-(1-naphthyl)-r-1-cyclohexyl]amino]butyrophenone hydrochloride (I)

Following the procedure of Example 106 but substituting the free base obtained from 4-trans-hydroxymethyl-4-cis-(1-naphthyl)cyclohexylamine hydrochloride (I) (prepared as in Example 75) as starting material, yields 4′-fluoro-4-[[4-trans-(hydroxymethyl)-4-cis-(1-naphthyl)-r-1-cyclohexyl]amino]butyrophenone hydrochloride (I).

EXAMPLE 108
4′-Fluoro-4-[[4-cis(hydroxymethyl)-4-trans-phenyl-r-1-cyclohexyl]amino]butyrophenone acetate (ester) hydrochloride a.
4-cis-Acetoxymethyl-4-trans-phenylcyclohexylamine hydrochloride (I)

A mixture of 10 g. (0.0306 mole) of 4-trans-acetoxymethyl-4-cis-phenylcyclohexanol, methanesulfonate (prepared as in Example 52) and 9 g. of sodium azide in 90 ml. of dimethylformamide is heated for about 18 hours at about 90° C. The solvent is removed under vacuum and the residue dissolved in benzene and water. The organic layer is washed with water and brine and then evaporated to dryness. The residue is dissolved in 150 ml. of ethyl acetate and 0.45 g. of 10% palladium on carbon catalyst added. The mixture is shaken under an atmosphere of hydrogen for about 3 hours, then the catalyst is collected on a filter and the filtrate evaporated to dryness. The residue is dissolved in ether and an excess of 6N hydrochloric acid in ether is added, resulting in a partially crystalline precipitate. This material is separated and recrystallized first from a mixture of methylene chloride and ethyl acetate and then a mixture of methanol and ethyl acetate to give 2.38 g. (27.4% yield) of 4-cis-acetoxymethyl-4-trans-phenylcyclohexylamine hydrochloride, having a melting point of 195.5° to 198° C.

Anal. Calcd. for $C_{15}H_{22}ClNO_2 \cdot \frac{1}{2}H_2O$: C, 61.52; H, 7.92; N, 4.78. Found: C, 61.63; H, 7.79; N, 4.85.

b.
4′-Fluoro-4-[[4-cis-(hydroxymethyl)-4-trans-phenyl-r-1-cyclohexyl]amino]butyrophenone acetate (ester), hydrochloride (I)

A mixture of the free base obtained from 1.7 g. (0.006 mole) of 4-cis-acetoxymethyl-4-trans-phenylcyclohexylamine hydrochloride (I) [obtained as in (a), above), 1.02 g. of potassium iodide, 1.67 g. of potassium carbonate and 1.44 g. of 4-chloro-4′-fluorobutyrophenone, 2,2-dimethylpropylene ketal in 35 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 2.5 ml. of 2.5N hydrochloric acid in 50 ml. of methanol is stirred at room temperature for about 3 hours. Most of the methanol is removed under vacuum and the resulting residue washed twice with ether and then thoroughly extracted with methylene chloride. This last extracted solution is evaporated to dryness and the solid crude product recrystallized from ethyl acetate to give 0.55 g. (20.5% yield) of 4′-fluoro-4-[[4-cis-(hydroxymethyl)-4-trans-phenyl-r-1-cyclohexyl]amino]butyrophenone acetate (ester), hydrochloride (I), having a melting point of 138° to 139° C.

Anal. Calcd. for $C_{25}H_{31}ClFNO_3$: C, 67.02; H, 6.98; N, 3.13. Found: C, 66.46; H, 7.14; N, 3.13.

EXAMPLE 109
4′-Fluoro-4-[[4-trans-(hydroxymethyl)-4-cis-phenyl-r-1-cyclohexyl]amino]butyrophenone acetate (ester), hydrochloride (I)

Following the procedure of Example 108 but substituting 4-cis-acetoxymethyl-4-trans-phenylcyclohexylanol, methanesulfonate (prepared as in Example 51) as starting material in (a), yields 4'-fluoro-4-[[4-trans-(hydroxymethyl)-4-cis-phenyl-r-1-cyclohexyl]amino]-butyrophenone acetate (ester), hydrochloride (I).

EXAMPLE 110
4'-Fluoro-4-[[4-cis-(hydroxymethyl)-4-trans-(p-methoxyphenyl)-r-1-cyclohexyl]amino]butyrophenone acetate (ester), hydrochloride a.
4-cis-Acetoxymethyl-4-trans-(4-methoxyphenyl)cyclohexylamine hydrochloride (I)

A mixture of 4.5 g. (0.0126 mole) of 4-trans-acetoxymethyl-4-cis-(4-methoxyphenyl)cyclohexanol, methanesulfonate (prepared as in Example 58) and 4.5 g. of sodium azide in 45 ml. of dimethylformamide is heated at about 90° C. for about 18 hours. The solvent is removed under vacuum and the residue dissolved in benzene and water. The organic layer is washed with water and brine and then evaporated to dryness. The residue is dissolved in 150 ml. of ethyl acetate and 0.16 g. of 10% palladium on carbon catalyst added. The mixture is shaken under an atmosphere of hydrogen for about 3 hours, then the catalyst is collected on a filter and the filtrate evaporated to dryness. The residue is dissolved in ether and an excess of 6N hydrochloric acid in ether is added, resulting in a crystalline precipitate. This material is collected on a filter and recrystallized from a mixture of methanol and ether to give 2.55 g. (64.6% yield) of 4-cis-acetoxymethyl-4-trans-(4-methoxyphenyl)cyclohexamine hydrochloride, having a melting point of 191.5° to 193° C.

Anal. Calcd. for $C_{16}H_{24}ClNO_3$: C, 61.23; H, 7.71; N, 4.46. Found: C, 61.19; H, 7.82; N, 4.15.

b.
4'-Fluoro-4-[[4-cis-(hydroxymethyl)-4-trans-(p-methoxyphenyl)-r-1-cyclohexyl]amino]butyrophenone acetate (ester), hydrochloride (I)

A mixture of the free base obtained from 2.35 g. (0.0075 mole) of 4-cis-acetoxymethyl-4-trans-(4-methoxyphenyl)cyclohexylamine hydrochloride (I) [obtained as in (a), above], 1.27 g. of potassium iodide, 2.07 g. of potassium carbonate and 1.79 g. of 4-chloro-4'-fluorobutyrophenone, 2,2-dimethylpropylene ketal in 44 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 3 ml. of 2.5N hydrochloric acid in 60 ml. of methanol is stirred at room temperature for about 3 hours. Most of the methanol is removed under vacuum and the resulting residue washed twice with ether and then thoroughly extracted with methylene chloride. This last extracted solution is washed with aqueous N sodium hydroxide solution and then evaporated to dryness. The residue is chromatographed on 300 ml. of silica gel and eluted with a mixture of 3 parts of ether and 1 part of methylene chloride with said mixture saturated with ammonium hydroxide. The more polar fractions are combined and converted to 4'-fluoro-4-[[4-cis(hydroxymethyl)-4-trans-(p-methoxyphenyl)-r-1-cyclohexyl]amino]butyrophenone acetate (ester), hydrochloride (I) as an amorphous foam. Its expected structure is confirmed by its NMR and IR spectra.

EXAMPLE 111
4'-Fluoro-4[[4-trans-(hydroxymethyl)-4-cis-(p-methoxyphenyl)-r-1-cyclohexyl]amino]butyrophenone acetate (ester), hydrochloride (I)

Following the procedure of Example 110 but substituting 4-cis-acetoxymethyl-4-trans-(4-methoxyphenyl)cyclohexanol, methanesulfonate (prepared as in Example 57) as starting material in (a), yields 4'-fluoro-4-[[4-trans-(hydroxymethyl)-4-cis-(p-methoxyphenyl)-r-1-cyclohexyl]amino]butyrophenone acetate (ester, hydrochloride (I).

EXAMPLE 112
4'-Fluoro-4-[[4-cis-methyl-4-trans-phenyl-r-1-cyclohexyl]amino]butyrophenone hydrochloride (I)

A mixture of the free base obtained from 1.26 g. (0.056 mole) of 4-cis-methyl-4-trans-phenylcyclohexylamine hydrochloride (I) (prepared as in Example 78), 1.13 g. of potassium iodide, 1.76 g. of potassium carbonate and 1.61 g. of 4-chloro-4'-fluorobutyrophenone, 2,2-dimethylpropylene ketal in 30 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 10 ml. of 2.5N hydrochloric acid in 20 ml. of methanol is stirred at room temperature for about 3 hours. Most of the methanol is removed under vacuum and the resulting residue washed twice with ether and then thoroughly extracted with methylene chloride. This last extracted solution is evaporated to dryness and the solid crude product recrystallized from a mixture of methylene chloride and benzene to give 0.87 g. (40.5% yield) of 4'-fluoro-4-[[4-cis-methyl-4-trans-phenyl-r-1-cyclohexyl]amino]butyrophenone hydrochloride (I), having a melting point of 194° to 197° C.

Anal. Calcd. for $C_{23}H_{29}ClFNO$: C, 70.84; H, 7.50; N, 3.59. Found: C, 71.09; H, 7.61; N, 3.38.

EXAMPLE 113
4'-Fluoro-4-[[4-trans-methyl-4-cis-phenyl-r-1-cyclohexyl]amino]butyrophenone hydrochloride (I)

Following the procedure of Example 112 but substituting the free base obtained from 4-trans-methyl-4-cis-phenylcyclohexylamine hydrochloride (I) (prepared as in Example 77) as starting material, yields 4'-fluoro-4-[[4-trans-methyl-4-cis-phenyl-r-1-cyclohexyl]amino]-butyrophenone hydrochloride (I).

EXAMPLE 114
4-[[4-cis-(Hydroxymethyl)-4-trans-phenyl-r-1-cyclohexyl]amino]butyrophenone (I)

A mixture of the free base obtained from 1.69 g. (0.007 mole) of 4-cis-hydroxymethyl-4-trans-phenylcyclohexylamine hydrochloride (I) (prepared as in Example 65), 1.4 g. of potassium iodide, 2.19 g. of potassium iodide, and 1.88 g. of 4-chlorobutyrophenone, 2,2-dimethylpropylene ketal (prepared as in Example 93) in 35 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 15 ml. of 2.5N hydrochloric acid in 30 ml. of methanol is stirred at room temperature for about 3 hours. Most of the methanol is removed under vacuum and the resulting residue washed twice with ether and then extracted thoroughly with methylene chloride. This last extracted solution is washed with aqueous N sodium hydroxide solution and then evaporated to dryness. The residue is chromatographed on 250 ml. of silica gel and eluted with a mixture of 25% ethanol and 75% methylene chloride with said mixture saturated with ammonium hydroxide. The crystalline fractions are combined and recrystallized from methanol to give 0.31 g. (12.6% yield) of 4-[[4-cis-(hydroxymethyl)-4-trans-phenyl-r-1-cyclohexyl]amino]butyrophenone (I), having a melting point of 100° to 101° C.

Anal. Calcd. for $C_{23}H_{29}NO_2$: C, 78.59; H, 8.32; N, 3.99. Found: C, 78.44; H, 7.87; N, 3.91.

EXAMPLE 115
4-[[4-trans-(hydroxymethyl)-4-cis-phenyl-r-1-cyclohexyl]amino]butyrophenone (I)

Following the procedure of Example 114 but substituting the free base obtained from 4-trans-hydroxymethyl-4-cis-phenylcyclohexylamine hydrochloride (I) (prepared as in Example 66) as starting material, yields 4-[[-trans-(hydroxymethyl)-4-cis-phenyl-r-1-cyclohexyl]amino]butyrophenone (I).

EXAMPLE 116
4-[[4-(Hydroxymethyl)-4-trans-phenyl-r-1-cyclohexyl]amino]-4'-methylbutyrophenone (I)

A mixture of the free base obtained from 1.69 g. (0.007 mole) of 4-cis-hydroxymethyl-4-trans-phenylcyclohexylamine hydrochloride (I) (prepared as in Example 65), 1.4 g. of potassium iodide, 2.19 g. of potassium carbonate and 1.88 g. 4-chloro-4'-methylbutyrophenone, 2,2-dimethylpropylene ketal (prepared as in Example 94) in 35 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 15 ml. of 2.5N hydrochloric acid in 30 ml. of methanol is stirred at room temperature for about 3 hours. Most of the methanol is removed under vacuum and the resulting residue washed twice with ether and then thoroughly extracted with methylene chloride. This last extracted solution is washed with aqueous N soldium hydroxide and then evaporated to dryness. The residue is chromatographed on 250 ml. of silica gel and eluted with a mixture of 25% ethanol and 75% methylene chloride with said mixture saturated with ammonium hydroxide. The crystalline fractions are combined and recrystallized from methanol to give 0.35 g. (13.7% yield) of 4-[[-cis-(hydroxymethyl)-4-trans-phenyl-r-1-cyclohexyl]amino]-4'-methylbutyrophenone (I), having a melting point of 123° to 125° C.

Anal. Calcd. for $C_{24}H_{31}NO_2$: C, 78.86; H, 8.50; N, 3.84. Found: C, 79.26; H, 8.28; N, 2.52.

EXAMPLE 117
4-[[4-trans-(hydroxymethyl)-4-cis-phenyl-r-1-cyclohexyl]amino]-4'-methylbutyrophenone (I)

Following the procedure of Example 116 but substituting the free base obtained from 4-trans-hydroxymethyl-4-cis-phenylcyclohexylamine hydrochloride (I) (prepared as in Example 66) as starting material, yields 4-[[4-trans-(hydroxymethyl)-4-cis-phenyl-r-1-cyclohexyl]amino]-4-methylbutylphenone (I).

EXAMPLE 118
4-[[4-cis-(Hydroxymethyl)-4-trans-phenyl-r-1-cyclohexyl]amino]-4'-methoxybutyrophenone (I)

A mixture of the free base obtained from 1.69 g. (0.007 mole) of 4-cis-hydroxymethyl-4-trans-phenylcyclohexylamine hydrochloride (I) (prepared as in Example 65), 1.4 g. of potassium iodide, 2.19 g. of potassium carbonate and 2.09 g. of 4-chloro-4'-methoxybutyrophenone, 2,2-dimethylpropylene ketal (prepared as in Example 95) in 35 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue and 15 ml. of 2.5N hydrochloric acid in 30 ml. of methanol is stirred at room temperature for about 3 hours. Most of the methanol is removed under vacuum and the resulting residue washed with ether and then extracted thoroughly with methylene chloride. This last extracted solution is washed with aqueous N sodium hydroxide and then evaporated to dryness. The residue is chromatographed on 150 ml. of silica gel and eluted with a mixture of 1 part of ether and 1 part of methylene chloride with said mixture saturated with ammonium hydroxide. The crystalline fractions are combined and recrystallized from methanol to give 0.41 g. (19.7% yield) of 4-[[4-cis-(hydroxymethyl)-4-trans-phenyl-r-1-cyclohexyl]amino]-4'-methoxybutyrophenone (I), having a melting point of 98° to 99° C.

Anal. Calcd. for $C_{24}H_{31}NO_3$: C, 75.56; H, 8.19; N, 3.67. Found: C, 75.44; H, 7.80; N, 2.42.

EXAMPLE 119
4-[[4-trans-(Hydroxymethyl)-4-cis-phenyl-r-1-cyclohexyl]amino]-4'-methoxybutyrophenone (I)

Following the procedure of Example 118 but substituting the free base obtained from 4-trans-hydroxymethyl-4-cis-phenylcyclohexylamine hydrochloride (I) (prepared as in Example 66) as starting material, yields 4-[[4-trans-(hydroxymethyl)-4-cis-phenyl-r-1-cyclohexyl]amino]-4'-methoxybutyrophenone (I).

EXAMPLE 120
4-[[4-cis-(Hydroxymethyl)-4-trans-phenyl-r-1-cyclohexyl]amino]-4'-chlorobutyrophenone hydrochloride (I)

A mixture of the free base obtained from 1.5 g. (0.006mole) of 4-cis-hydroxymethyl-4-trans-phenylcyclohexylamine hydrochloride (I) (prepared as in Example 65), 1.27 g. of potassium iodide, 1.94 g. of potassium carbonate and 1.88 g. of 4,4'-dichlorobutyrophenone, 2,2-dimethylpropylene ketal (prepared as in Example 96) in 30 ml. of dimethylformamide is stirred for about 17 hours at about 90° C. The solvent is then removed under vacuum and the residue dissolved in benzene and water. The organic layer is washed with water and brine and then evaporated to dryness. A mixture of the residue in 10 ml. of 2.5N hydrochloric acid in 30 ml. of methanol is stirred at room temperature for about 3 hours. Most of the methanol is removed under vacuum and the resulting residue washed twice with ether and then thoroughly extracted with methylene chloride. This last extracted solution is evaporated to dryness and recrystallized twice from a mixture of methanol and ethyl acetate to give 1.25 g. (47.3% yield) of 4-[[4-cis-hydroxymethyl)-4-transphenyl-r-1-cyclohexyl]amino]-4'-chlorobutyrophenone hydrochloride (I), having a melting point of 164° to 167° C.

Anal. Calcd. for $C_{23}H_{29}Cl_2NO_2$: C, 65.39; H, 6.92; N, 3,32. Found: C, 64.82; H, 7.14; N, 3.71.

Example 121
4-[[4-trans-(Hydroxymethyl)-4-cis-phenyl-r-1-cyclohexyl]amino]-4'-chlorobutyrophenone hydrochloride (I)

Following the procedure of Example 120 but substituting the free base obtained from 4-trans-hydroxymethyl-4-cis-phenylcyclohexylamine hydrochloride (I) (prepared as in Example 66) as starting material, yields 4-[[4-trans-(hydroxymethyl)-4-cis-phenyl-r-1-cyclohexyl]amino]-4'-chlorobutyrophenone hydrochloride (I).

Following the procedure of Example 98 through 121 but substituting the acid addition salt or free base of other 4-trans (and cis)-hydroxymethyl (acyloxymethyl and methyl)-4-cis (and trans)-arylcyclohexylamines (I) and other ω-haloalkanaryl ketone, 2,2-dimethylpropylene ketals as starting materials, such as 1. 4-trans (and cis)-methyl-4-cis (and trans)-(3-methylthiophenyl)cyclohexylamine hydrobromide (I) and 4-bromo-4'-ethoxybutyrophenone, 2,2-dimethylpropylene ketal, 2. 4-trans (and cis)-hydroxymethyl-4-cis (and trans)-(2-naphthyl)cyclohexylamine (I) and 4-chloro-2'-methylbutyrophenone, 2,2-dimethylpropylene ketal, 3. 4-trans (and cis)-acetoxymethyl-4-cis (and trans)-(3-chloro-5-propylphenyl)cyclohexylamine hydrochloride (I) and 3-chloro-4'-ethylpropiophenone, 2,2-dimethylpropylene ketal, 4. 4-trans (and cis)-hydroxymethyl-4-cis (and trans)-(2-bromo-4-fluoro-6-methylphenyl)cyclohexylamine nitrate (I) and 3',4-dichlorobutyrophenone, 2,2-dimethylpropylene ketal, 5. N-ethyl-[4-trans (and cis)-hydroxymethyl-4-cis (and trans)-(2-ethyl-4-methoxyphenyl)cyclohexyl]amine hydrochloride (I) and 4-bromo-4'-fluorobutyrophenone, 2,2-dimethylpropylene ketal, 6. 4-trans (and cis)-hydroxymethyl-4-cis (and trans)-[2-chloro-6-ethyl-(3-naphthyl)]cyclohexylamine hydrochloride (I) and 5-chloro-4'-ethylvalerophenone, 2,2-dimethylpropylene ketal, and the like, yields, respectively, 1. 4'-ethoxy-4-[[4-trans (and cis)-methyl-4-cis (and trans)-(3-methylthiophenyl)-r-1-cyclohexyl]amino]-butyrophenone hydrobromide (I), 2. 2'-methyl-4-[[4-trans (and cis)-hydroxymethyl)-4-cis (and trans)-(2-naphthyl)-r-1-cyclohexyl]amino]-butyrophenone (I), 3. 4'-ethyl-3-[[4-trans (and cis)-hydroxymethyl)-4-cis (and trans)-(3-chloro-5-propylphenyl)-r-1-cyclohexyl]amino]propiophenone acetate (ester), hydrochloride (I), 4. 3'-chloro-4-[[4-trans (and cis)-(hydroxymethyl)-4-cis (and trans)-(2-bromo-4-fluoro-6-methylphenyl)-r-1-cyclohexyl]amino]butyrophenone nitrate (I), 5. 4'-fluoro-4-[[4-trans (and cis)-(hydroxymethyl)-(2-ethyl-4-methoxyphenyl)-r-1-cyclohexyl]ethylamino]butyrophenone hydrochloride (I), 6. 4'-ethyl-5-[[4-trans (and cis-(hydroxymethyl)-4-cis (and trans-[2-chloro-6-ethyl(3-naphthyl)-]-r-1-cyclohexyl]-amino]valerophenone hydrochloride (I), and the like.

I claim:

1. A compound of the formula

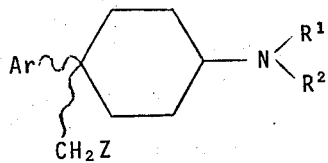

wherein Ar is an aromatic ring selected from the group consisting of phenyl and naphthyl each of which has from zero through three substituents independently selected from the group consisting of fluorine, chlorine, bromine, lower alkyl of one through three carbon atoms, lower alkoxy of one through three carbon atoms, and lower alkylthio of one through three carbon atoms; Z is selected from the group consisting of hydrogen, hydroxy and loweralkanoyloxy of one through four carbon atoms; ~ is a generic expression denoting cis and trans stereoconfiguration and mixtures thereof, with the proviso that when the stereoconfirguration of the linkage connecting the cyclohexane ring and $CH_2Z$ is cis to the amino group, the linkage connecting the cyclohexane and Ar rings is always trans, and vice versa; $R^1$ is selected from the group consisting of hydrogen and lower alkyl of one through three carbon atoms; $R^2$ is

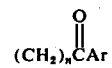

wherein $n$ is 2 through 5 and Ar has the same meaning as above and a pharmacologically acceptable acid addition salt thereof.

2. A compound of claim 1 wherein Ar is phenyl having trans stereoconfiguration, Z is hydroxy, $R^1$ is hydrogen, $R^2$ is 4-oxo-4-(p-fluorophenyl)butyl and the acid addition salt is that of hydrochloric acid, namely, 4'-fluoro-4-[[4-trans-(hydroxymethyl)-4-cis-phenyl-r-1-cyclohexyl]-amino]butyrophenone hydrochloride.

3. A compound of claim 1 wherein Ar is phenyl having cis stereoconfiguration, Z is hydroxy, $R^1$ is hydrogen, $R^2$ is 4-oxo-4-(p-fluorophenyl)butyl and the acid addition salt is that of hydrochloric acid, namely, 4'-fluoro-4-[[4-cis-(hydroxymethyl)-4-trans-phenyl-r-1-cyclohexyl]amino]butyrophenone hydrochloride.

4. A compound of claim 1 wherein Ar is p-fluorophenyl having trans stereoconfiguration Z is hydroxy, $R^1$ is hydrogen, $R^2$ is 4-oxo-4-(p-fluorophenyl)butyl and the acid addition salt is that of hydrochloric acid, namely, 4'-fluoro-4-[[4-trans-(p-fluorophenyl)-4-cis-(hydroxymethyl)-r-1-cyclohexyl]amino]butyophenone hydrochloride.

5. A compound of claim 1 wherein Ar is p-fluorophenyl having cis stereoconfiguration, Z is hydroxy, $R^1$ is hydrogen, $R^2$ is 4-oxo-4-(p-fluorophenyl)butyl and the acid addition salt is that of hydrochloric acid, namely, 4'-fluoro-4-[[4-cis-(p-fluorophenyl)-4-trans-(hydroxymethyl)-r-1-cyclohexyl]-amino]butyrophenone hydrochloride.

6. A compound of claim 1 wherein Ar is p-methoxyphenyl having trans stereoconfiguration, Z is hydroxy, $R^1$ is hydrogen, $R^2$ is 4-oxo-4-(p-fluorophenyl)butyl and the acid addition salt is that of hydrochloric acid, namely, 4'-fluoro-4-[[4-cis-(hydroxymethyl)-4-trans- (p-methoxyphenyl)-r-1-cyclohexyl]amino]butyrophenone hydrochloride.

7. A compound of claim 1 wherein Ar is p-methoxyphenyl having cis stereoconfiguration, Z is hydroxy, $R^1$ is hydrogen, $R^2$ is 4-oxo-(p-fluorophenyl)butyl and the acid addition salt is that of hydrochloric acid, namely, 4'-fluoro-4-[[4-trans-(hydroxymethyl)-4-cis-(p-methoxyphenyl)-r-1-cyclohexyl]amino]butyrophenone hydrochloride.

8. A compound of claim 1 wherein Ar is p-chlorophenyl having trans stereoconfiguration, Z is hydroxy, $R^1$ is hydrogen, $R^2$ is 4-oxo-(p-fluorophenyl)butyl and the acid addition salt is that of hydrochloric acid, namely, 4-[[4-trans-(p-chlorophenyl)-4-cis-(-hydroxymethyl)-r-1-cyclohexyl]amino]-4'-fluorobutyrophenone hydrochloride.

9. A compound of claim 1 wherein Ar is p-chlorophenyl having cis stereoconfiguration, Z is hydroxy, $R^1$ is hydrogen, $R^2$ is 4-oxo-4-(p-fluorophenyl)butyl and the acid addition salt is that of hydrochloric acid, namely, 4-[[4-cis-(-p-chlorophenyl)-4-trans-(hydroxymethyl)-r-1-cyclohexyl]-amino]-4'-fluorobutyrophenone hydrochloride.

10. A compound of claim 1 wherein Ar is 1-naphthyl having trans stereoconfiguration, Z is hydroxy, $R^1$ is hydrogen, $R^2$ is 4-oxo-4-(p-fluorophenyl)butyl and the acid addition salt is that of hydrochloric acid, namely, 4'-fluoro-4-[[4-cis-(hydroxymethyl)-4-trans-(1-naphthyl)-r-1-cyclohexyl]amino]-butyrophenone hydrochloride.

11. A compound of claim 1 wherein Ar is 1-naphthyl having cis stereoconfiguration, Z is hydroxy, $R^1$ is hydrogen, $R^2$ is 4-oxo-(p-fluorophenyl)butyl and the acid addition salt is that of hydrochloric acid, namely, 4'-fluoro-4-[[4-trans-(hydroxymethyl)-4-cis-(1-naphthyl)-r-1-cyclohexyl]amino]butyrophenone hydrochloride.

12. A compound of claim 1 wherein Ar is phenyl having trans stereoconfiguration, Z is acetoxy, $R^1$ is hydrogen, $R^2$ is 4-oxo-4-(p-fluorophenyl)butyl and the acid addition salt is that of hydrochloric acid, namely, 4'-fluoro-4-[[4-cis-(hydroxymethyl)-4-trans-phenyl-r-1-cyclohexyl]amino]butyrophenone, acetate (ester) hydrochloride.

13. A compound of claim 1 wherein Ar is phenyl having cis stereoconfiguration, Z is acetoxy, $R^1$ is hydrogen, $R^2$ is 4-oxo-4-(p-fluorophenyl)butyl and the acid addition salt is that of hydrochloric acid, namely, 4'-fluoro-4-[[4-trans-(hydroxymethyl)-4-cis-phenyl-r-1-cyclohexyl[amino]-butyrophenone, acetate (ester) hydrochloride.

14. A compound of claim 1 wherein Ar is p-methoxyphenyl having trans stereoconfiguration, Z is acetoxy, $R^1$ is hydrogen, $R^2$ is 4-oxo-4-(p-fluorophenyl)butyl and the acid addition salt is that of hydrochloric acid, namely, 4'-fluoro-4-[[4-cis-(hydroxymethyl)-4-trans-(p-methoxyphenyl)-r-1-cyclohexyl]amino]butyrophenone, acetate (ester) hydrochloride.

15. A compound of claim 1 wherein Ar is p-methoxyphenyl- having cis stereoconfiguration, Z is acetoxy, $R^1$ is hydrogen, $R^2$ is 4-oxo-4-(p-fluorophenyl)butyl and the acid addition salt is that of hydrochloric acid, namely, 4'-fluoro-4-[[4-trans-(hydroxymethyl)-4-cis-(p-methoxyphenyl)-r-1-cyclohexyl]amino]butyrophenone, acetate (ester) hydrochloride.

16. A compound of claim 1 wherein AR is phenyl having trans stereoconfiguration, Z and $R^1$ are hydrogen, $R^2$ is 4-oxo-4-(p-fluorophenyl)butyl and the acid addition salt is that of hydrochloric acid, namely, 4'-fluoro-4-[(4-cis-methyl-4-trans-phenyl-r-1-cyclohexyl)amino]butyrophenone hydrochloride.

17. A compound of claim 1 wherein in Ar is phenyl having cis stereoconfiguration, Z and $R^1$ are hydrogen, $R^2$ is 4-oxo-4-(p-fluorophenyl)butyl and the acid addition salt is that of hydrochloric acid, namely, 4'-fluoro-4-[(4-trans-methyl-4-cis-phenyl-r-1-cyclohexyl)amino]butyrophenone hydrochloride.

18. A compound of claim 18 wherein Ar is phenyl having trans stereoconfiguration, Z is hydroxy, $R^1$ is hydrogen and $R^2$ is 4-oxo-4-phenylbutyl, namely, 4-[[4-cis-(hydroxymethyl)-4-trans-phenyl-r-1-cyclohexyl]amino]butyrophenone.

19. A compound of claim 1 wherein Ar is phenyl having cis stereoconfiguration, Z is hydroxy, $R^1$ is hydrogen and $R^2$ is 4-oxo-4-phenylbutyl, namely, 4-[[4-trans-(hydroxymethyl)-4-cis-phenyl-r-1-cyclohexyl]amino]butyrophenone.

20. A compound of claim 1 wherein Ar is phenyl having trans stereoconfiguration, Z is hydroxy, $R^1$ is hydrogen and $R^2$ is 4-oxo-4-(p-methylphenyl)butyl, namely, 4-[[4-cis-(hydroxymethyl)-4-trans-phenyl-r-1-cyclohexyl]amino]-4'-methylbutyrophenone.

21. A compound of claim 1 wherein Ar is phenyl cis stereoconfiguration, Z is hydroxy, $R^1$ is hydrogen, and $R^2$ is 4-oxo-4-(p-methylphenyl)butyl, namely, 4-[[4-trans-(hydroxymethyl)-4-cis-phenyl-r-1-cyclohexyl]amino]-4'-methylbutyrophenone.

22. A compound of claim 1 wherein Ar is phenyl having trans stereoconfiguration, Z is hydroxy, $R^1$ is hydrogen and $R^2$ is 4-oxo-4-(p-methoxyphenyl)butyl, namely, 4-[[4-cis-(hydroxymethyl)-4-trans-phenyl-r-1-cyclohexyl]amino]-4'-methoxybutyrophenone.

23. A compound of claim 1 wherein Ar is phenyl having cis stereoconfiguration, Z is hydroxy, $R^1$ is hydrogen and $R^2$ is 4-oxo-(p-methoxyphenyl)butyl, namely, 4-[[4-trans(hydroxymethyl)-4-cis-phenyl-r1-cyclohexyl]amino]-4'-methoxybutyrophenone.

24. A compound of claim 1 wherein Ar is phenyl having trans stereoconfiguration, Z is hydroxy, $R^1$ is hydrogen, $R^2$ is 4-oxo-4-(p-chlorophenyl)butyl and the acid addition salt is that of hydrochloric acid, namely, 4-[[4-cis-(hydroxymethyl)-4-trans-phenyl-r-1-cyclohexyl]amino]-4'-chlorobutyrophenone hydrochloride.

25. A compound of claim 1 wherein Ar is phenyl having cis stereoconfiguration, Z is hydroxy, $R^1$ is hydrogen, $R^2$ is 4-oxo-4-(p-chlorophenyl)butyl and the acid addition salt is that of hydrochloric acid, namely, 4-[[4-trans-(hydroxymethyl)-4-cis-phenyl-r-1-cyclohexyl]amino]-4'-chlorobutyrophenone hydrochloride.

* * * * *

UNITED STATES PATENT AND TRADEMARK OFFICE
CERTIFICATE OF CORRECTION

PATENT NO. : 3,979,444
DATED : September 7, 1976
INVENTOR(S) : Daniel Lednicer

It is certified that error appears in the above—identified patent and that said Letters Patent is hereby corrected as shown below:

Column 1, line 20: "   " should read -- I --.
Column 1, line 35: "CHαZ" should read -- CH₂Z --.
Column 2, line 50: "mallic" should read -- malic --.
Column 5, line 5: "-N   " should read -- -N) --.
Column 6, line 13: "crystallization. Mixing" should read -- crystallization.
     (10) Mixing --.
Column 6, line 22: "4cis" should read -- 4-cis --.
Column 6, line 22: "acryloxymethyl-" should read -- acyloxymethyl- --.
Column 6, line 27: "stereoconfiguration corresponding" should read
  -- stereoconfiguration) corresponding --.
Column 7, line 64: "hydroxymethyl or" should read -- hydroxymethyl (or --.
Column 9, line 24: "I" should read -- (I) --.
Column 11, line 15: "4-(41-" should read -- 4-(4- --.
Column 13, line 27: "-4cyano-" should read -- -4-cyano- --.
Column 15, line 19: "-(3-" should read -- -4-(3- --.
Column 15, line 49: "-(3,5-" should read -- -5-(3,5- --.
Column 17, line 68: "-4phenylcyclohexa-" should read -- -4-phenylcyclo-
  hexa- --.
Column 25, line 45: "pured" should read -- poured --.
Column 26, lines 61-62: "cyclohexanine" should read -- cyclohexanone --.
Column 30, line 67: "arylcylohexanone" should read -- arylcyclohexanone --.
Column 37, line 68: "58,23;" should read -- 58.23; --.
Column 38, line 7: "methanefulfonate" should read -- methanesulfonate --.
Column 44, line 9: "(1piperidino)" should read -- (1-piperidino) --.
Column 45, line 5: "1-hexanemethyleneimino" should read -- 1-hexamethylene-
  imino --.
Column 51, line 55: "0.09" should read -- 0.9 --.
Column 51, line 64: "Chloropheyl" should read -- Chlorophenyl --.
Column 52, line 8: "4-[[-trans-" should read -- 4-[[4-trans- --.
Column 57, line 68: "-4-" should read -- -4'- --.

UNITED STATES PATENT AND TRADEMARK OFFICE
CERTIFICATE OF CORRECTION

PATENT NO. : 3,979,444

DATED : September 7, 1976

INVENTOR(S) : Daniel Lednicer

It is certified that error appears in the above—identified patent and that said Letters Patent is hereby corrected as shown below:

Column 59, line 5: "3,32." should read -- 3.32. --.
Column 61, line 5: "4-oxo-(p-" should read -- 4-oxo-4-(p- --.
Column 61, line 12: "4-oxo-(p-" should read -- 4-oxo-4-(p- --.
Column 61, line 33: "4-oxo-(p-" should read -- 4-oxo-4-(p- --.
Column 62, line 5: "AR" should read -- Ar --.
Column 62, line 17: "18" should read -- 1 --.
Column 62, line 45: "4-oxo-(p-" should read -- 4-oxo-4-(p- --.
Column 62, line 46: "phenyl-rl-" should read -- phenyl-r-1- --.

Signed and Sealed this

Twenty-fourth Day of November 1981

[SEAL]

Attest:

GERALD J. MOSSINGHOFF

Attesting Officer    Commissioner of Patents and Trademarks